(12) United States Patent
Peng et al.

(10) Patent No.: US 10,941,188 B2
(45) Date of Patent: Mar. 9, 2021

(54) METHODS AND COMPOSITIONS RELATED TO FUNCTIONAL POLYPEPTIDES EMBEDDED IN HETEROLOGOUS PROTEIN SCAFFOLDS

(71) Applicant: THE SCRIPPS RESEARCH INSTITUTE, La Jolla, CA (US)

(72) Inventors: Yingjie Peng, San Diego, CA (US); Richard A. Lerner, La Jolla, CA (US); Ronald M. Lindsay, Concord, MA (US)

(73) Assignees: The Scripps Research Institute, La Jolla, CA (US); Zebra Biologics, Inc., Concord, MA (US)

( * ) Notice: Subject to any disclaimer, the term of this patent is extended or adjusted under 35 U.S.C. 154(b) by 654 days.

(21) Appl. No.: 15/531,224

(22) PCT Filed: Dec. 1, 2015

(86) PCT No.: PCT/US2015/063126
§ 371 (c)(1),
(2) Date: May 26, 2017

(87) PCT Pub. No.: WO2016/089829
PCT Pub. Date: Jun. 9, 2016

(65) Prior Publication Data
US 2018/0298051 A1    Oct. 18, 2018

Related U.S. Application Data

(60) Provisional application No. 62/222,384, filed on Sep. 23, 2015, provisional application No. 62/085,807, filed on Dec. 1, 2014.

(51) Int. Cl.
*C07K 14/575*    (2006.01)
*C07K 14/64*    (2006.01)
(Continued)

(52) U.S. Cl.
CPC ............. *C07K 14/64* (2013.01); *C07K 1/047* (2013.01); *C07K 14/5759* (2013.01);
(Continued)

(58) Field of Classification Search
CPC combination set(s) only.
See application file for complete search history.

(56) References Cited

U.S. PATENT DOCUMENTS

2011/0243942 A1* 10/2011 Wang ................... C07K 14/64
424/134.1
2013/0288900 A1* 10/2013 Horowitz ........... C12N 15/1037
506/2

FOREIGN PATENT DOCUMENTS

WO    WO-2013106485 A2 *  7/2013  ............. C07K 14/53

OTHER PUBLICATIONS

Metheringham et al. (mAbs, 2009, 1(1):71-85) (Year: 2009).*

* cited by examiner

*Primary Examiner* — Jeremy C Flinders
(74) *Attorney, Agent, or Firm* — Hugh Wang; Thomas Fitting

(57) ABSTRACT

The present invention provides methods for generating functional derivatives of effector polypeptides (e.g., hormones and receptor ligands) embedded in a different protein scaffold (e.g., antibody scaffolds). The methods involve modifying the effector polypeptide with a combinatorial library of terminal linker sequences, inserting the modified sequences into the host scaffold, and then selecting functional derivatives from the library of modified polypeptide sequences embedded in the host scaffold. As exemplifications, the invention also provides specific functional deriva- (Continued)

tives of leptin, scFSH and scRelaxin embedded in an antibody scaffold, as well as therapeutic applications of such functional fusion molecules.

11 Claims, 9 Drawing Sheets

Specification includes a Sequence Listing.

(51) Int. Cl.
*C07K 16/00* (2006.01)
*C40B 40/10* (2006.01)
*C07K 1/04* (2006.01)
*C07K 14/59* (2006.01)
*C07K 16/26* (2006.01)

(52) U.S. Cl.
CPC .............. *C07K 14/59* (2013.01); *C07K 16/00* (2013.01); *C07K 16/26* (2013.01); *C40B 40/10* (2013.01); *C07K 2317/55* (2013.01); *C07K 2317/565* (2013.01); *C07K 2317/622* (2013.01); *C07K 2317/75* (2013.01); *C07K 2317/92* (2013.01); *C07K 2318/10* (2013.01); *C07K 2319/00* (2013.01); *C07K 2319/30* (2013.01); *C07K 2319/35* (2013.01)

| Protein | Clone | N-Linker | Chain a | Inter-linker | Chain b | C-linker |
|---|---|---|---|---|---|---|
| | A2 | LPRGGGGSGGGSGGS | QLYSALANKCCHVGCTKRSLARFC | GSGSGSGS | DSWMEEVIKLCGRELVRAQIAICGMSTWS | SGGGGSLDS |
| Ig1 | A3 | RTRGGSGGS | QLYSALANKCCHVGCTKRSLARFC | GSGSGSGS | DSWMEEVIKLCGRELVRAQIAICGMSTWS | SGGGGSLMS |
| | B5 | QTTGGSGGS | QLYSALANKCCHVGCTKRSLARFC | GSGSGSGS | DSWMEEVIKLCGRELVRAQIAICGMSTWS | SGGGGSKGT |
| Ig2 | C12-2 | RTRGGSGGS | QLYSALANKCCHVGCTKRSLARFC | GSGSGSGS | DSWMEEVIKLCGRELVRAQIAICGMSTWS | SGGGGSKPP |
| Ig3 | C12-1 | PLNGGSGGS | QLYSALANKCCHVGCTKRSLARFC | GSGSGSGS | DSWMEEVIKLCGRELVRAQIAICGMSTWS | SGGGGSKPP |
| | D1 | HMFGGSGGS | QLYSALANKCCHVGCTKRSLARFC | GSGSGSGS | DSWMEEVIKLCGRELVRAQIAICGMSTWS | SGGGGSKAP |
| | D2 | QRGGGSGGS | QLYSALANKCCHVGCTKRSLARFC | GSGSGSGS | DSWMEEVIKLCGRELVRAQIAICGMSTWS | SGGGGWSP |
| | D6 | RQRGGGSGGGSGGS | QLYSALANKCCHVGCTKRSLARFC | GSGSGSGS | DSWMEEVIKLCGRELVRAQIAICGMSTWS | SGGGGSVRA |
| | E9 | RLTGGSGGS | QLYSALANKCCHVGCTKRSLSRFC | GSGSGSGS | DSWMEEVIKLCGRELVRAQIVICGMSTWS | SSGGWSAGGGSGVRS |
| | E10 | RNRGGGGSGGRSGGS | QLYSALANKCCHVGCTKRSLARFC | GSGSGSGS | DSWMEEVIKLCGRELVRAQIAICGMSTWS | SGGGGSGGGGSGGRP |

FIG. 6

SEQUENCE LISTING

```
<160> NUMBER OF SEQ ID NOS: 90

<210> SEQ ID NO 1
<211> LENGTH: 259
<212> TYPE: PRT
<213> ORGANISM: Homo sapiens
```

<400> SEQUENCE: 1

| | | | | | | | | | | | | | | | |
|---|---|---|---|---|---|---|---|---|---|---|---|---|---|---|---|
|Gln|Val|Gln|Leu|Val|Gln|Ser|Gly|Ala|Glu|Val|Lys|Lys|Pro|Gly|Ser|
|1| | | |5| | | | |10| | | | |15| |
|Ser|Val|Lys|Val|Ser|Cys|Lys|Ala|Ser|Gly|Gly|Thr|Phe|Ser|Ser|Tyr|
| | | |20| | | | |25| | | | |30| | |
|Ala|Ile|Ser|Trp|Val|Arg|Gln|Ala|Pro|Gly|Gln|Gly|Leu|Glu|Trp|Met|
| | |35| | | | |40| | | | |45| | | |
|Gly|Gly|Ile|Ile|Pro|Ile|Phe|Gly|Thr|Ala|Asn|Tyr|Ala|Gln|Lys|Phe|
| |50| | | | |55| | | | |60| | | | |
|Gln|Gly|Arg|Val|Thr|Ile|Thr|Ala|Asp|Glu|Ser|Thr|Ser|Thr|Ala|Tyr|
|65| | | | |70| | | | |75| | | | |80|
|Met|Glu|Leu|Ser|Ser|Leu|Arg|Ser|Glu|Asp|Thr|Ala|Val|Tyr|Tyr|Cys|
| | | | |85| | | | |90| | | | |95| |
|Ala|Ser|Gln|Gly|Ile|Leu|Gly|Ile|Thr|Lys|Thr|Ser|Thr|Cys|Tyr|Thr|
| | | |100| | | | |105| | | | |110| | |
|Arg|Val|Met|Asp|Val|Trp|Gly|Gln|Gly|Thr|Thr|Val|Val|Val|Ser|Ser|
| | |115| | | | |120| | | | |125| | | |
|Arg|Ala|Ser|Leu|Gly|Gly|Gly|Ser|Gly|Gly|Gly|Ser|Gly|Gly|Ser|Gly|
| |130| | | | |135| | | | |140| | | | |
|Gly|Gly|Ser|Thr|Gln|Ala|Gly|Leu|Thr|Gln|Pro|Pro|Ser|Val|Ser|Lys|
|145| | | | |150| | | | |155| | | | |160|
|Gly|Leu|Arg|Gln|Thr|Ala|Thr|Leu|Thr|Cys|Thr|Gly|Asn|Ser|Asn|Asn|
| | | | |165| | | | |170| | | | |175| |
|Val|Gly|Asn|Gln|Gly|Ala|Ala|Trp|Leu|Gln|Gln|His|Gln|Gly|His|Pro|
| | | |180| | | | |185| | | | |190| | |
|Pro|Lys|Leu|Leu|Ser|Tyr|Arg|Asn|Asn|Asn|Arg|Pro|Ser|Gly|Ile|Ser|
| | |195| | | | |200| | | | |205| | | |
|Glu|Arg|Leu|Ser|Ala|Ser|Arg|Ser|Gly|Asn|Thr|Ala|Ser|Leu|Thr|Ile|
| |210| | | | |215| | | | |220| | | | |
|Thr|Gly|Leu|Gln|Pro|Glu|Asp|Glu|Ala|Asp|Tyr|Tyr|Cys|Ala|Ala|Trp|
|225| | | | |230| | | | |235| | | | |240|
|Asp|Asp|Ser|Leu|Asn|Gly|Gln|Val|Val|Phe|Gly|Gly|Gly|Thr|Lys|Leu|
| | | | |245| | | | |250| | | | |255| |
|Thr|Val|Leu| | | | | | | | | | | | | |

<210> SEQ ID NO 2
<211> LENGTH: 57
<212> TYPE: DNA
<213> ORGANISM: Artificial Sequence
<220> FEATURE:
<223> OTHER INFORMATION: Synthetic sequence

<400> SEQUENCE: 2
ggatcaggat cgaacgcgac ggggtcaggt tctaatgcaa cttcaggatc gactagt     57

<210> SEQ ID NO 3
<211> LENGTH: 11
<212> TYPE: PRT
<213> ORGANISM: Artificial sequence
<220> FEATURE:
<223> OTHER INFORMATION: Synthetic sequence

<400> SEQUENCE: 3

| | | | | | | | | | | |
|---|---|---|---|---|---|---|---|---|---|---|
|Leu|Gly|Ile|Thr|Lys|Thr|Ser|Thr|Cys|Tyr|Thr|
|1| | | |5| | | | |10| |

```
<210> SEQ ID NO 4
<211> LENGTH: 5
<212> TYPE: PRT
<213> ORGANISM: Artificial Sequence
<220> FEATURE:
<223> OTHER INFORMATION: Synthetic sequence

<400> SEQUENCE: 4

Gly Gly Gly Gly Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic sequence

<400> SEQUENCE: 5

Leu Gly Val Gly Gly Gly Gly Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic sequence

<400> SEQUENCE: 6

Gly Gly Gly Gly Ser Glu Arg Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic sequence

<400> SEQUENCE: 7

His Leu Thr Gly Gly Gly Gly Ser
1               5

<210> SEQ ID NO 8
<211> LENGTH: 13
<212> TYPE: PRT
<213> ORGANISM: Artificial Sequence
<220> FEATURE:
<223> OTHER INFORMATION: Synthetic sequence

<400> SEQUENCE: 8

Gly Ser Gly Gly Ser Gly Gly Gly Gly Ser Asp Pro Ser
1               5                   10

<210> SEQ ID NO 9
<211> LENGTH: 18
<212> TYPE: PRT
<213> ORGANISM: Artificial Sequence
<220> FEATURE:
<223> OTHER INFORMATION: Synthetic sequence

<400> SEQUENCE: 9

Pro Trp Ala Gly Gly Gly Gly Ser Gly Gly Gly Gly Ser Gly Gly Gly
1               5                   10                  15

Gly Ser
```

```
<210> SEQ ID NO 10
<211> LENGTH: 8
<212> TYPE: PRT
<213> ORGANISM: Artificial Sequence
<220> FEATURE:
<223> OTHER INFORMATION: Synthetic sequence

<400> SEQUENCE: 10

Gly Gly Gly Gly Ser Gln Pro Pro
1               5

<210> SEQ ID NO 11
<211> LENGTH: 13
<212> TYPE: PRT
<213> ORGANISM: Artificial Sequence
<220> FEATURE:
<223> OTHER INFORMATION: Synthetic sequence

<400> SEQUENCE: 11

Lys Thr Ser Gly Gly Gly Gly Ser Gly Gly Gly Gly Ser
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Synthetic sequence

<400> SEQUENCE: 12

Gly Gly Gly Gly Ser Ser Asp Glu
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic sequence

<400> SEQUENCE: 13

Lys Val Thr Gly Gly Gly Gly Ser
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic sequence

<400> SEQUENCE: 14

Gly Gly Gly Gly Ser Gln Leu Glu
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic sequence

<400> SEQUENCE: 15

Arg Ser His Gly Gly Gly Gly Ser
1               5
```

```
<210> SEQ ID NO 16
<211> LENGTH: 8
<212> TYPE: PRT
<213> ORGANISM: Artificial Sequence
<220> FEATURE:
<223> OTHER INFORMATION: Synthetic sequence

<400> SEQUENCE: 16

Gly Gly Gly Gly Ser Val Asn Pro
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic sequence

<400> SEQUENCE: 17

Gln Arg Val Gly Gly Gly Gly Ser
1               5

<210> SEQ ID NO 18
<211> LENGTH: 13
<212> TYPE: PRT
<213> ORGANISM: Artificial Sequence
<220> FEATURE:
<223> OTHER INFORMATION: Synthetic sequence

<400> SEQUENCE: 18

Gly Gly Gly Gly Ser Gly Gly Gly Gly Ser Arg Ser Ala
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic sequence

<400> SEQUENCE: 19

Arg Val Leu Gly Gly Gly Gly Ser
1               5

<210> SEQ ID NO 20
<211> LENGTH: 13
<212> TYPE: PRT
<213> ORGANISM: Artificial Sequence
<220> FEATURE:
<223> OTHER INFORMATION: Synthetic sequence

<400> SEQUENCE: 20

Gly Gly Gly Gly Ser Gly Gly Gly Gly Ser Gln Ser Ser
1               5                   10

<210> SEQ ID NO 21
<211> LENGTH: 95
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (14)..(20)
<223> OTHER INFORMATION: "N" is "A" or "G"
<220> FEATURE:
<221> NAME/KEY: misc_feature
<222> LOCATION: (145)..(21)
<223> OTHER INFORMATION: K is G or T
```

```
<400> SEQUENCE: 21
gcgagaggga tccnknnknn kggcggtggc gggtctggtg gaggtggaag cggaggtgga    60
gggagtgtgc ccatccaaaa agtccaagat gacac                              95

<210> SEQ ID NO 22
<211> LENGTH: 80
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (14)..(20)
<223> OTHER INFORMATION: N is A or G or C or T
<220> FEATURE:
<221> NAME/KEY: misc_feature
<222> LOCATION: (15)..(21)
<223> OTHER INFORMATION: K is G or T

<400> SEQUENCE: 22
gcgagaggga tccnknnknn kggtggaggt ggaagcggag gtggagggag tgtgcccatc    60
caaaaagtcc aagatgacac                                               80

<210> SEQ ID NO 23
<211> LENGTH: 65
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (14)..(20)
<223> OTHER INFORMATION: N is A or G or C or T
<220> FEATURE:
<221> NAME/KEY: misc_feature
<222> LOCATION: (15)..(21)
<223> OTHER INFORMATION: K is G or T

<400> SEQUENCE: 23
gcgagaggga tccnknnknn kggaggtgga gggagtgtgc ccatccaaaa agtccaagat    60
gacac                                                               65

<210> SEQ ID NO 24
<211> LENGTH: 88
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (15)..(21)
<223> OTHER INFORMATION: N is A or G or C or T
<220> FEATURE:
<221> NAME/KEY: misc_feature
<222> LOCATION: (16)..(19)
<223> OTHER INFORMATION: M is A or C

<400> SEQUENCE: 24
gtccattacc cgggnmnnmn nggacccacc acctccactc ccacctccgc cactacctcc    60
gccaccgcac ccagggctga ggtccagc                                      88

<210> SEQ ID NO 25
<211> LENGTH: 73
<212> TYPE: DNA
<213> ORGANISM: Artificial Sequence
<220> FEATURE:
<223> OTHER INFORMATION: Synthetic sequence
```

```
<220> FEATURE:
<221> NAME/KEY: misc_feature
<222> LOCATION: (15)..(21)
<223> OTHER INFORMATION: N is A or G or C or T
<220> FEATURE:
<221> NAME/KEY: misc_feature
<222> LOCATION: (16)..(19)
<223> OTHER INFORMATION: M is A or C

<400> SEQUENCE: 25
gtccattacc cgggnmnnnmn nactcccacc tccgccacta cctccgccac cgcacccagg      60
gctgaggtcc agc                                                         73

<210> SEQ ID NO 26
<211> LENGTH: 58
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (15)..(21)
<223> OTHER INFORMATION: N is A or G
<220> FEATURE:
<221> NAME/KEY: misc_feature
<222> LOCATION: (16)..(19)
<223> OTHER INFORMATION: M is A or C

<400> SEQUENCE: 26
gtccattacc cgggnmnnnmn nactacctcc gccaccgcac ccagggctga ggtccagc        58

<210> SEQ ID NO 27
<211> LENGTH: 97
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (14)..(20)
<223> OTHER INFORMATION: N is A or G or C or T
<220> FEATURE:
<221> NAME/KEY: misc_feature
<222> LOCATION: (15)..(21)
<223> OTHER INFORMATION: K is G or T

<400> SEQUENCE: 27
gcgagaggga tccnknnknn kggcggtggc gggtctggtg gaggtggaag cggaggtgga      60
gggagtaata gctgtgagct gaccaacatc accattg                              97

<210> SEQ ID NO 28
<211> LENGTH: 82
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (14)..(20)
<223> OTHER INFORMATION: N is A or G or C or T
<220> FEATURE:
<221> NAME/KEY: misc_feature
<222> LOCATION: (15)..(21)
<223> OTHER INFORMATION: K is G or T

<400> SEQUENCE: 28
gcgagaggga tccnknnknn kggtggaggt ggaagcggag gtggagggag taatagctgt      60
gagctgacca acatcaccat tg                                               82
```

```
<210> SEQ ID NO 29
<211> LENGTH: 67
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (14)..(20)
<223> OTHER INFORMATION: N is A or G or C or T
<220> FEATURE:
<221> NAME/KEY: misc_feature
<222> LOCATION: (15)..(21)
<223> OTHER INFORMATION: K is G or T

<400> SEQUENCE: 29
gcgagaggga tccnknnknn kggaggtgga gggagtaata gctgtgagct gaccaacatc    60
accattg                                                             67

<210> SEQ ID NO 30
<211> LENGTH: 96
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (15)..(21)
<223> OTHER INFORMATION: N is A or G or C or T
<220> FEATURE:
<221> NAME/KEY: misc_feature
<222> LOCATION: (16)..(19)
<223> OTHER INFORMATION: M is A or C

<400> SEQUENCE: 30
gtccattacc cgggnmnnmn nggacccacc acctccactc ccacctccgc cactacctcc    60
gccaccgctc ttgtggtagt agcaggtgct gcagtg                             96

<210> SEQ ID NO 31
<211> LENGTH: 81
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (15)..(21)
<223> OTHER INFORMATION: N is A or G or C or T
<220> FEATURE:
<221> NAME/KEY: misc_feature
<222> LOCATION: (16)..(19)
<223> OTHER INFORMATION: M is A or C

<400> SEQUENCE: 31
gtccattacc cgggnmnnmn nactcccacc tccgccacta cctccgccac cgctcttgtg    60
gtagtagcag gtgctgcagt g                                             81

<210> SEQ ID NO 32
<211> LENGTH: 66
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (15)..(21)
<223> OTHER INFORMATION: N is A or G or C or T
```

```
<220> FEATURE:
<221> NAME/KEY: misc_feature
<222> LOCATION: (16)..(19)
<223> OTHER INFORMATION: M is A or C

<400> SEQUENCE: 32
gtccattacc cgggnmnnmn nactacctcc gccaccgctc ttgtggtagt agcaggtgct    60
gcagtg                                                              66

<210> SEQ ID NO 33
<211> LENGTH: 19
<212> TYPE: PRT
<213> ORGANISM: Artificial Sequence
<220> FEATURE:
<223> OTHER INFORMATION: Synthetic sequence

<400> SEQUENCE: 33

Gly Ser Gly Ser Asn Ala Thr Gly Ser Gly Ser Asn Ala Thr Ser Gly
1               5                   10                  15

Ser Thr Ser

<210> SEQ ID NO 34
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (6)..(15)
<223> OTHER INFORMATION: residues 6-10 and/or 11-15 can either be all
      present or all absent

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 18
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(3)
<223> OTHER INFORMATION: Xaa can be any amino acid residue
<220> FEATURE:
<221> NAME/KEY: MISC_FEATURE
<222> LOCATION: (9)..(18)
<223> OTHER INFORMATION: residues 9-13 and/or 14-18 can be either all
      present or all absent

<400> SEQUENCE: 35

Xaa Xaa Xaa Gly Gly Gly Gly Ser Gly Gly Gly Gly Ser Gly Gly Gly
1               5                   10                  15

Gly Ser

<210> SEQ ID NO 36
<211> LENGTH: 18
<212> TYPE: PRT
<213> ORGANISM: Artificial Sequence
<220> FEATURE:
<223> OTHER INFORMATION: Synthetic sequence
```

```
<220> FEATURE:
<221> NAME/KEY: MISC_FEATURE
<222> LOCATION: (1)..(15)
<223> OTHER INFORMATION: residues 6-10 and/or 11-15 can be either all
      present or all absent
<220> FEATURE:
<221> NAME/KEY: MISC_FEATURE
<222> LOCATION: (16)..(18)
<223> OTHER INFORMATION: Xaa can be any amino acid residue

<400> SEQUENCE: 36

Gly Gly Gly Gly Ser Gly Gly Gly Gly Ser Gly Gly Gly Gly Ser Xaa
1               5                   10                  15

Xaa Xaa

<210> SEQ ID NO 37
<211> LENGTH: 8
<212> TYPE: PRT
<213> ORGANISM: Artificial Sequence
<220> FEATURE:
<223> OTHER INFORMATION: Synthetic sequence

<400> SEQUENCE: 37

Arg His Met Gly Gly Gly Gly Ser
1               5

<210> SEQ ID NO 38
<211> LENGTH: 13
<212> TYPE: PRT
<213> ORGANISM: Artificial Sequence
<220> FEATURE:
<223> OTHER INFORMATION: Synthetic sequence

<400> SEQUENCE: 38

Gly Gly Gly Gly Ser Gly Gly Gly Gly Ser Thr Asp Thr
1               5                   10

<210> SEQ ID NO 39
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (2)..(5)
<223> OTHER INFORMATION: Xaa can be any amino acid residue

<400> SEQUENCE: 39

Gly Xaa Gly Xaa Xaa Gly
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic sequence

<400> SEQUENCE: 40

Leu Gly Val Gly Gly Gly Ser
1               5

<210> SEQ ID NO 41
<211> LENGTH: 8
<212> TYPE: PRT
<213> ORGANISM: Artificial Sequence
```

```
<220> FEATURE:
<223> OTHER INFORMATION: Synthetic sequence

<400> SEQUENCE: 41

Ile Gly Val Gly Gly Gly Gly Ser
1               5

<210> SEQ ID NO 42
<211> LENGTH: 24
<212> TYPE: PRT
<213> ORGANISM: Homo sapiens

<400> SEQUENCE: 42

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 43
<211> LENGTH: 29
<212> TYPE: PRT
<213> ORGANISM: Homo sapiens

<400> SEQUENCE: 43

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 44
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (7)..(10)
<223> OTHER INFORMATION: residues 7-8 and/or 9-10 can be either all
      present or all absent

<400> SEQUENCE: 44

Gly Ser Gly Ser Gly Ser Gly Ser Gly Ser
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Synthetic sequence

<400> SEQUENCE: 45

Gly Ser Gly Ser Gly Ser Gly Ser
1               5

<210> SEQ ID NO 46
<211> LENGTH: 12
<212> TYPE: PRT
<213> ORGANISM: Artificial Sequence
<220> FEATURE:
<223> OTHER INFORMATION: Synthetic sequence

<400> SEQUENCE: 46

Gly Gly Gly Gly Ser Gly Gly Gly Ser Gly Gly Ser
1               5                   10
```

```
<210> SEQ ID NO 47
<211> LENGTH: 6
<212> TYPE: PRT
<213> ORGANISM: Artificial Sequence
<220> FEATURE:
<223> OTHER INFORMATION: Synthetic sequence

<400> SEQUENCE: 47

Gly Gly Ser Gly Gly Ser
1               5

<210> SEQ ID NO 48
<211> LENGTH: 12
<212> TYPE: PRT
<213> ORGANISM: Artificial Sequence
<220> FEATURE:
<223> OTHER INFORMATION: Synthetic sequence

<400> SEQUENCE: 48

Ser Gly Gly Gly Gly Ser Gly Gly Gly Gly Ser Gly
1               5                   10

<210> SEQ ID NO 49
<211> LENGTH: 6
<212> TYPE: PRT
<213> ORGANISM: Artificial Sequence
<220> FEATURE:
<223> OTHER INFORMATION: Synthetic sequence

<400> SEQUENCE: 49

Ser Gly Gly Gly Gly Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic sequence

<400> SEQUENCE: 50

Arg Thr Arg Gly Gly Ser Gly Gly Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic sequence

<400> SEQUENCE: 51

Ser Gly Gly Gly Gly Ser Leu Met Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic sequence

<400> SEQUENCE: 52

Ser Gly Gly Gly Gly Ser Lys Pro Pro
1               5
```

```
<210> SEQ ID NO 53
<211> LENGTH: 9
<212> TYPE: PRT
<213> ORGANISM: Artificial Sequence
<220> FEATURE:
<223> OTHER INFORMATION: Synthetic sequence

<400> SEQUENCE: 53

Pro Leu Asn Gly Gly Ser Gly Gly Ser
1               5

<210> SEQ ID NO 54
<211> LENGTH: 15
<212> TYPE: PRT
<213> ORGANISM: Artificial Sequence
<220> FEATURE:
<223> OTHER INFORMATION: Synthetic sequence

<400> SEQUENCE: 54

Leu Pro Arg Gly Gly Gly Gly Ser Gly Gly Gly Ser Gly Gly Ser
1               5                   10                  15

<210> SEQ ID NO 55
<211> LENGTH: 9
<212> TYPE: PRT
<213> ORGANISM: Artificial Sequence
<220> FEATURE:
<223> OTHER INFORMATION: Synthetic sequence

<400> SEQUENCE: 55

Ser Gly Gly Gly Gly Ser Leu Asp Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic sequence

<400> SEQUENCE: 56

Gln Thr Thr Gly Gly Ser Gly Gly Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic sequence

<400> SEQUENCE: 57

Ser Gly Gly Gly Gly Ser Lys Gly Thr
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic sequence

<400> SEQUENCE: 58

His Met Phe Gly Gly Ser Gly Gly Ser
1               5
```

```
<210> SEQ ID NO 59
<211> LENGTH: 9
<212> TYPE: PRT
<213> ORGANISM: Artificial Sequence
<220> FEATURE:
<223> OTHER INFORMATION: Synthetic sequence

<400> SEQUENCE: 59

Ser Gly Gly Gly Gly Ser Lys Ala Pro
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic sequence

<400> SEQUENCE: 60

Gln Arg Gly Gly Gly Ser Gly Gly Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic sequence

<400> SEQUENCE: 61

Ser Gly Gly Gly Gly Ser Trp Ser Pro
1               5

<210> SEQ ID NO 62
<211> LENGTH: 15
<212> TYPE: PRT
<213> ORGANISM: Artificial Sequence
<220> FEATURE:
<223> OTHER INFORMATION: Synthetic sequence

<400> SEQUENCE: 62

Arg Gln Arg Gly Gly Gly Gly Ser Gly Gly Gly Ser Gly Gly Ser
1               5                   10                  15

<210> SEQ ID NO 63
<211> LENGTH: 9
<212> TYPE: PRT
<213> ORGANISM: Artificial Sequence
<220> FEATURE:
<223> OTHER INFORMATION: Synthetic sequence

<400> SEQUENCE: 63

Ser Gly Gly Gly Gly Ser Val Arg Ala
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic sequence

<400> SEQUENCE: 64

Arg Leu Thr Gly Gly Ser Gly Gly Ser
1               5
```

```
<210> SEQ ID NO 65
<211> LENGTH: 15
<212> TYPE: PRT
<213> ORGANISM: Artificial Sequence
<220> FEATURE:
<223> OTHER INFORMATION: Synthetic sequence

<400> SEQUENCE: 65

Ser Ser Gly Gly Trp Ser Ala Gly Gly Ser Gly Val Arg Ser
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic sequence

<400> SEQUENCE: 66

Arg Asn Arg Gly Gly Gly Gly Ser Gly Gly Arg Ser Gly Gly Ser
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic sequence

<400> SEQUENCE: 67

Ser Gly Gly Gly Gly Ser Gly Gly Gly Ser Gly Gly Arg Pro
1               5                   10                  15

<210> SEQ ID NO 68
<211> LENGTH: 85
<212> TYPE: PRT
<213> ORGANISM: Artificial Sequence
<220> FEATURE:
<223> OTHER INFORMATION: Synthetic sequence

<400> SEQUENCE: 68

Leu Pro Arg Gly Gly Gly Gly Ser Gly Gly Ser Gly Gly Ser Gln
1               5                   10                  15

Leu Tyr Ser Ala Leu Ala Asn Lys Cys Cys His Val Gly Cys Thr Lys
                20                  25                  30

Arg Ser Leu Ala Arg Phe Cys Gly Ser Gly Ser Gly Ser Gly Ser Asp
        35                  40                  45

Ser Trp Met Glu Glu Val Ile Lys Leu Cys Gly Arg Glu Leu Val Arg
        50                  55                  60

Ala Gln Ile Ala Ile Cys Gly Met Ser Thr Trp Ser Ser Gly Gly
65                  70                  75                  80

Gly Ser Leu Asp Ser
                85

<210> SEQ ID NO 69
<211> LENGTH: 79
<212> TYPE: PRT
<213> ORGANISM: Artificial Sequence
<220> FEATURE:
<223> OTHER INFORMATION: Synthetic sequence
```

<400> SEQUENCE: 69

Arg Thr Arg Gly Gly Ser Gly Gly Ser Gln Leu Tyr Ser Ala Leu Ala
1               5                   10                  15

Asn Lys Cys Cys His Val Gly Cys Thr Lys Arg Ser Leu Ala Arg Phe
            20                  25                  30

Cys Gly Ser Gly Ser Gly Ser Gly Ser Asp Ser Trp Met Glu Glu Val
        35                  40                  45

Ile Lys Leu Cys Gly Arg Glu Leu Val Arg Ala Gln Ile Ala Ile Cys
    50                  55                  60

Gly Met Ser Thr Trp Ser Ser Gly Gly Gly Ser Leu Met Ser
65                  70                  75

<210> SEQ ID NO 70
<211> LENGTH: 79
<212> TYPE: PRT
<213> ORGANISM: Artificial Sequence
<220> FEATURE:
<223> OTHER INFORMATION: Synthetic sequence

<400> SEQUENCE: 70

Gln Thr Thr Gly Gly Ser Gly Gly Ser Gln Leu Tyr Ser Ala Leu Ala
1               5                   10                  15

Asn Lys Cys Cys His Val Gly Cys Thr Lys Arg Ser Leu Ala Arg Phe
            20                  25                  30

Cys Gly Ser Gly Ser Gly Ser Gly Ser Asp Ser Trp Met Glu Glu Val
        35                  40                  45

Ile Lys Leu Cys Gly Arg Glu Leu Val Arg Ala Gln Ile Ala Ile Cys
    50                  55                  60

Gly Met Ser Thr Trp Ser Ser Gly Gly Gly Ser Lys Gly Thr
65                  70                  75

<210> SEQ ID NO 71
<211> LENGTH: 79
<212> TYPE: PRT
<213> ORGANISM: Artificial Sequence
<220> FEATURE:
<223> OTHER INFORMATION: Synthetic sequence

<400> SEQUENCE: 71

Arg Thr Arg Gly Gly Ser Gly Gly Ser Gln Leu Tyr Ser Ala Leu Ala
1               5                   10                  15

Asn Lys Cys Cys His Val Gly Cys Thr Lys Arg Ser Leu Ala Arg Phe
            20                  25                  30

Cys Gly Ser Gly Ser Gly Ser Gly Ser Asp Ser Trp Met Glu Glu Val
        35                  40                  45

Ile Lys Leu Cys Gly Arg Glu Leu Val Arg Ala Gln Ile Ala Ile Cys
    50                  55                  60

Gly Met Ser Thr Trp Ser Ser Gly Gly Gly Ser Lys Pro Pro
65                  70                  75

<210> SEQ ID NO 72
<211> LENGTH: 79
<212> TYPE: PRT
<213> ORGANISM: Artificial Sequence
<220> FEATURE:
<223> OTHER INFORMATION: Synthetic sequence

<400> SEQUENCE: 72

Pro Leu Asn Gly Gly Ser Gly Gly Ser Gln Leu Tyr Ser Ala Leu Ala
1               5                   10                  15

Asn Lys Cys Cys His Val Gly Cys Thr Lys Arg Ser Leu Ala Arg Phe
            20                  25                  30

Cys Gly Ser Gly Ser Gly Ser Gly Ser Asp Ser Trp Met Glu Glu Val
        35                  40                  45

Ile Lys Leu Cys Gly Arg Glu Leu Val Arg Ala Gln Ile Ala Ile Cys
    50                  55                  60

Gly Met Ser Thr Trp Ser Ser Gly Gly Gly Ser Lys Pro Pro
65                  70                  75

<210> SEQ ID NO 73
<211> LENGTH: 79
<212> TYPE: PRT
<213> ORGANISM: Artificial Sequence
<220> FEATURE:
<223> OTHER INFORMATION: Synthetic sequence

<400> SEQUENCE: 73

His Met Phe Gly Gly Ser Gly Gly Ser Gln Leu Tyr Ser Ala Leu Ala
1               5                   10                  15

Asn Lys Cys Cys His Val Gly Cys Thr Lys Arg Ser Leu Ala Arg Phe
            20                  25                  30

Cys Gly Ser Gly Ser Gly Ser Gly Ser Asp Ser Trp Met Glu Glu Val
        35                  40                  45

Ile Lys Leu Cys Gly Arg Glu Leu Val Arg Ala Gln Ile Ala Ile Cys
    50                  55                  60

Gly Met Ser Thr Trp Ser Ser Gly Gly Gly Ser Lys Ala Pro
65                  70                  75

<210> SEQ ID NO 74
<211> LENGTH: 79
<212> TYPE: PRT
<213> ORGANISM: Artificial Sequence
<220> FEATURE:
<223> OTHER INFORMATION: Synthetic sequence

<400> SEQUENCE: 74

Gln Arg Gly Gly Gly Ser Gly Gly Ser Gln Leu Tyr Ser Ala Leu Ala
1               5                   10                  15

Asn Lys Cys Cys His Val Gly Cys Thr Lys Arg Ser Leu Ala Arg Phe
            20                  25                  30

Cys Gly Ser Gly Ser Gly Ser Gly Ser Asp Ser Trp Met Glu Glu Val
        35                  40                  45

Ile Lys Leu Cys Gly Arg Glu Leu Val Arg Ala Gln Ile Ala Ile Cys
    50                  55                  60

Gly Met Ser Thr Trp Ser Ser Gly Gly Gly Ser Trp Ser Pro
65                  70                  75

<210> SEQ ID NO 75
<211> LENGTH: 85
<212> TYPE: PRT
<213> ORGANISM: Artificial Sequence
<220> FEATURE:
<223> OTHER INFORMATION: Synthetic sequence

<400> SEQUENCE: 75

Arg Gln Arg Gly Gly Gly Ser Gly Gly Ser Gly Gly Ser Gln
1               5                   10                  15

Leu Tyr Ser Ala Leu Ala Asn Lys Cys Cys His Val Gly Cys Thr Lys
            20                  25                  30

Arg Ser Leu Ala Arg Phe Cys Gly Ser Gly Ser Gly Ser Gly Ser Asp
        35                  40                  45

Ser Trp Met Glu Glu Val Ile Lys Leu Cys Gly Arg Glu Leu Val Arg
    50                  55                  60

Ala Gln Ile Ala Ile Cys Gly Met Ser Thr Trp Ser Ser Gly Gly Gly
65                  70                  75                  80

Gly Ser Val Arg Ala
                85

<210> SEQ ID NO 76
<211> LENGTH: 85
<212> TYPE: PRT
<213> ORGANISM: Artificial Sequence
<220> FEATURE:
<223> OTHER INFORMATION: Synthetic sequence

<400> SEQUENCE: 76

Arg Leu Thr Gly Gly Ser Gly Gly Ser Gln Leu Tyr Ser Ala Leu Ala
1               5                   10                  15

Asn Lys Cys Cys His Val Gly Cys Thr Lys Arg Ser Leu Ser Arg Phe
            20                  25                  30

Cys Gly Ser Gly Ser Gly Ser Asp Ser Trp Met Glu Glu Val
        35                  40                  45

Ile Lys Leu Cys Gly Arg Glu Leu Val Arg Ala Gln Ile Val Ile Cys
    50                  55                  60

Gly Met Ser Thr Trp Ser Ser Gly Gly Trp Ser Ala Gly Gly Gly
65                  70                  75                  80

Ser Gly Val Arg Ser
                85

<210> SEQ ID NO 77
<211> LENGTH: 91
<212> TYPE: PRT
<213> ORGANISM: Artificial Sequence
<220> FEATURE:
<223> OTHER INFORMATION: Synthetic sequence

<400> SEQUENCE: 77

Arg Asn Arg Gly Gly Gly Ser Gly Gly Arg Ser Gly Gly Ser Gln
1               5                   10                  15

Leu Tyr Ser Ala Leu Ala Asn Lys Cys Cys His Val Gly Cys Thr Lys
            20                  25                  30

Arg Ser Leu Ala Arg Phe Cys Gly Ser Gly Ser Gly Ser Gly Ser Asp
        35                  40                  45

Ser Trp Met Glu Glu Val Ile Lys Leu Cys Gly Arg Glu Leu Val Arg
    50                  55                  60

Ala Gln Ile Ala Ile Cys Gly Met Ser Thr Trp Ser Ser Gly Gly Gly
65                  70                  75                  80

Gly Ser Gly Gly Gly Gly Ser Gly Gly Arg Pro
                85                  90

```
<210> SEQ ID NO 78
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(3)
<223> OTHER INFORMATION: Xaa can be any amino acid residue

<400> SEQUENCE: 78

Xaa Xaa Xaa Gly Gly Gly Gly Ser Gly Gly Gly Ser Gly Gly Ser
1               5                   10                  15

<210> SEQ ID NO 79
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(3)
<223> OTHER INFORMATION: Xaa can be any amino acid residue

<400> SEQUENCE: 79

Xaa Xaa Xaa Gly Gly Ser Gly Gly Ser
1               5

<210> SEQ ID NO 80
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (13)..(15)
<223> OTHER INFORMATION: Xaa can be any amino acid residue

<400> SEQUENCE: 80

Ser Gly Gly Gly Gly Ser Gly Gly Gly Gly Ser Gly Xaa Xaa Xaa
1               5                   10                  15

<210> SEQ ID NO 81
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (7)..(9)
<223> OTHER INFORMATION: Xaa can be any amino acid residue

<400> SEQUENCE: 81

Ser Gly Gly Gly Gly Ser Xaa Xaa Xaa
1               5

<210> SEQ ID NO 82
<211> LENGTH: 28
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(4)
<223> OTHER INFORMATION: Xaa can be any amino acid residue
```

```
<220> FEATURE:
<221> NAME/KEY: MISC_FEATURE
<222> LOCATION: (3)..(4)
<223> OTHER INFORMATION: any one or both of residues 3 and 4 can be
      either present or absent
<220> FEATURE:
<221> NAME/KEY: MISC_FEATURE
<222> LOCATION: (3)..(4)
<223> OTHER INFORMATION: residues 10-14 can be either all present or all
      absent
<220> FEATURE:
<221> NAME/KEY: MISC_FEATURE
<222> LOCATION: (15)..(22)
<223> OTHER INFORMATION: residues 15-18 and/or 19-22 can be either all
      present or all absent
<220> FEATURE:
<221> NAME/KEY: MISC_FEATURE
<222> LOCATION: (23)..(28)
<223> OTHER INFORMATION: residues 23-25 and/or 26-28 can be either all
      present or all absent

<400> SEQUENCE: 82

Xaa Xaa Xaa Xaa Gly Gly Gly Gly Ser Gly Gly Gly Gly Ser Gly Gly
1               5                   10                  15

Gly Ser Gly Gly Gly Ser Gly Gly Ser Gly Gly Ser
            20                  25

<210> SEQ ID NO 83
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(4)
<223> OTHER INFORMATION: Xaa can be any amino acid residue
<220> FEATURE:
<221> NAME/KEY: MISC_FEATURE
<222> LOCATION: (3)..(4)
<223> OTHER INFORMATION: one or both of residues 3 and 4 can be either
      present or absent
<220> FEATURE:
<221> NAME/KEY: MISC_FEATURE
<222> LOCATION: (8)..(13)
<223> OTHER INFORMATION: residues 8-10 and/or 11-13 can be either all
      present or all absent

<400> SEQUENCE: 83

Xaa Xaa Xaa Xaa Gly Gly Ser Gly Gly Ser Gly Gly Ser
1               5                   10

<210> SEQ ID NO 84
<211> LENGTH: 18
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (6)..(10)
<223> OTHER INFORMATION: residues 6-10 are either all present or all
      absent
<220> FEATURE:
<221> NAME/KEY: MISC_FEATURE
<222> LOCATION: (11)..(14)
<223> OTHER INFORMATION: residues 11-12 and/or 13-14 are either all
      present or all absent
<220> FEATURE:
<221> NAME/KEY: MISC_FEATURE
<222> LOCATION: (15)..(18)
<223> OTHER INFORMATION: Xaa can be any amino acid residue
```

```
<220> FEATURE:
<221> NAME/KEY: MISC_FEATURE
<222> LOCATION: (17)..(18)
<223> OTHER INFORMATION: one or both of residues 17 and 18 can be either
      present or absent

<400> SEQUENCE: 84

Ser Gly Gly Gly Gly Ser Gly Gly Gly Gly Ser Gly Ser Gly Xaa Xaa
1               5                   10                  15

Xaa Xaa

<210> SEQ ID NO 85
<211> LENGTH: 16
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (6)..(10)
<223> OTHER INFORMATION: residues 6-10 are either all present or all
      absent
<220> FEATURE:
<221> NAME/KEY: MISC_FEATURE
<222> LOCATION: (11)..(12)
<223> OTHER INFORMATION: one or both of residues 11 and 12 can be either
      present or absent
<220> FEATURE:
<221> NAME/KEY: MISC_FEATURE
<222> LOCATION: (13)..(16)
<223> OTHER INFORMATION: Xaa can be any amino acid residue
<220> FEATURE:
<221> NAME/KEY: MISC_FEATURE
<222> LOCATION: (15)..(16)
<223> OTHER INFORMATION: one or both of residues 15 and 16 can be either
      present or absent

<400> SEQUENCE: 85

Ser Gly Gly Gly Gly Ser Gly Gly Gly Gly Ser Ser Xaa Xaa Xaa Xaa
1               5                   10                  15

<210> SEQ ID NO 86
<211> LENGTH: 53
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: Xaa can be any amino acid residue
<220> FEATURE:
<221> NAME/KEY: MISC_FEATURE
<222> LOCATION: (2)..(5)
<223> OTHER INFORMATION: each of residues 2-5 can be either present or
      absent
<220> FEATURE:
<221> NAME/KEY: MISC_FEATURE
<222> LOCATION: (6)..(53)
<223> OTHER INFORMATION: Residues 6-13, residues 14-21, residues 22-29,
      residues 30-37, residues 38-45 and residues 46-53 are identical
      sequence segments.  Each residue in the identical segments can be
      either present or absent.
<220> FEATURE:
<221> NAME/KEY: MISC_FEATURE
<222> LOCATION: (14)..(53)
<223> OTHER INFORMATION: residues 22-29, residues 30-37, residues 38-45
      and/or residues 46-53 can be either all present or all absent.
```

```
<400> SEQUENCE: 86

Xaa Xaa Xaa Xaa Xaa Gly Gly Gly Gly Gly Ser Ser Gly Gly Gly
1               5                   10                  15

Gly Gly Gly Ser Ser Gly Gly Gly Gly Gly Ser Ser Gly Gly Gly
                20                  25                  30

Gly Gly Gly Ser Ser Gly Gly Gly Gly Gly Ser Ser Gly Gly Gly
                35                  40                  45

Gly Gly Gly Ser Ser
            50

<210> SEQ ID NO 87
<211> LENGTH: 53
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: Xaa can be any amino acid residue
<220> FEATURE:
<221> NAME/KEY: MISC_FEATURE
<222> LOCATION: (2)..(5)
<223> OTHER INFORMATION: each of residues 2-5 can be either present or
      absent
<220> FEATURE:
<221> NAME/KEY: MISC_FEATURE
<222> LOCATION: (6)..(53)
<223> OTHER INFORMATION: Residues 6-13, residues 14-21, residues 22-29,
      residues 30-37, residues 38-45 and residues 46-53 are identical
      sequence segments.  Each residue in the identical segments can be
      either present or absent.
<220> FEATURE:
<221> NAME/KEY: MISC_FEATURE
<222> LOCATION: (14)..(53)
<223> OTHER INFORMATION: residues 14-21, residues 22-29, residues 30-37,
      residues 38-45 and/or residues 46-53 can be either all present or
      all absent.

<400> SEQUENCE: 87

Xaa Xaa Xaa Xaa Xaa Ser Ser Gly Gly Gly Gly Gly Gly Ser Ser Gly
1               5                   10                  15

Gly Gly Gly Gly Gly Ser Ser Gly Gly Gly Gly Gly Gly Ser Ser Gly
                20                  25                  30

Gly Gly Gly Gly Gly Ser Ser Gly Gly Gly Gly Gly Gly Ser Ser Gly
                35                  40                  45

Gly Gly Gly Gly Gly
            50

<210> SEQ ID NO 88
<211> LENGTH: 53
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(48)
<223> OTHER INFORMATION: Residues 1-8, residues 9-16, residues 17-24,
      residues 25-32, residues 33-40 and residues 41-48 are identical
      sequence segments.  Each residue in the identical segments can be
      either present or absent.
<220> FEATURE:
<221> NAME/KEY: MISC_FEATURE
<222> LOCATION: (9)..(48)
<223> OTHER INFORMATION: residues 9-16, residues 17-24, residues 25-32,
      residues 33-40 and/or residues 41-48 can be either all present or
      all absent.
```

```
<220> FEATURE:
<221> NAME/KEY: MISC_FEATURE
<222> LOCATION: (49)..(53)
<223> OTHER INFORMATION: Xaa can be any amino acid residue
<220> FEATURE:
<221> NAME/KEY: MISC_FEATURE
<222> LOCATION: (50)..(53)
<223> OTHER INFORMATION: each of residues 50-53 can be either present or
      absent

<400> SEQUENCE: 88

Gly Gly Gly Gly Gly Gly Ser Ser Gly Gly Gly Gly Gly Gly Ser Ser
1               5                   10                  15

Gly Gly Gly Gly Gly Gly Ser Ser Gly Gly Gly Gly Gly Gly Ser Ser
            20                  25                  30

Gly Gly Gly Gly Gly Gly Ser Ser Gly Gly Gly Gly Gly Gly Ser Ser
        35                  40                  45

Xaa Xaa Xaa Xaa Xaa
    50

<210> SEQ ID NO 89
<211> LENGTH: 53
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(48)
<223> OTHER INFORMATION: Residues 1-8, residues 9-16, residues 17-24,
      residues 25-32, residues 33-40 and residues 41-48 are identical
      sequence segments.  Each residue in the identical segments can be
      either present or absent.
<220> FEATURE:
<221> NAME/KEY: MISC_FEATURE
<222> LOCATION: (9)..(48)
<223> OTHER INFORMATION: residues 9-16, residues 17-24, residues 25-32,
      residues 33-40 and/or residues 41-48 can be either all present or
      all absent.
<220> FEATURE:
<221> NAME/KEY: MISC_FEATURE
<222> LOCATION: (49)..(53)
<223> OTHER INFORMATION: Xaa can be any amino acid residue
<220> FEATURE:
<221> NAME/KEY: MISC_FEATURE
<222> LOCATION: (50)..(53)
<223> OTHER INFORMATION: each of residues 50-53 can be either present or
      absent

<400> SEQUENCE: 89

Ser Ser Gly Gly Gly Gly Gly Gly Ser Ser Gly Gly Gly Gly Gly Gly
1               5                   10                  15

Ser Ser Gly Gly Gly Gly Gly Gly Ser Ser Gly Gly Gly Gly Gly Gly
            20                  25                  30

Ser Ser Gly Gly Gly Gly Gly Gly Ser Ser Gly Gly Gly Gly Gly Gly
        35                  40                  45

Xaa Xaa Xaa Xaa Xaa
    50

<210> SEQ ID NO 90
<211> LENGTH: 6
<212> TYPE: PRT
<213> ORGANISM: Artificial Sequence
<220> FEATURE:
<223> OTHER INFORMATION: Synthetic sequence
```

```
<400> SEQUENCE: 90

Arg Val Gly Gly Gly
1               5
```

METHODS AND COMPOSITIONS RELATED TO FUNCTIONAL POLYPEPTIDES EMBEDDED IN HETEROLOGOUS PROTEIN SCAFFOLDS

CROSS-REFERENCE TO RELATED APPLICATIONS

The subject patent application claims the benefit of priority to U.S. Provisional Patent Application Nos. 62/085,807 (filed Dec. 1, 2014) and 62/222,384 (filed Sep. 23, 2015). The full disclosures of the priority applications are incorporated herein by reference in their entirety and for all purposes.

BACKGROUND OF THE INVENTION

Functional proteins or polypeptides (e.g., hormones) often need to be modified in order to provide more desired biological characteristics, e.g., improved stability, pharmacokinetic or pharmacological properties. Essentially a protein can be considered to be an ensemble of secondary structure folds connected to each other by N and C-terminal junctions. Because of advances in protein structure determination, there is now a large and ever-growing menu of secondary structure folds in proteins. Thus, new functional polypeptides may be modified by inserting some of these secondary structure elements (guests) into a new protein partner (host). There are problems associated with such a perceived approach of modifying a functional protein. For example, function of the protein often requires approximation in three dimensions and proper folding of secondary structure elements, which cannot be easily achieved in the hybrid protein with knowledge and techniques presently available in the art.

One example of functional polypeptides of interest is human relaxin-2 (relaxin). It is a 53-residue peptide hormone that belongs to the human insulin-relaxin superfamily, which also includes insulin, IGFs 1 and 2, and relaxin-1, and 3. This peptide was first discovered as a hormone of pregnancy, due to its relaxation effects on pubic ligaments (hence the name) and softening the cervix to facilitate parturition. It was reported that relaxin induces a 20% increase in cardiac output, 30% decrease in systemic vascular resistance, 30% increase in global arterial compliance and 45% increase in renal blood flow during pregnancy. It is now known that relaxin confers cardiovascular effects in both males and females, demonstrating potential pharmacological utility in modulating cardiovascular and renal function.

The physiological effects of relaxin are mediated by its signaling through the relaxin/insulin-like family peptide receptor 1 (RXFP1), which leads to the modulation of several signal transduction pathways. Activation of RXFP1 by relaxin induces: (1) upregulation of the endothelin system that leads to vasodilation; (2) extracellular matrix remodeling through regulation of collagen deposition, matrix metalloproteinase and tissue inhibitor of metalloproteinase expression, and overall tissue homoeostasis; (3) a moderation of inflammation by reducing levels of inflammatory cytokines, such as tumor necrosis factor-alpha and transforming growth factor beta; and (4) angiogenesis by activating transcription of vascular endothelial growth factor (VEGF). Relaxin has also been evaluated in various clinical or nonclinical studies as a pharmacological agent for treating acute heart failure, preeclampsia, hypertensive diseases, scleroderma, cervical ripening, fibromyalgia and orthodontics. Relaxin was found to have high specificity and excellent safety profile in, e.g., clinical studies for treating acute heart failure. However, the relaxin peptide is not orally available and has a short serum half-life in the range of 5-15 minutes.

There is a need in the art for effective and robust means of generating derivative or modified functional proteins or polypeptides (e.g., relaxin derivatives) that have improved biological and pharmaceutical properties. The present invention addresses this and other unmet needs in the art.

SUMMARY OF THE INVENTION

In one aspect, the invention provides methods for generating functional derivative effector polypeptides embedded in a heterologous protein scaffold. The method entail (a) modifying a target effector polypeptide with a combinatorial library of N-terminal linkers and a combinatorial library of C-terminal linkers to generate a population of modified effector polypeptides, (b) inserting the modified effector polypeptides into a heterologous protein scaffold to generate a combinatorial library of candidate derivative effector polypeptides, (c) identifying from the library of candidate derivative effector polypeptides one or more members that possess the biological functions or signaling activities of the effector polypeptide. The methods thus allow generation and identification of functional derivative effector polypeptides that are embedded in heterologous protein scaffold.

In some methods of the invention, the employed heterologous protein scaffold is an antibody scaffold. In some of these methods, the modified effector polypeptides are inserted into the antibody scaffold by substituting a complementary determining region (CDR) of the antibody scaffold. In some methods, each of the N-terminal linkers and the C-terminal linkers contains a randomized peptide sequence. For example, the N-terminal linker can contain an amino acid sequence Xa(GbSc)n (SEQ ID NO:86) or Xa(ScGb)n (SEQ ID NO:87), and the C-terminal linker can contain an amino acid sequence (GeSf)mXd (SEQ ID NO:88) or (SfGe)mXd (SEQ ID NO:89). In these sequences, X is any amino acid residue, G is Glycine, S is Serine, m and n are each independently between 1 and 6, inclusive; a and d are each independently between 1 and 5, inclusive; b and e are each independently between 0 and 6, inclusive; and c and f are each independently between 0 and 2, inclusive. In addition, when n (or m) is more than 1, b (or e) and c (or f) in any GS rich repeat can be respectively different from b (or e) and c (or f) in the other GS rich repeats.

In various embodiments of the methods of the invention, (a) and (b) are each performed recombinantly. In some methods, (c) is performed via autocrine-based phenotypic screening of reporter cells in which the candidate derivative effector polypeptides are expressed. In some of these methods, the employed effector polypeptide is a ligand of cellular receptor, e.g., a hormone. In some methods the invention, the employed effector polypeptide has a molecular weight of between about 5 kDa to about 25 kDa. In some embodiments, the employed the reporter cells in the autocrine selection are responsive to expression of the effector polypeptide in the cells. In some methods, the candidate derivative effector polypeptides are expressed in the reporter cells via a lentiviral vector. In some embodiments, the library of expressed candidate derivative effector polypeptides are tethered to the cell membrane. In some other embodiments, the expressed candidate derivative effector polypeptides are secreted from the cells. In various embodiments of the invention, the antibody scaffold employed for embedding the effector polypeptide is a single-chain antibody, e.g., a single chain variable region fragment (scFv). In some embodiments, the antibody scaffold retains its antigen-binding activity upon insertion of the modified effector polypeptides.

Some methods of the invention are directed to generating and selecting functional derivative polypeptides of leptin or single chain Follicle Stimulating Hormone (scFSH) that are embedded in a heterologous protein scaffold. In some of these methods, the N-terminal linker and the C-terminal linker each contains (a) a sequence of 3 to 5 random residues and (b) 1 to 5 tandem repeats of GGGGS (SEQ ID NO:4). In some embodiments, the N-terminal linker contains a sequence of XXX(GGGGS)$_{1-3}$ (SEQ ID NO:35), and the C-terminal linker contains a sequence of (GGGGS)$_{1-3}$ XXX (SEQ ID NO:36).

Some methods of the invention are directed to generating and selecting functional derivative polypeptides of a single chain variant of the relaxin (scRelaxin) molecule, e.g., human relaxin-2. In some of these methods, the single chain variant of the relaxin molecule comprises A chain and B chain connected by linker with the sequence of (GS)n (SEQ ID NO:44), wherein n=3-5. In some methods, the N-terminal linkers contain an amino acid sequence Xa(GGGGS)b (GGGS)c(GGS)d (SEQ ID NO:82) or Xa(GGS)e (SEQ ID NO:83), and the C-terminal linkers comprise an amino acid sequence (SGGGG)f(SG)gXa (SEQ ID NO:84) or (SGGGG)fSgXa (SEQ ID NO:85). In each of these sequence formulae, X is a randomized amino acid residue, a is between 2 and 4 inclusive, b and f are each between 1 and 2 inclusive, e is between 1 and 3 inclusive, and c, d, and g are each independently between 0 and 2 inclusive.

In another aspect, the invention provides modified effector polypeptides that comprise an effector polypeptide that is embedded in and substitutes a complementary determining region (CDR) of an antibody scaffold, wherein the effector polypeptide is linked to the antibody sequence by an N-terminal linker and a C-terminal linker. In some embodiments, the N-terminal linker contains an amino acid sequence Xa(GbSc)n (SEQ ID NO:86) or Xa(ScGb)n (SEQ ID NO:87), and the C-terminal linker contains an amino acid sequence (GeSf)mXd (SEQ ID NO:88) or (SfGe)mXd (SEQ ID NO:89). In these sequences, X is any amino acid residue, G is Glycine, S is Serine, m and n are each independently a random number from 1 to 6; a and d are each independently a random number from 1 to 5; b and e are each independently a random number from 0 to 6; and c and f are each independently a random number from 0 to 2. In addition, when n (or m) is more than 1, b (or e) and c (or f) in any GS rich repeat can be respectively different from b (or e) and c (or f) in the other GS rich repeats. Also provides in the invention are isolated or recombinant polynucleotides that encode the modified effector polypeptides described herein, as well as expression vectors and host cells harboring such polynucleotide sequences.

In some of the modified effector polypeptides of the invention, the effector polypeptide is a ligand of cellular receptor. For example, the effector polypeptide can be a hormone molecule. In some embodiments, the effector polypeptide embedded in the antibody scaffold has a molecular weight of between about 5 kDa to about 25 kDa. In some embodiments, the antibody scaffold for hosting the effector polypeptide is a single chain variable region fragment (scFv). In some modified effector polypeptides of the invention, the single chain antibody scaffold has an amino acid sequence shown in SEQ ID NO:1, and the HCDR3 (LGITKTSTCYT; SEQ ID NO:3) in the antibody scaffold is replaced with the effector polypeptide.

In some modified effector polypeptides of the invention, the effector polypeptide is a leptin or a scFSH. In some of these embodiments, each of the N-terminal linker and the C-terminal linker contains a randomized sequence. In some embodiments, the N-terminal linker sequence contains a sequence XXX$(GGGGS)_{1\sim3}$ (SEQ ID NO:35), and the C-terminal linker sequence contains a sequence $(GGGGS)_{1\sim3}$ XXX (SEQ ID NO:36). Some modified effector polypeptides of the invention contain human Leptin embedded in a scFv scaffold with a N-terminal linker and a C-terminal linker that are substantially identical to (1) LGVGGGGS (SEQ ID NO:5) and GGGGSERT (SEQ ID NO:6), respectively; (2) HLTGGGGS (SEQ ID NO:7) and GSGGSGGGGSDPS (SEQ ID NO:8), respectively; (3) PWAGGGGSGGGGSGGGGS (SEQ ID NO:9) and GGGGSQPP (SEQ ID NO:10), respectively; (4) KTSGGGGSGGGGS (SEQ ID NO:11) and GGGGSSDE (SEQ ID NO:12), respectively; (5) KVTGGGGS (SEQ ID NO:13) and GGGGSQLE (SEQ ID NO:14), respectively; or (6) RHMGGGGS (SEQ ID NO:37) and GGGGSGGGGSTDT (SEQ ID NO:38), respectively. Some modified effector polypeptides of the invention contain a single chain human FSH embedded in a scFv scaffold with a N-terminal linker and a C-terminal linker that are substantially identical to (1) RSHGGGGS (SEQ ID NO:15) and GGGGSVNP (SEQ ID NO:16), respectively; (2) QRVGGGGS (SEQ ID NO:17) and GGGGSGGGGSRSA (SEQ ID NO:18), respectively; or (3) RVLGGGGS (SEQ ID NO:19) and GGGGSGGGGSQSS (SEQ ID NO:20), respectively.

In some other modified effector polypeptides of the invention, the embedded effector polypeptide is a single chain human relaxin-2 (scRelaxin). In some of these molecules, the single chain relaxin polypeptide contains A chain and B chain connected by a connector sequence (GS)n (SEQ ID NO:44), wherein n=3-5. In some embodiments, the scRelaxin is embedded in the host scFv antibody scaffold with an N-terminal linker sequence XXXGGGGSGGGSGGS (SEQ ID NO:78) or XXXGGSGGS (SEQ ID NO:79), and a C-terminal linker sequence SGGGGSGGGGSGXXX (SEQ ID NO:80) or SGGGGSXXX (SEQ ID NO:81), wherein X is any randomized residue. In some embodiments, the N-terminal linker sequence and the C-terminal linker sequence for embedding the scRelaxin are respectively substantially identical to sequences shown in (1) RTRGGSGGS (SEQ ID NO:50) and SGGGGSLMS (SEQ ID NO:51) (Clone A3); (2) RTRGGSGGS (SEQ ID NO:50) and SGGGGSKPP (SEQ ID NO:52) (Clone A12-2); (3) PLNGGSGGS (SEQ ID NO:53) and SGGGGSKPP (SEQ ID NO:52) (Clone C12-1); (4) LPRGGGGSGGGSGGS (SEQ ID NO:54) and SGGGGSLDS (SEQ ID NO:55); (5) QTTGGSGGS (SEQ ID NO:56) and SGGGGSKGT (SEQ ID NO:57); (6) HMFGGSGGS (SEQ ID NO:58) and SGGGGSKAP (SEQ ID NO:59); (7) QRGGGSGGS (SEQ ID NO:60) and SGGGGSWSP (SEQ ID NO:61); (8) RQRGGGGSGGGSGGS (SEQ ID NO:62) and SGGGGSVRA (SEQ ID NO:63); (9) RLTGGSGGS (SEQ ID NO:64) and SSGGWSAGGGSGVRS (SEQ ID NO:65); or (10) RNRGGGGSGGRSGGS (SEQ ID NO:66) and SGGGGSGGGGSGGRP (SEQ ID NO:67). In some embodiments, the N-terminal linker sequence and the C-terminal linker sequence for embedding the scRelaxin in the scFv antibody scaffold are respectively identical to the sequences shown in (1) RTRGGSGGS (SEQ ID NO:50) and SGGGGSLMS (SEQ ID NO:51) (Clone A3); (2) RTRGGSGGS (SEQ ID NO:50) and SGGGGSKPP (SEQ ID NO:52) (Clone A12-2); or (3) PLNGGSGGS (SEQ ID NO:53) and SGGGGSKPP (SEQ ID NO:52) (Clone C12-1).

In some modified relaxin molecules of the invention, the scRelaxin polypeptide that is embedded in and replace the HCDR3 loop LGITKTSTCYT (SEQ ID NO:3), including the linker sequences, has an amino acid sequence shown in SEQ ID NO:69, SEQ ID NO:71, or SEQ ID NO:72. Some specific examples of the modified human relaxin molecules of the invention contain an amino acid sequence that is substantially identical to a sequence selected from the group consisting of SEQ ID NOs:68-77.

In another aspect, the invention provides methods for treating or preventing the development of a disease or disorder that is associated with or mediated by leptin deficiency in a subject. The methods involve administering to the subject a pharmaceutical composition comprising a therapeutically effective amount of the modified or derivative leptin polypeptide described herein. Some of these methods are directed to treating subjects afflicted with obesity, lipodystrophy, hypothalamic amenorrhea, or congenital leptin deficiency. In another aspect, the invention provides methods for treating or preventing the development of a disease or disorder that is associated with or mediated by FSH deficiency in a subject. These methods entail administering to the subject a pharmaceutical composition comprising a therapeutically effective amount of the modified or derivative scFSH polypeptide of the invention. Some of these methods are directed to treating subjects afflicted with of hypogonadism, polycystic ovarian syndrome, Kallmann syndrome, hypothalamic suppression, hypopituitarism, hyperprolactinemia, or gonadotropin deficiency. In still another aspect, the invention provides methods for treating or preventing the development of a disease or disorder that is associated with or mediated by relaxin-2 deficiency or impaired relaxin-2 signaling in a subject. The methods entail administering to the subject a pharmaceutical composition comprising a therapeutically effective amount of the modified or derivative relaxin molecule of the invention. Some of these methods are directed to treating subjects afflicted with claim heart failure, fibrosis, hypertension, scleroderma, or cancer.

Additional aspects and embodiments of the invention, as well as the specific properties and advantages of the present invention, are described in the remaining portions of the specification and claims.

BRIEF DESCRIPTION OF THE DRAWINGS

FIG. 6 shows the amino acid sequences (SEQ ID NOs: 68-77, respectively) of 10 identified antibody-embedded scRelaxin-H2 clones. Sequences of the terminal linkers, the A and B chains of relaxin-H2, and the inter-chain connector are also indicated.

DETAILED DESCRIPTION OF THE INVENTION

I. Overview

Figure 1:
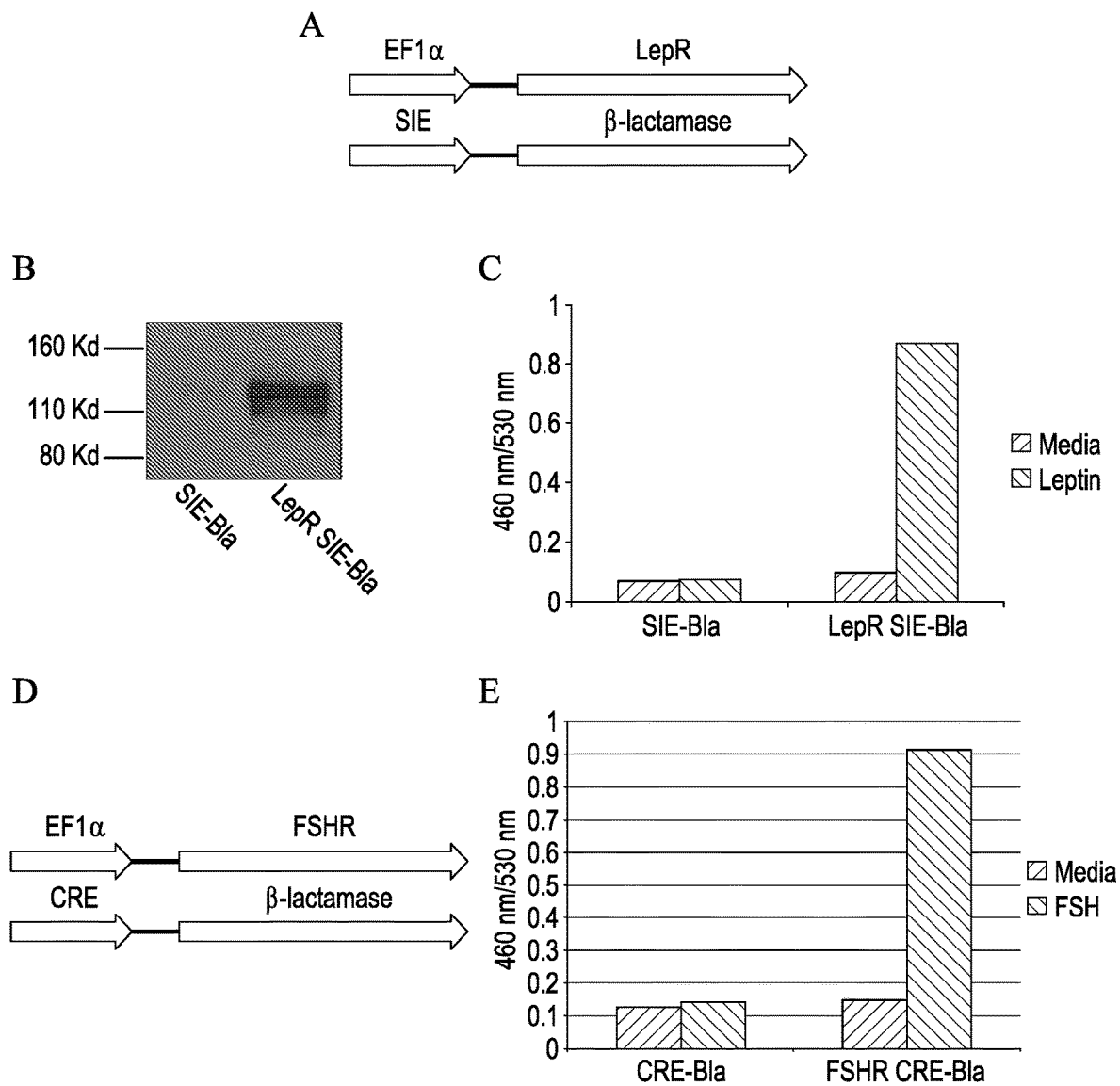
FIGS. 1A-1E show construction of autocrine based stable cell lines. A, Schematic diagram of elements used for autocrine cell construction of LepR SIE-Bla cells. B, Expression of HA-tagged LepR in LepR SIE-Bla cells, detected with anti-HA antibody. C, Response of LepR SIE-Bla cells to 1 ng/ml Leptin. D, Schematic diagram of elements used for autocrine cell construction of FSHR CRE-Bla cells. E, Response of FSHR CRE-Bla cells to 1 ng/ml FSH.
Figure 2:
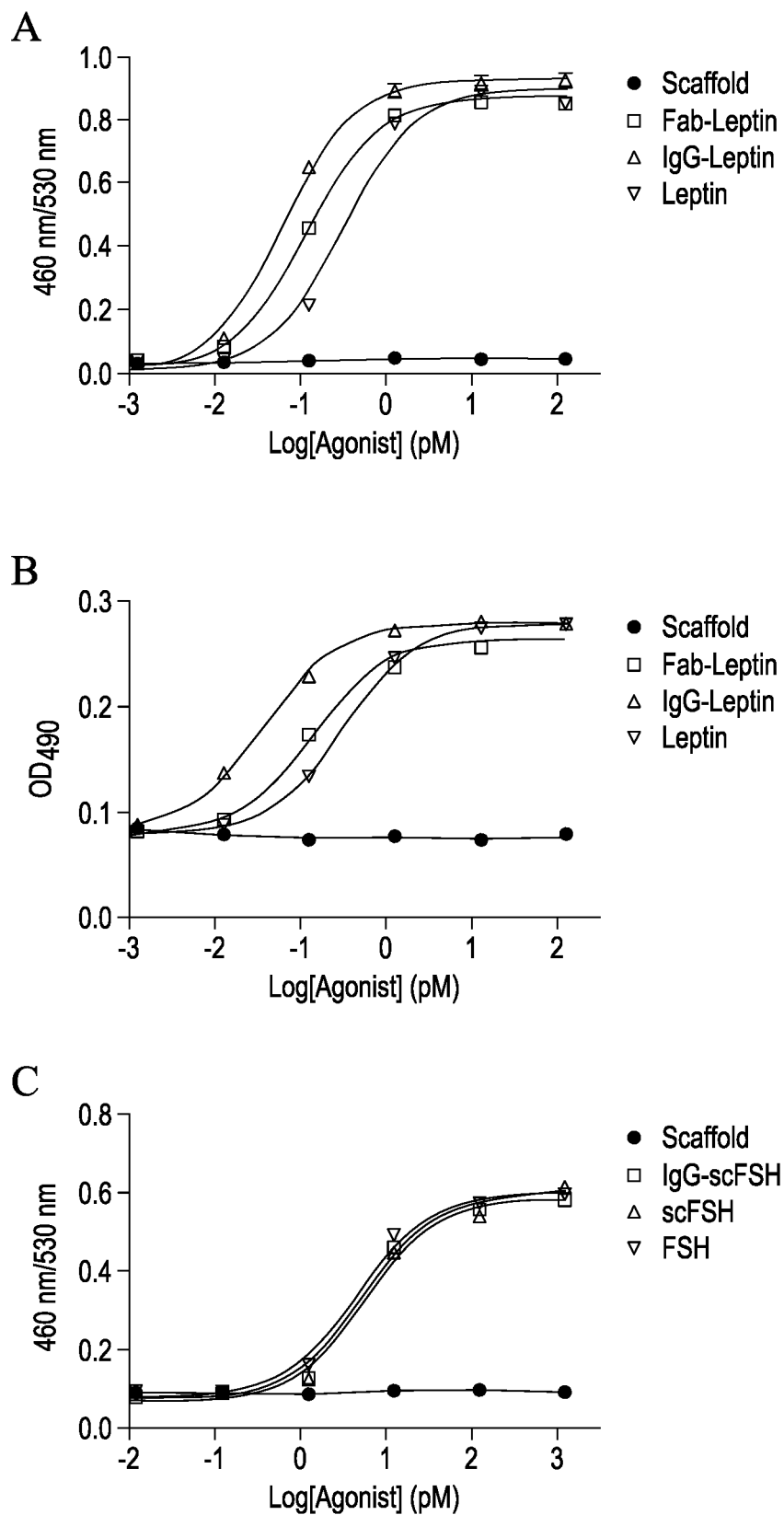
FIGS. 2A-2C show in vitro activity of leptin or scFSH molecules embedded in an antibody scaffold. A, FRET assay using LepR SIE-Bla cells to measure the Leptin $EC_{50}$ of the selected embedded Leptin clone. The $EC_{50}$ of Fab, IgG and native Leptin were 118.3 pM, 58.7 pM and 313.4 pM, respectively. B, Proliferation assay using Baf3 LepR cells to measure the $EC_{50}$ of the selected embedded Leptin clone. The $EC_{50}$ of Fab, IgG and native Leptin were 131.9 pM, 37.2 pM and 309.6 pM, respectively. C, FRET assay using FSHR CRE-Bla cells to measure $EC_{50}$ of FSH in the selected embedded FSH clone. The $EC_{50}$ of IgG-scFSH, scFSH and native FSH were 5.5 pM, 5.7 pM and 4.6 pM, respectively.

The present invention is predicated in part on the studies undertaken by the present inventors to generate modified or derivative functional polypeptides (e.g., Leptin, Follicle Stimulating Hormone (FSH), and relaxin molecules) which were inserted into a heterologous protein scaffold (e.g., an antibody scaffold) and which retain full signaling or biological activities of the original functional polypeptides. Specifically, the inventors studied whether antibodies in which a functional polypeptide molecule is inserted could be selected for function in autocrine-based phenotypic screens. Preferably, the host protein scaffold is a human antibody scaffold such as a scFv human antibody described herein. As exemplifications, a CDR loop in the guest antibody scaffold (e.g., an HCDR3 protein loop) was replaced with the full length sequence of hormones Leptin, single chain FSH or a single chain relaxin-H2, respectively. These screens allowed the inventors to select experimentally from a combinatorial library of junction sequences for linking the guest polypeptide sequence to the host scaffold. By testing a very large number of different junctions, junctions that are permissive for proper function of the guest element are determined.

In selecting functional polypeptides embedded in another protein scaffold, the inventors first generated a library of diverse junction sequences for the incorporation of the guest secondary or tertiary structure (guest polypeptides or proteins) into the heterologous host protein scaffold. Specifically, the functional polypeptides were inserted between large combinatorial libraries of about $10^7$ different N- and C-terminal junctions. The junctions that are permissive for function were then selected in autocrine-based phenotypic screens. Since a very large number of candidates are studied, a robust autocrine reporter system was used for selection of permissive junctions. With such autocrine selection systems, millions of potential agonists and their receptor are expressed in cells such that each cell has a cognate receptor and one member of the repertoire of potential agonists. Using modern cell sorting methods, about 20 million combinatorial junctions per hour can be screened for those that are permissive for function. As exemplified herein, employment of the combinatorial junctions for inserting the guest polypeptide and the autocrine selection format enabled the inventors to identify functional derivative leptin, scFSH and scRelaxin molecules embedded in an antibody scaffold.

In accordance with these studies, the invention provides methods for generating functional derivatives of effector polypeptides embedded in another protein scaffold (e.g., an antibody scaffold). The large diversity systems and robust selection scheme described herein are applicable to construction of new derivative therapeutic proteins from known therapeutic polypeptides or protein agents, e.g., in methods for designing and selecting recombinant therapeutic polypeptides with improved pharmacokinetic properties. The methods of the invention can also be employed in addressing the general protein folding problem where one could study which new sequences inserted anywhere in a protein allow the folding pathway to proceed along the natural or even a new route. The invention additionally provides specific functional leptin, scFSH or scRelaxin polypeptides that are embedded in an antibody scaffold. Due to their improved biological and/or pharmacological properties (e.g., stability and in vivo half-life), the derivative effector polypeptides (e.g., the leptin, scFSH or scRelaxin derivative polypeptides exemplified herein) of the invention can be useful in various therapeutic or other industrial applications. The following sections provide more detailed guidance for practicing the present invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1st ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3rd ed., 2002); *Dictionary of Chemistry*, Hunt (Ed.), Routledge (1st ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt, Ltd. (2002); and *A Dictionary of Biology* (*Oxford Paperback Reference*), Martin and Hine (Eds.), Oxford University Press (4th ed., 2000). In addition, the following definitions are provided to assist the reader in the practice of the invention.

Standard techniques are used for molecular, genetic and biochemical methods employed in the practice of the present invention. See, generally, Sambrook et al., *Molecular Cloning: A Laboratory Manual*, Cold Spring Harbor Press, N.Y., (3rd ed., 2000); Brent et al., *Current Protocols in Molecular Biology*, John Wiley & Sons, Inc. (ringbou ed., 2003); Guthrie et al., *Guide to Yeast Genetics and Molecular Biology*, Academic Press, Inc. (2002); White et al., *PCR Protocols*, Academic Press, Inc. (1990); Freshney, *Culture of Animal Cells*, Wiley-Liss (2005); and Murray et al., *Gene Transfer and Expression Protocols*, The Humana Press Inc. (1991).

The term "antibody" or "antigen-binding fragment" refers to polypeptide chain(s) which exhibit a strong monovalent, bivalent or polyvalent binding to a given antigen, epitope or epitopes. Unless otherwise noted, antibodies or antigen-binding fragments used in the invention can have sequences derived from any vertebrate, camelid, avian or pisces species. They can be generated using any suitable technology, e.g., hybridoma technology, ribosome display, phage display, gene shuffling libraries, semi-synthetic or fully synthetic libraries or combinations thereof. Unless otherwise noted, the term "antibody" as used in the present invention includes intact antibodies, antigen-binding polypeptide fragments and other designer antibodies that are described below or well known in the art (see, e.g., Serafini, J Nucl. Med. 34:533-6, 1993).

An intact "antibody" typically comprises at least two heavy (H) chains (about 50-70 kD) and two light (L) chains (about 25 kD) inter-connected by disulfide bonds. The recognized immunoglobulin genes encoding antibody chains include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Each heavy chain of an antibody is comprised of a heavy chain variable region ($V_H$) and a heavy chain constant region. The heavy chain constant region is comprised of three domains, $C_{H1}$, $C_{H2}$ and $C_{H3}$. Each light chain is comprised of a light chain variable region ($V_L$) and a light chain constant region. The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system and the first component (Clq) of the classical complement system.

The $V_H$ and $V_L$ regions of an antibody can be further subdivided into regions of hypervariability, also termed complementarity determining regions (CDRs), which are interspersed with the more conserved framework regions (FRs). Each $V_H$ and $V_L$ is composed of three CDRs and four FRs, arranged from amino-terminus to carboxyl-terminus in the following order: FR1, CDR1, FR2, CDR2, FR3, CDR3, FR4. The locations of CDR and FR regions and a numbering system have been defined by, e.g., Kabat et al., *Sequences of*

*Proteins of Immunological Interest*, U.S. Department of Health and Human Services, U.S. Government Printing Office (1987 and 1991).

Antibodies to be used in the invention also include antibody fragments or antigen-binding fragments which contain the antigen-binding portions of an intact antibody that retain capacity to bind the cognate antigen. Examples of such antibody fragments include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an intact antibody; (v) disulfide stabilized Fvs (dsFvs) which have an interchain disulfide bond engineered between structurally conserved framework regions; (vi) a single domain antibody (dAb) which consists of a $V_H$ domain (see, e.g., Ward et al., Nature 341:544-546, 1989); and (vii) an isolated complementarity determining region (CDR). In some embodiments of the invention, an antibody scaffold has an embedded effector polypeptide but retains its binding activity for a cognate antigen.

Antibodies suitable for practicing the present invention also encompass single chain antibodies. The term "single chain antibody" refers to a polypeptide comprising a $V_H$ domain and a $V_L$ domain in polypeptide linkage, generally linked via a spacer peptide, and which may comprise additional domains or amino acid sequences at the amino- and/or carboxyl-termini. For example, a single-chain antibody may comprise a tether segment for linking to the encoding polynucleotide. As an example, a single chain variable region fragment (scFv) is a single-chain antibody. Compared to the $V_L$ and $V_H$ domains of the Fv fragment which are coded for by separate genes, a scFv has the two domains joined (e.g., via recombinant methods) by a synthetic linker. This enables them to be made as a single protein chain in which the $V_L$ and $V_H$ regions pair to form monovalent molecules. In some preferred embodiments, the single chain antibodies used in the invention are human antibodies.

Antibodies that may be used in the practice of the present invention also encompass single domain antigen-binding units which have a camelid scaffold. Animals in the camelid family include camels, llamas, and alpacas. Camelids produce functional antibodies devoid of light chains. The heavy chain variable ($V_H$) domain folds autonomously and functions independently as an antigen-binding unit. Its binding surface involves only three CDRs as compared to the six CDRs in classical antigen-binding molecules (Fabs) or single chain variable fragments (scFvs). Camelid antibodies are capable of attaining binding affinities comparable to those of conventional antibodies.

The various antibodies or antigen-binding fragments described herein can be produced by enzymatic or chemical modification of the intact antibodies, or synthesized de novo using recombinant DNA methodologies, or identified using phage display libraries. Methods for generating these antibodies or antigen-binding molecules are all well known in the art. For example, single chain antibodies can be identified using phage display libraries or ribosome display libraries, gene shuffled libraries (see, e.g., McCafferty et al., Nature 348:552-554, 1990; and U.S. Pat. No. 4,946,778). In particular, scFv antibodies can be obtained using methods described in, e.g., Bird et al., Science 242:423-426, 1988; and Huston et al., Proc. Natl. Acad. Sci. USA 85:5879-5883, 1988. Fv antibody fragments can be generated as described in Skerra and Phückthun, Science 240:1038-41, 1988. Disulfide-stabilized Fv fragments (dsFvs) can be made using methods described in, e.g., Reiter et al., Int. J. Cancer 67:113-23, 1996. Similarly, single domain antibodies (dAbs) can be produced by a variety of methods described in, e.g., Ward et al., Nature 341:544-546, 1989; and Cai and Garen, Proc. Natl. Acad. Sci. USA 93:6280-85, 1996. Camelid single domain antibodies can be produced using methods well known in the art, e.g., Dumoulin et al., Nature Struct. Biol. 11:500-515, 2002; Ghahroudi et al., FEBS Letters 414:521-526, 1997; and Bond et al., J Mol Biol. 332:643-55, 2003. Other types of antigen-binding fragments (e.g., Fab, F(ab')$_2$ or Fd fragments) can also be readily produced with routinely practiced immunology methods. See, e.g., Harlow & Lane, *Using Antibodies, A Laboratory Manual*, Cold Spring Harbor Laboratory Press, Cold Spring Harbor, N.Y., 1998.

Binding affinity is generally expressed in terms of equilibrium association or dissociation constants ($K_a$ or $K_d$, respectively), which are in turn reciprocal ratios of dissociation and association rate constants ($k_d$ and $k_a$, respectively). Thus, equivalent affinities may correspond to different rate constants, so long as the ratio of the rate constants remains the same.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

The term "contacting" has its normal meaning and refers to combining two or more agents (e.g., an effector polypeptide agent and a receptor protein) or combining agents and cells. Contacting as used herein can occur in vitro, e.g., mixing a library of polypeptides with a population of cells in a test tube or other container. Contacting can also occur in vivo, e.g., between a polypeptide and another molecule such as a receptor protein inside a host cell or inside the body of a subject.

A "derivative of an effector polypeptide embedded in an antibody scaffold" or "an antibody scaffold embedded derivative of an effector polypeptide" refers to a fusion polypeptide in which the effector polypeptide (guest polypeptide) is inserted into and replaces a specific epitope or domain of an antibody sequence (e.g., host scaffold). Typically, the effector polypeptide is inserted into the host scaffold via an N-terminal linker sequence and/or a C-terminal linker sequence.

As used herein, an effector polypeptide or functional polypeptide refers to any polypeptide, oligopeptide or short peptide sequence that possesses a cellular (e.g., signaling) or biochemical (e.g., enzymatic) function. In some embodiments, the effector or functional polypeptide to be used in the practice of the invention is capable of modulating a cellular response or eliciting a signaling event by selectively binding to a receptor molecule in a host cell. The cellular activities to be modulated by the effector polypeptide can be, e.g., enzyme activity, gene expression, or cell signaling. Examples of effect polypeptides include but are not limited to cytokines, growth factors, neurotrophic factors, integrins, cell adhesion molecules, enzyme substrates, other hormones, and polypeptide ligands of cell surface receptors.

A "fusion" protein or polypeptide refers to a polypeptide comprised of at least two polypeptides and a linking sequence or a linkage to operatively link the two polypeptides into one continuous polypeptide. The two polypeptides linked in a fusion polypeptide are typically derived from two independent sources, and therefore a fusion polypeptide comprises two linked polypeptides not normally found linked in nature.

FSH is a hormone found in humans and other animals. It is synthesized and secreted by gonadotrophs of the anterior pituitary gland. FSH regulates the development, growth, pubertal maturation and reproductive processes of the body. Human FSH is a 35.5 kD glycoprotein dimer containing the alpha and beta subunits. The alpha subunit (FSH α) contains 92 amino acids, while the beta subunit (FSH β) has 111 amino acids. It is the beta subunit which confers its specific biologic action and which is responsible for interaction with the FSH-receptor.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

The term "isolated" means a molecule is removed from its natural surroundings. However, some of the components found with it may continue to be with an "isolated" protein. Thus, an "isolated polypeptide" is not as it appears in nature but may be substantially less than 100% pure protein.

Methods of alignment of sequences for comparison are well known in the art. Optimal alignment of sequences for comparison can be conducted, e.g., by the local homology algorithm of Smith and Waterman, Adv. Appl. Math. 2:482c, 1970; by the homology alignment algorithm of Needleman and Wunsch, J. Mol. Biol. 48:443, 1970; by the search for similarity method of Pearson and Lipman, Proc. Nat'l. Acad. Sci. USA 85:2444, 1988; by computerized implementations of these algorithms (GAP, BESTFIT, FASTA, and TFASTA in the Wisconsin Genetics Software Package, Genetics Computer Group, Madison, Wis.); or by manual alignment and visual inspection (see, e.g., Brent et al., *Current Protocols in Molecular Biology*, John Wiley & Sons, Inc. (ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Leptin, the satiety hormone, is a hormone made by fat cells which regulates the amount of fat stored in the body. It does this by adjusting both the sensation of hunger, and adjusting energy expenditures. Hunger is inhibited (satiety) when the amount of fat stored reaches a certain level. Leptin is then secreted and circulates through the body, eventually activating leptin receptors in the arcuate nucleus of the hypothalamus. Energy expenditure is increased both by the signal to the brain, and directly via leptin receptors on peripheral targets. The effect of leptin is opposite to that of ghrelin, the "hunger hormone". Ghrelin receptors are on the same brain cells as leptin receptors, so these cells receive competing satiety and hunger signals. Leptin and ghrelin, along with many other hormones, participate in the complex process of energy homeostasis.

"Linkage" refers to means of operably or functionally connecting two biomolecules (e.g., polypeptides or polynucleotides encoding two polypeptides), including, without limitation, recombinant fusion, covalent bonding, disulfide bonding, ionic bonding, hydrogen bonding, and electrostatic bonding. "Fused" refers to linkage by covalent bonding. A "linker" or "spacer" refers to a molecule or group of molecules that connects two biomolecules, and serves to place the two molecules in a preferred configuration with minimal steric hindrance.

The term "operably linked" when referring to a nucleic acid, means a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide is polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as nucleotide polymers.

Polypeptides are polymer chains comprised of amino acid residue monomers which are joined together through amide bonds (peptide bonds). The amino acids may be the L-optical isomer or the D-optical isomer. In general, polypeptides refer to long polymers of amino acid residues, e.g., those consisting of at least more than 10, 20, 50, 100, 200, 500, or more amino acid residue monomers. However, unless otherwise noted, the term polypeptide as used herein also encompass short peptides which typically contain two or more amino acid monomers but usually not more than 10, 15, or 20 amino acid monomers.

Proteins are long polymers of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies. In some embodiments, the terms polypeptide and protein may be used interchangeably.

The term "reference polypeptide" or "target polypeptide" is also used herein to refer to a molecule of interest that can be used in the methods of the invention for generating derivative polypeptides embedded in another protein scaffold (e.g., an antibody scaffold). Preferably, the target polypeptide for practicing the present invention is a signaling molecule that can modulate or elicit a cellular response in a host cell.

Native functional relaxin molecules typically contain an A chain and a B chain. Like insulin, relaxin is initially synthesized on the ribosome as an immature pre-prohormone, prorelaxin, as a single-chain structure attached to an N-terminal signal sequence. The signal sequence directs the transport of the peptide from the ribosomal ubiquitins. Following the loss of signal peptide, prorelaxin is converted to a prohormone via co-translational modifications. Proteolytic of the prohormone to remove a C-chain then yields the A- and B-chain combination, forming mature, active 2-chain heterodimeric peptide. In this two-chain structure, the A and B chains are cross-linked by three disulfide bonds with two linking both A and B chains and an intra-chain disulfide bond within the A chain. In the case of human relaxin-2, it's A and B chains respectively contain 24 amino acids (QLYSALANKCCHVGCTKRSLARFC) (SEQ ID NO:42) and 29 amino acids (DSWMEEVIKLCGRELVRAQIA-ICGMSTWS) (SEQ ID NO:43), which are cross-linked by the three disulfide bonds.

A cell has been "transformed" by exogenous or heterologous polynucleotide when such polynucleotide has been introduced inside the cell. The transforming polynucleotide may or may not be integrated (covalently linked) into the genome of the cell. In prokaryotes, yeast, and mammalian cells for example, the transforming polynucleotide may be maintained on an episomal element such as a plasmid. With respect to eukaryotic cells, a stably transformed cell is one in which the transforming polynucleotide has become integrated into a chromosome so that it is inherited by daughter cells through chromosome replication. This stability is demonstrated by the ability of the eukaryotic cell to establish cell lines or clones comprised of a population of daughter cells containing the transforming polynucleotide. A "clone" is a population of cells derived from a single cell or common ancestor by mitosis. A "cell line" is a clone of a primary cell that is capable of stable growth in vitro for many generations.

A "variant" of a reference polypeptide refers to a molecule which has a structure that is derived from or similar to that of the reference polypeptide. Typically, the variant is obtained by chemical or biological modification of the reference polypeptide in a controlled or random manner. Methods for performing recombinant modulation of a polypeptide are well known in the art, e.g., site-specific mutagenesis, error-prone PCR, restriction digestion and relegation, and polynucleotide shuffling.

A "vector" or "construct" is a replicon, such as plasmid, phage or cosmid, to which another polynucleotide segment may be attached so as to bring about the replication of the attached segment. Vectors capable of directing the expression of genes encoding for one or more polypeptides are referred to as "expression vectors".

III. General Schemes for Generating Functional Polypeptides Embedded in Another Protein The invention provides methods for producing and selecting functional derivative proteins or polypeptides in which an effector polypeptide (or "guest polypeptide") is embedded in a different or heterologous protein scaffold. The heterologous protein scaffold can be any protein or polypeptide sequence that is not linked to the effector polypeptide in the natural or wildtype environment. In some embodiments, the heterologous scaffold ("host protein" or "acceptor scaffold") is an antibody scaffold. Various effector polypeptide or effector molecules can be used in the practice of the present invention. While termed effector polypeptide herein, the effector polypeptide suitable for the invention also includes short functional peptides, e.g., peptides containing as few as 10 amino acid residues. In terms of its biological activity, the effector polypeptide can be of any biochemical nature. These include, e.g., cytokines, hormones, growth factors and hormones, peptide or polypeptide ligands of cellular receptors. Specific examples of effector polypeptides or peptides that can be used in the invention to generate derivative polypeptides embedded in another protein include, e.g., leptin, ghrelin, FSH, relaxins, thyroid-stimulating hormone (TSH), human chorionic gonadotropin (hCG), interleukins, interferons, and TNFα. While the invention is illustrated in some detail herein with several functional polypeptides (e.g., leptin, FSH, relaxin and other immune- or signaling-modulators) as examples of effector polypeptides, other effector polypeptides or functional proteins can also be employed in the practice of the invention.

In addition to the diversity of their biological or cellular functions, the effector polypeptides suitable for the invention can also differ substantially in their sizes and native structures. In some embodiments, the effector polypeptide is a wildtype single chain protein. In some embodiments, the effector polypeptide is a single chain molecule that is derived from a multiple chain protein. In general, the effector polypeptide can be any functional polypeptide or peptide that contains at least about 10 amino acid residues. In some embodiments, the effector polypeptide contains between about 10 to about 10,000 amino acid residues in length. In some embodiments, the effector polypeptide contains between about 25 to about 1000 amino acid residues in length. In some preferred embodiments, the effector polypeptide contains about 50 to about 250 amino acid residues in length. Thus, the polypeptides or proteins suitable for the invention can have a molecular weight of from about 1 kDa to about 1,000 kDa, and preferably from about 2.5 kDa to about 250 kDa. In some more preferred embodiments, the employed effector polypeptide has a molecular weight of about 5 kDa to about 25 kDa or 50 kDa.

To select for a functional derivative polypeptide embedded in another protein scaffold (e.g., an antibody scaffold), the native effector polypeptide (or functional fragment thereof) may be inserted into the host scaffold at any position that is conducive to maintaining or enhancing the function and stability of the effector polypeptide. This means the chosen insertion site ideally should not negatively impact the biochemical functions or other biological properties of the effector polypeptide. In some preferred embodiments, the resulting chimeric or fusion molecule should retain at least 25%, 50%, 60%, 70%, 80%, 90%, 95% or more of the cellular or biochemical activities of the native guest polypeptide. In some embodiments, the effector polypeptide is inserted into the host scaffold by replacing a specific epitope of the host protein, e.g., a CDR loop. In various embodiments, the choice of site of insertion can be based on sequence homology analysis of the host scaffold to locate a region that can accommodate the insert sequence.

In some embodiments, the host scaffold is an antibody or antigen-binding fragment. The antibody scaffold can be a single chain antibody fragment such as a scFv exemplified herein. The antibody scaffold can also be a full antibody, e.g., an IgG molecule. When a multiple chain antibody molecule is used, the effector polypeptide sequence is typically inserted into one immunoglobulin chain (e.g., the light chain or the heavy chain). In these embodiments, the host cell for expressing the derivative polypeptide (and/or for functional selection) typically also express the other antibody chain. Alternatively, the vector expressing the derivative polypeptide can also harbor a second open reading frame expressing the other antibody chain. When an antibody is used as the host scaffold, the epitope to be replaced by the functional polypeptide can be a CDR or portion thereof, as exemplified herein. For example, the effector polypeptide can be inserted into an antibody scaffold by replacing the CDRH1 loop of the acceptor scaffold. In some other embodiments, the guest polypeptide can be inserted into the host scaffold at a site that is outside CDRH1 and/or other CDR regions. As detailed herein (e.g., Example 9), insertions of a short peptide into the scFv antibody scaffold exemplified herein at several sites outside the CDR loops were also found to be permissible.

To help maintain the natural biochemical or cellular function of the inserted guest effector polypeptide, an N-terminal linker and a C-terminal linker are used for inserting the native effector polypeptide into the host scaffold. To generate diversity in the juncture for inserting the native polypeptide into the host scaffold, combinatorial libraries of linker sequences ("combinatorial junction libraries") are used to generate a combinatorial library of hybrid molecules containing the host protein scaffold with an embedded native effector polypeptide. By adding the junctions at both the N- and C-terminus of the effector sequence, a diversity of derivative molecules in the order of $10^5$, $10^6$, $10^7$, $10^8$, $10^9$, $10^{10}$ or higher can be generated for the effector polypeptide. The diversity of the linker sequences enables one to select from the library of hybrid molecules one or more members which contain linker sequences that allow the embedded native polypeptide to retain one or more of its biological or signaling activities. Different combinatorial library of junctions can be used in the selection methods of the invention, depending on the specific effector polypeptide to be embedded into the host protein scaffold.

In some embodiments, the N-terminal linker and the C-terminal linker contain identical sequences. In some embodiments, the linker sequences flanking the effector sequence are different. In various embodiments, members of the combinatorial junction libraries of the invention can contain at least 4, 5, 6, 8, 10, 15, 20, 25, 30, 40, 50, 75, 100 or more amino acid residues in length. In some preferred embodiments, the member linkers of the library are short peptides, e.g., peptides of from about 5 to about 30 amino acids. The peptides can be digests of naturally occurring proteins, random peptides, or "biased" random peptides. In some embodiments, randomized amino acid sequences are used in the linkers, e.g., as exemplified herein for selecting functional leptin, scFSH or scRelaxin derivative polypeptides. In some embodiments, member linkers of the combinatorial libraries are fully randomized, with no sequence preferences or constants at any position. In some other embodiments, the library can be biased, i.e., some positions within the sequence are either held constant, or are selected from a limited number of possibilities. For example, in some cases, the amino acid residues are randomized within a defined class, e.g., of hydrophobic amino acids, hydrophilic residues, satirically biased (either small or large) residues, towards the creation of cysteines, for cross-linking, prolines for SH-3 domains, serines, threonines, tyrosines or histidines for phosphorylation sites, or to purines.

In some embodiments, each of the N-terminal linkers and the C-terminal linkers for inserting the guest polypeptide contains a non-randomized sequence portion and a randomized sequence segment. In some of these embodiments, the N-terminal linkers contain a sequence Xa(GbSc)n (SEQ ID NO:86) or Xa(ScGb)n (SEQ ID NO:87), and the C-terminal linker contain an amino acid sequence (GeSf)mXd (SEQ ID NO:88) or (SfGe)mXd (SEQ ID NO:89). In these sequence formulae, X represents any amino acid residue, G is Glycine, S is Serine, m and n are each independently a random number from 1 to 6; a and d are each independently a random number from 1 to 5; b and e are each independently a random number from 0 to 6; and c and f are each independently a random number from 0 to 2. In addition, when multiple GS rich repeats or segments (GbSc, ScGb, GeSf or SfGe) are present in the linker sequence (i.e., when n and/or m are more than 1), the number of Gly or Ser residues in each segment can be independently different from the number of Gly or Ser residues in the other segments. Conventional genetic engineering techniques are typically employed in the present invention for generating linker sequences and for expressing the library of the derivative effector polypeptides embedded in another protein scaffold. As exemplified herein, the polynucleotide sequence encoding the effector polypeptide or variant is first modified by adding randomized N-terminal- and C-terminal junction sequences. The effector sequence flanked by the combinatorial library of junction sequences can then be cloned into the host protein scaffold (e.g., an antibody scaffold).

To produce a library of candidate functional derivative polypeptides (e.g., leptin or other hormones) embedded in another protein scaffold, any of the genes or cDNA sequences coding for the reference effector polypeptide (e.g., leptin) can be utilized. In addition to full length sequences, a functionally active variant or fragment of the reference effector polypeptide may also be employed. In some embodiments, variants of the reference effector polypeptide from various species may be used. In some embodiments, the variants are sequences that encode the reference effector polypeptide but that differ conservatively because of the degeneracy of the genetic code. They also encompass sequences that are substantially identical to the wildtype sequence encoding the reference polypeptide. Thus, suitable variants encompass natural allelic variants, e.g., due to sequence polymorphisms that lead to changes in the amino acid sequences of the encoded proteins. Such variants may exist among individuals within a population, e.g., the human population. To practice the present invention, the nucleotide sequence polymorphism or amino acid sequence variance of the employed sequence should not alter the functional activity of the encoded effector polypeptide (e.g., leptin or relaxin). Suitable variants of a reference effector polypeptide further include synthetically derived nucleotide sequences that have been generated, for example, by using site-directed mutagenesis but which still harbor the biological or signaling activities of the reference effector polypeptide as disclosed herein. These include, e.g., variants which have conservative amino acid substitutions at one or more nonessential residues that do not lead to an alteration in the biological or signaling activity.

Once effector sequence flanked by the library of combinatorial junction sequences are inserted into the host scaffold, the library of candidate derivative effector molecules embedded in the host scaffold can be introduced into an appropriate system for expression and functional selection. First, the polynucleotides encoding the candidate derivative or modified effector polypeptides are inserted into a suitable expression system to produce a library of candidate effector polypeptides. In some embodiments, the expression vector can incorporate a protein yield parameter to enable selection of clones with improved protein production. For example, as exemplified herein, the vector can contain a sequence encoding mCherry that is fused to the C-terminus of the scFv scaffold. This allows selection for high expressing clones by using an additional gate for high mCherry signal prior to selection via functional assays (e.g., the FRET assay exemplified herein).

Upon expression, the various candidate derivative polypeptides can be contacted with or introduced into a population of appropriate host cells for functional selection. In some embodiments, an autocrine based selection system is employed for the functional selection, as exemplified herein for selecting functional leptin, FSH and relaxin polypeptides. For effector polypeptides that mediate signaling pathways through a cellular receptor, e.g., hormones, cytokines or other types of signaling mediators or receptor ligands, the host cells typically express a corresponding cellular receptor of the effector polypeptide. In some embodiments, the chosen host cell for the selection does not endogenously express a cellular receptor of the effector polypeptide. In these methods, the host cell for functional selection of the candidate effector polypeptides can also be engineered to express the receptor. For effector polypeptides of other biochemical nature, e.g., enzymes, an appropriate reporting system that responds to the enzymatic activities of the effector polypeptides expressed by the cells can be readily developed. For example, many well-known reporter assays in high-throughput format for monitoring receptor signaling or enzymatic activities can be employed and adapted in the practice of the present invention. See, e.g., Andricopulo et al., Curr. Top. Med. Chem., 2009, 9, 771; Dailey et al., Exp. Mol. Pathol., 2009, 86, 141; Lee et al., J. Nat. Prod., 2010, 73, 500; Li et al., Science, 2009, 325, 161.

Construction of cell lines for expressing and/or selecting a library of candidate effector polypeptides of the invention can be performed with standard procedures well known in the art or the specific exemplifications described herein. Suitable host cells or cell lines for expressing the polypeptide library include the HEK293T cell exemplified herein and many other cell lines well known in the art, e.g., HEK293, CHO, AtT20, BV2, and N18 cell lines. In some embodiments, the candidate effector polypeptides embedded in the antibody scaffold are expressed from a viral vector, e.g., a lentiviral vector. In these methods, a library of vectors (e.g., lentiviral vectors) encoding the combinatorial library of candidate effector polypeptides can first be introduced into a virus production cell line (e.g., HEK293T) to provide a library of polypeptide-encoding viruses. The virus production cell line can be the same as (e.g., the HEK293T cell as exemplified herein) or different from the host cell for selection of functional effector polypeptides. Upon transfecting the viruses into the host cell expressing the receptor of the effector polypeptide, the library of candidate polypeptides will be expressed in the cells.

In some embodiments, the library of candidate effector polypeptides are expressed as soluble molecules and secreted particles (e.g., soluble scRelaxin molecules exemplified herein). In some other embodiments, the candidate effector polypeptides are expressed as library of molecules tethered to the cell membrane. For expressing membrane tethered library of candidate effector polypeptides, the antibody scaffold sequence is operably liked at the N-terminus or the C-terminus to a transmembrane domain. Any transmembrane protein domain known in the art may be used these embodiments of the invention, e.g., the PDGFR transmembrane domain. See, e.g., Remm et al., Genome Res. 10: 1679-1689, 2000; and Hubert et al., Cell Adh. Migr. 4: 313-324, 2010. In some embodiments, the scaffold sequence is connected with the transmembrane domain via a short linker peptide or linker sequence. For example, a linker peptide comprising tandem repeats of GGGGS (SEQ ID NO:4) can be used for connecting the transmembrane domain.

In order to identify functional polypeptides embedded in the host scaffold, the cloning and selection process can be repeated after each round of selection. Once a candidate functional polypeptide is identified from the reporter assay (e.g., activation of a cognate receptor), the corresponding polynucleotide sequence encoding the candidate polypeptide can be isolated, amplified and re-cloned into the expression vector to provide enriched libraries of candidate effector polypeptides. Such enriched candidate effector library can be employed in the next rounds of selection, as exemplified herein for selection of functional scRelaxin-H2 agonist polypeptides. In the subsequent rounds of selections, either the N- or the C-terminal linkers identified in the previous selection can be held constant and the other linkers can be comprised of the same random sequences used previously.

Construction of the polynucleotides and expression vectors of the invention can be readily carried out in accordance with routinely practiced methods of molecular biology. Some specific protocols for performing the required steps of the invention are also exemplified herein. Expression of the polypeptides can employ numerous types of appropriate expression vectors known in the art, including, e.g., vectors containing bacterial, viral, yeast, fungal, insect or mammalian expression systems. As exemplified herein, a preferred expression system for producing the fusion polypeptide libraries of the invention is lentiviral based. Methods for obtaining and using such expression vectors are well-known. For guidance in this and other molecular biology techniques used for compositions or methods of the invention, see, e.g., Sambrook et al, Molecular Cloning, A Laboratory Manual, current edition, Cold Spring Harbor Laboratory, New York; Miller et al, Genetic Engineering, 8:277-298 (Plenum Press, current edition), Wu et al, Methods in Gene Biotechnology (CRC Press, New York, N.Y., current edition), Recombinant Gene Expression Protocols, in Methods in Molecular Biology, Vol. 62, (Tuan, ed., Humana Press, Totowa, N.J., current edition), and Current Protocols in Molecular Biology, (Ausabel et al, Eds.,) John Wiley & Sons, NY (current edition), and references cited therein.

The selected functional effector polypeptides embedded in the host scaffold can be further examined for in vitro and in vivo biological or signaling activities. Depending on the specific effector polypeptide used in the selection, various methods can be used to ascertain that the identified derivative polypeptides possess the desired properties. For example, as exemplified herein for selecting functional leptin derivative polypeptides, in vitro activities of the identified functional leptin molecules embedded in the antibody scaffold can be examined via the FRET assay or an orthogonal proliferation assay detailed herein. In vivo studies of the identified molecules can also be performed to examine their in vivo activities, e.g., stability and other bioactivity such as the ability to cross the blood brain barrier and to elicit a metabolic response. Similar studies can also be designed to examine in vitro and in vivo activities of any other identified effector polypeptides embedded in a heterologous protein scaffold, as exemplified herein for several specific antibody-embedded scRelaxin-H2 agonists.

IV. Selecting Antibody Embedded Functional Leptin or scFSH Polypeptides

As exemplifications, several specific functional polypeptides were inserted into a scFv antibody scaffold, and the resulting library of fusion polypeptides were selected for functionality, in accordance with the schemes described above. These include, e.g., leptin and FSH as detailed in the Examples below. Leptin gene from human and a number of non-human species have been isolated and characterized in the art. Any of these leptin sequences can be readily employed in the practice of the present invention. See, e.g., Zhang et al., Nature 372: 425-32, 1994; Isse et al., J. Biol. Chem. 270 (46), 27728-27733, 1995; Iwase et al., Res. Vet. Sci. 68 (2), 109-114, 2000; Konfortov et al., Mamm. Genome 10, 1142-1145, 1999; and Murakami et al., Biochem. Biophys. Res. Commun. 209 (3), 944-952, 1995. In addition, various leptin analogs may also be used in constructing the leptin fusion molecules of the invention. Examples include metreleptin, PEG-leptin analogs, and various other leptin analogs. See, e.g., Muller et al., J. Pept. Sci. 18:383-93, 2012; Salomon et al., Prot. Exp. Purif. 47:128-136, 2006. Metreleptin (trade name Myalept) is an analog of human leptin. This compound has been approved in Japan for metabolic disorders including lipodystrophy, and also in the United States as a treatment for complications of leptin deficiency, including diabetes and hypertriglyceridemia, in people with congenital generalized or acquired generalized lipodystrophy. Functional derivatives of these leptin analogs that can be generated and selected with methods of the invention provide therapeutic agents with improved activities.

Nucleotide and amino acid sequences of the alpha and beta subunits of human FSH and orthologs from many other non-human species are also known in the art. See, e.g., Saxena et al., J. Biol. Chem. 251, 993-1005, 1976; Watkins et al., DNA 6, 205-212, 1987; Shome et al., J. Protein Chem. 7, 325-339, 1988; Strausberg et al., Proc. Natl. Acad. Sci. U.S.A. 99, 16899-16903, 2002; Kumar et al., Gene 166, 333-334, 1995; Mountford et al., Nucleic Acids Res. 17, 6391, 1989; Noguchi et al., Gen. Comp. Endocrinol. 147, 231-235, 2006; and Shen et al., Gen. Comp. Endocrinol. 125, 375-386, 2002. In addition to these specific leptin and FSH sequences, variants or functional fragments with substantially identical sequences of a leptin (e.g., human leptin) or FSH (e.g., human FSH) can also be used in the invention to generate the antibody scaffold-embedded derivative molecules.

As demonstrated herein, the native dimeric FSH can be converted into a single chain molecule in order to be inserted into the host scaffold for selecting functional derivative molecules. To ensure biological function of the single chain FHS molecule, a connector or linker can be used. As exemplified herein, the native human FSH dimer can be converted into a single chain molecule by linking the α and β subunit-encoding sequences via a connector having a sequence of GGATCAGGATCGAACGCGACGGGG TCAGGTTCTAATGCAACTTCAGGATCGACT AGT (SEQ ID NO:2), which encodes a GSGSNATGSG-SNATSGSTS (SEQ ID NO:33) peptide linker. The connected single chain molecule can then be further modified with the libraries of N-terminal linker sequences and C-terminal linker sequences described herein. The resulting library of derivative scFSH molecules can then be recombinantly cloned into the host scaffold.

A combinatory library of linkers for inserting leptin or scFSH into an scFv scaffold can be prepared using the juncture sequences described above. Fusion of the randomized linker sequences to the effector polypeptides can be readily carried out with standard DNA cloning techniques exemplified herein. Upon expression of the library of candidate fusion molecules of antibody embedded leptin or scFSH, functional section can then be performed. Specifically, some embodiments of the invention are directed to selection of functional leptin derivatives. In these embodiments, a reporter cell line can be employed which expresses a detectable reporter molecule (e.g., β-lactamase) in response to signaling activities mediated by the leptin receptor. For example, the reporter cell line can express the β-lactamase reporter gene under the control of Sis-Inducible Element (SIE) as exemplified herein. Upon contacting the reporter cell line with the library of derivative or fusion leptin molecules, cells with the strongest expression of the reporter molecule (e.g., β-lactamase) can be readily isolated, e.g., using FACS. Similarly, to select functional FSH derivative molecules, host cells (e.g., HEK 293T cells) can express the FSH receptor and also a reporter molecule (e.g., β-lactamase) under the control of the cyclic AMP responsive element (CRE). The library of derivative or fusion scFSH molecules is then selected for functional FSH derivatives that provide the strongest response.

To select for functional leptin or scFSH molecules embedded in an antibody scaffold, a library of juncture linker flanked leptin or scFSH polypeptides are first generated as discussed above. The N-terminal and C-terminal random linker sequence can contain a peptide segment of 2, 3, 4, 5, 6 or more randomized residues. The linker sequences can additionally also contain one or more Gly/Ser rich peptide segments. In some embodiments, the linker contains 2, 3, 4, 5, 6, 7, 8, 9, 10 or more tandem repeats of the same Gly/Ser rich peptide segment (e.g., the GGGGS sequence). In other embodiments, one or more copies of each of several different Gly/Ser rich peptide segments are present in the random linker sequence. As specific examples, the linker can contain a random 3-residue motif and several copies of the GGGGS (SEQ ID NO:4) sequence, as exemplified herein for inserting leptin and scFSH.

To identify functional leptin or scFSH polypeptides from the library of candidate fusion molecules, an autocrine-based reporter system is employed in some embodiments for detection of a phenotype evidencing signaling by the effector polypeptide. With the reporter system, vectors expressing a receptor of the effector polypeptide (e.g., leptin receptor) and a detectable reporter (e.g., β-lactamase under the control of a regulatory sequence that is responsive to signaling of the effector polypeptide) can be introduced into the host cell. As exemplified herein for leptin and FSH, the specific phenotype to be altered is an activity, a signaling pathway or cellular process mediated by the effector polypeptide in the population of reporter cells. Candidate polypeptides that can cause an alteration in the phenotype of interest are identified as "functional derivative molecules of the effector polypeptide embedded in an antibody scaffold" (or "antibody embedded functional derivatives of the effector polypeptide"). Depending on the specific effector polypeptide and its cellular receptor, the phenotype or signaling pathway to be monitored in the methods can be any cellular activity or physiological function mediated by the receptor. However, in some preferred embodiments, the phenotype or signaling pathway to be monitored in the selection methods is response of a reporter molecule (e.g., expression of a reporter gene) introduced into the host cells. This allows for autocrine selection from the library of candidate polypeptides one or more functional derivative effector polypeptides that can induce expression of the reporter molecule by activating the receptor of the effector polypeptide. Other than autocrine reporter systems exemplified herein, other reporter systems based on classical endocrine, paracrine or intracrine signaling can also be developed and employed in the practice of the invention, depending on the specific biochemical nature of the effector polypeptide.

V. Selecting Antibody Embedded Functional scRelaxin Polypeptides

As further exemplification of the general applicability of the methods of the invention for identifying functional polypeptides embedded in another protein scaffold, the invention also provides methods for selecting scFv embedded functional relaxin agonists. The functional relaxin agonists of the invention contain a single chain relaxin-related polypeptide that is embedded in a heterologous antibody scaffold (e.g., an scFv scaffold). Any relaxin molecule or other member of the insulin-relaxin superfamily (esp. human relaxin molecules) and their orthologs or variants can be used in the construction of the functional single chain antibody-relaxin derivative fusions of the invention. To construct the relaxin derivatives, a single chain polypeptide containing the A chain and the B chain of a native relaxin molecule is first generated, preferably by recombinant methods. To ensure biological function of the single chain relaxin molecule, a loop sequence (a connector or linker) can be used to link the two chains. In some embodiments of the invention, the native relaxin chains can be linked via a connector having a sequence of (GS)n (SEQ ID NO:44), wherein n=3-5. As exemplified herein, some antibody-embedded functional scRelaxin-H2 agonists have the A chain and the B chain linked by a loop sequence of GSGSGSGS (SEQ ID NO:45). The connected single chain molecule can then be further modified with the libraries of N-terminal linker sequences and C-terminal linker sequences described herein. The resulting library of derivative scRelaxin molecules can then be recombinantly cloned into the host scaffold.

The A chain and B chain from any native relaxin molecules can be employed in the invention to generate candidate functional scRelaxin derivatives embedded in a protein scaffold. In some preferred embodiments, the candidate functional relaxin derivatives of the invention contain a single chain polypeptide constructed from the A chain and the B chain of human relaxin-2 (H2), Human relaxin-2 is a peptide hormone associated with a number of therapeutically relevant physiological effects, including regulation of collagen metabolism and multiple vascular control pathways. The sequences of the two chains of relaxin-H2 are well known and characterized in the art. Human prorelaxin-2 amino acid sequences (and coding nucleotide sequences) are reported with accession numbers P04090, NP_604390.1 (NM_134441.2), NP_005050.2 (NM_005059.3), and NP_604390 (NM_134441.2). The A chain and B chain of human relacin-2 of relaxin-H2 can be readily obtained via recombinant techniques. In addition to human relaxin-2, sequences of other native relaxin molecules and orthologs can also be used in the construction of the candidate functional relaxin derivatives of the invention. These include, e.g., human relaxin-1, human relaxin-3, and relaxin-1 and relaxin-2 orthologs from other primates, as well as relaxin molecules from other mammals. Sequences of these relaxin molecules are also well known in the art. These include human relaxin 1 sequences (P04808, NP_008842.1, NM_006911), human relaxin-3 (Q8WXF3, NP_543140, NM_080864), chimpanzee prorelaxin-2 (EU437442.1), monkey prorelaxin (ACA13574.1, EU437443), mouse prorelaxin (AAI32657.1, BC132656), zebrafish relaxin (AEL22115.1, JN215212), wolf prorelaxin (AAF60302.1, AF233687), and pig pre-prorelaxin (K01088, AAA31114.1). See, e.g., Crawford et al., EMBO J. 3: 2341-2345, 1984; Stults et al., Biomed. Environ. Mass Spectrom. 19: 655-664, 1990; Hudson et al., EMBO J. 3, 2333-2339, 1984; Itoh et al., J. Biol. Chem. 263, 6656-6664, 1988; and Bathgate et al., J. Biol. Chem. 277, 1148-1157, 2002. Any of these relaxin sequences can be readily employed in constructing the candidate relaxin fusion molecules of the present invention.

In addition to the native relaxin molecules, other variants or analogs derived from the native relaxin molecules can also be used in constructing the candidate scRelaxin derivative polypeptides for practicing the invention. These include, e.g., relaxin variants or analogs that contain a sequence that is substantially identical (e.g., at least 90% or 95% identical) to a native relaxin peptide (e.g., human relaxin 2). In some embodiments, the variants are sequences that encode the reference relaxin polypeptide but that differ conservatively because of the degeneracy of the genetic code. They also encompass functional derivatives that have structural alterations at one or more sites that are not essential for the biological functions of relaxin. Thus, in some embodiments, relaxin variants or functional derivatives suitable for the invention include peptides which, relative to a native relaxin molecule (e.g., human relaxin-2), contain the conserved residues essential to its binding or signaling activities but have otherwise sequence variations, e.g., substitutions at the non-conserved positions or deletions at the N-terminus of the A chain. As examples, functional antibody-embedded scRelaxin-H2 for practicing the invention include molecules with an $A^{21}S$ substitution in the A chain and/or an $A^{21}V$ substitution in the B chain.

To design relaxin variants suitable for agonist selection, any of the structural motifs or residues known to be important for receptor interaction should be maintained. For example, it is known that the active site of human relaxin-2 consists of the mid-region of the B-chain helix and the C-terminal region of the A-chain. See, e.g., Park et al., J. Biol. Chem. 283, 32099-32109, 2008; and Hossain et al., Curr. Protein Pept. Sci. 11, 719-724, 2010. Specifically, comparison of human relaxin-2 primary structures with relaxin peptides from different species reveals a remarkable sequence similarity in the mid-region of the B-chain where two arginine residues are located on the same surface of the α-helix. These two arginines ($A^{13}$ and $A^{17}$) bind to the RXFP1 receptor by both the positive charge and by the hydrogen-bonding network produced by the guanidine group in the side chain of each Arg. In addition, a third amino acid in the B-chain, $IleB^{20}$, has also been reported to be essential for binding to RXFP1. Other than this motif in the B chain, residues $Thr^{16}$, $Lys^{17}$, and $Phe^{23}$ in the A chain of human relaxin-2 are also involved in interactions either with the RXFP1 or RXFP2 receptor. Further, it was reported that the N terminus of the human relaxin-2 A-chain has no functional role, and that shortening of the N terminus of the A-chain by up to four residues had no effect on binding or activation of RXFP1 and RXFP2. See, e.g., Büllesbach et al., Biochemistry 25, 5998-6004, 1986; Büllesbach et al., J. Biol. Chem. 262, 12496-12501, 1987; and Hossain et al., J. Biol. Chem. 283, 17287-17297, 2008.

The libraries of N-terminal and C-terminal linkers for inserting a single chain relaxin polypeptide into the host scaffold can be designed in accordance with the schemes described above. In some embodiments, the linkers can contain a random motif of 3-5 randomized residues and one or more additional GS rich segments. As exemplified herein for relaxin-H2, the polynucleotide sequence encoding the scRelaxin polypeptide or variant is modified by adding junction sequences that respectively encode N-terminal linkers having the sequence Xa(GGGGS)b(GGGS)c(GGS)d (SEQ ID NO:82) or Xa(GGS)e (SEQ ID NO:83), and C-terminal linkers having the sequence (SGGGG)f(SG)gXa (SEQ ID NO:84) or (SGGGG)fSgXa (SEQ ID NO:85). In each of these sequence formulae, X is a randomized amino acid residue, a is a random number from 2 to 4, b and f are each independently a random number from 1 to 2, e is a random number from 1 to 3, and c, d, and g are each independently a random number from 0 to 2. In some embodiments, the N-terminal linkers contain a sequence of GGGGSGGGSGGS (SEQ ID NO:46) or GGSGGS (SEQ ID NO: 47) in addition to the randomized residues, and the C-terminal linkers contain a sequence of SGGGGSGGGGSG (SEQ ID NO:48) or SGGGGS (SEQ ID NO:49) in addition to the randomized residues. The terminal linkers-modified scRelaxin polypeptide can be inserted into and/or replace any portion of the antibody sequence so long as the insertion does not inhibit the function of the guest molecule or substantially impair the structural integrity of the resulting fusion polypeptide. In some embodiments, the modified scRelaxin sequence can be inserted into a complementarity determining region (CDR). Typically, the choice of site of insertion can be based on sequence homology analysis of the host scaffold to locate a region that can accommodate the insert sequence. As exemplified herein for human relaxin-2, the terminal linkers-modified scRelaxin-H2 sequence (e.g., SEQ ID NOs:69, 71 and 72 for clones A3, C12-2 and C12-1, respectively) can be inserted into the scFv host sequence (SEQ ID NO:1) by replacing the HCDR3 region (SEQ ID NO:3) of the antibody to produce candidate antibody-embedded scRelaxin polypeptides.

Insertion of the linker flanked scRelaxin sequence into the scFv scaffold and expression in a host cell of the resulting library of candidate scRelaxin molecules embedded in the host scaffold can be performed as described above. Upon expression, the various candidate antibody-embedded scRelaxin polypeptides can be contacted with or introduced into a population of appropriate cells for functional selection. These cells typically express a corresponding cellular receptor of the relaxin polypeptide (e.g., RXFP1, RXFP2, RXFP3, or RXFP4). In some embodiments, the chosen host cell for the selection does not endogenously express a cellular receptor of the relaxin polypeptide. In these methods, the host cell for functional selection of the candidate scRelaxin polypeptides can also be engineered to express the receptor, e.g., HEK 293T cells expressing human RXFP1 as exemplified herein.

To identify functional scRelaxin polypeptides from the library, a reporter system is employed for detection of a phenotype evidencing signaling by the relaxin polypeptide. In the case of human relaxin-2, the reporter cell line can be one which expresses the RXFP1 receptor and also a reporter molecule (e.g., β-lactamase). The reporter cell can be the HEK293T cell line as exemplified herein or any other cells or cell lines well known in the art. Using the HEK293T cell as exemplification, expression of the RXFP1 receptor (or RXFP2, RXFP3, RXFP4) can be put under the control of an appropriate promoter sequence, e.g., the EF-1α promoter, and the reporter molecule such as β-lactamase can be expressed under the control of the cyclic AMP responsive element (CRE). Upon contacting the reporter cell line with the library of antibody-embedded scRelaxin molecules, cells with the strongest expression of the reporter molecule (e.g., β-lactamase) can be readily selected, e.g., using FACS. Functional scRelaxin agonist polypeptides or derivatives can then be isolated from the selected cells.

VI. Modified Effector Polypeptides Embedded in Antibody Scaffold

The present invention provides derivative or modified effector polypeptides that are embedded in a heterologous protein scaffold. Some of these modified effector polypeptides maintain substantially the natural biochemical or cellular activities of the embedded polypeptide. As described above, any effector polypeptides (e.g., hormones, receptor ligands or enzymes) can be used in constructing such functional derivative molecules in accordance with the methods described herein. Thus, some of the modified effector polypeptides of the invention are derived from a ligand of a cellular receptor. Some modified effector polypeptides of the invention are hormone molecules embedded in a different protein scaffold. In some embodiments, the effector polypeptide embedded in the heterologous scaffold has a molecular weight of between about 5 kDa to about 25 kDa.

In some embodiments, the host protein scaffold in the derivative effector polypeptides is an antibody scaffold. For example, some preferred embodiments of the invention utilize a scFv antibody for embedding the guest effector polypeptide. In some of these modified effector polypeptides, a complementary determining region (CDR) of the antibody scaffold is substituted with the effector polypeptide. For example, some modified effector polypeptides of the invention contain a guest polypeptide embedded into the scFv antibody scaffold of SEQ ID NO:1 by replacing the HCDR3 loop (LGITKTSTCYT; SEQ ID NO:3) of the antibody sequence.

Typically, the effector polypeptide is linked to the antibody sequence with an N-terminal linker and a C-terminal linker to maintain proper structure and biochemical or cellular functions of the inserted guest polypeptide. In various embodiments, N-terminal linker can contain an amino acid sequence Xa(GbSc)n (SEQ ID NO:86) or Xa(ScGb)n (SEQ ID NO:87), and the C-terminal linker can contain an amino acid sequence (GeSf)mXd (SEQ ID NO:88) or (SfGe)mXd (SEQ ID NO:89). In these sequences, X is any amino acid residue, G is Glycine, S is Serine, m and n are each independently a random number from 1 to 6, inclusive; a and d are each independently a random number from 1 to 5; b and e are each independently a random number from 0 to 6; and c and f are each independently a random number from 0 to 2. In addition, when multiple copies of GS rich segments are present (i.e., when n and/or m are more than 1), b, c, e or f in each GS repeat can be respectively different from b, c, e or f in the other GS repeats.

The invention also provides specific functional leptin hormone molecules or modified derivative that are embedded in an antibody scaffold. Similarly, modified FSH hormone molecules that are embedded in an antibody scaffold are also provided in the invention. The invention further provides specific functional single chain human relaxin-2 (scRelaxin-H2) agonist molecules or modified derivative that are embedded in an antibody scaffold. The antibody scaffold can be any antibody fragments that can be produced in a single chain format as described herein or well known in the art. In some embodiments, the antibody scaffold used for constructing the relaxin derivative fusions is a scFv sequence. The scFv sequence can be any known seFv antibody sequences (e.g., a known human scFv) or one that can be readily generated from the variable fragments of other immunoglobulin molecules. An exemplary human scFv scaffold antibody sequence is shown in SEQ ID NO:1. In some of these molecules, the scRelaxin-H2 polypeptide is embedded at and replaces the HCDR3 loop of the antibody scaffold.

As detailed in the Examples herein, the specific antibody scaffold embedded leptin or scFSH molecules of the invention are identified through autocrine based functional selection. These specific functional leptin or FSH derivatives possess similar or better biological and/or pharmaceutical activities relative to the native hormones. In addition to the host antibody sequence and the native hormone polypeptide sequences, these functional molecules contain specific N-terminal and C-terminal linker sequences that connect the inserted native hormone sequence and the host antibody sequence. These linker sequences are intended to ensure proper folding and maintain the biological activities. For example, some of the antibody scaffold embedded leptin molecules contain an N-terminal linker sequence and a C-terminal linker sequence that are respectively identical or substantially identical to sequences shown in (1) LGVGGGGS (SEQ ID NO:5) and GGGGSERT (SEQ ID NO:6); (2) HLTGGGGS (SEQ ID NO:7) and GSGGSGGGGSDPS (SEQ ID NO:8); (3) PWAGGGGSGGGGSGGGGS (SEQ ID NO:9) and GGGGSQPP (SEQ ID NO:10); (4) KTSGGGGSGGGGS (SEQ ID NO:11) and GGGGSSDE (SEQ ID NO:12); or (5) KVTGGGGS (SEQ ID NO:13) and GGGGSQLE (SEQ ID NO:14). Similarly, some antibody scaffold embedded scFSH molecules of the invention contain an N-terminal linker sequence and a C-terminal linker sequence that are respectively identical or substantially identical to sequences shown in (1) RSHGGGGS (SEQ ID NO:15) and GGGGSVNP (SEQ ID NO:16); (2) QRVGGGGS (SEQ ID NO:17) and GGGGSGGGGSRSA (SEQ ID NO:18); or (3) RVLGGGGS (SEQ ID NO:19) and GGGGSGGGGSQSS (SEQ ID NO:20).

Similarly, the specific antibody scaffold embedded scRelaxin-H2 molecules of the invention are also identified through functional selection. These specific functional relaxin derivatives possess similar or better biological and/or pharmaceutical activities relative to the native relaxin-H2 molecule. In addition to the host antibody sequence and the A chain and B chain sequences of the native relaxin polypeptide sequences, these functional molecules contain specific N-terminal and C-terminal linker sequences that connect the inserted native hormone sequence and the host antibody sequence. These linker sequences are intended to ensure proper folding and maintain the biological activities of the scRelaxin-H2 polypeptide. In some embodiments of the invention, the scRelaxin agonists contain a scFv antibody scaffold sequence as shown in SEQ ID NO:1 except that the LGITKTSTCYT (SEQ ID NO:3) loop in HCDR3 is replaced with the scRelaxin polypeptide. In some of these embodiments, the N-terminal linker sequence contains (comprises or consists of) a sequence XXXGGGGSGGGSGGS (SEQ ID NO:78) or XXXGGSGGS (SEQ ID NO:79), and the C-terminal linker sequence contains (comprises or consists of) a sequence SGGGGSGGGGSGXXX (SEQ ID NO:80) or SGGGGSXXX (SEQ ID NO:81), wherein X is a randomized amino acid residue.

Some specific relaxin agonist polypeptides of the invention have the scRelaxin-H2 sequence inserted into the scFv antibody scaffold with a pair of linker sequences exemplified herein. These include a N-terminal linker sequence and a C-terminal linker sequence that are respectively identical or substantially identical to sequences shown in (1) RTRGGSGGS (SEQ ID NO:50) and SGGGGSLMS (SEQ ID NO:51) (Clone A3); (2) RTRGGSGGS (SEQ ID NO:50) and SGGGGSKPP (SEQ ID NO:52) (Clone A12-2); (3) PLNGGSGGS (SEQ ID NO:53) and SGGGGSKPP (SEQ ID NO:52) (Clone C12-1); (4) LPRGGGGSGGGSGGS (SEQ ID NO:54) and SGGGGSLDS (SEQ ID NO:55); (5) QTTGGSGGS (SEQ ID NO:56) and SGGGGSKGT (SEQ ID NO:57); (6) HMFGGSGGS (SEQ ID NO:58) and SGGGGSKAP (SEQ ID NO:59); (7) QRGGGSGGS (SEQ ID NO:60) and SGGGGSWSP (SEQ ID NO:61); (8) RQRGGGGSGGGSGGS (SEQ ID NO:62) and SGGGGSVRA (SEQ ID NO:63); (9) RLTGGSGGS (SEQ ID NO:64) and SSGGWSAGGGSGVRS (SEQ ID NO:65); or (10) RNRGGGGSGGRSGGS (SEQ ID NO:66) and SGGGGSGGGGSGGRP (SEQ ID NO:67). The full length sequences of the linker-flanked scRelaxin-H2 sequences in several functional antibody embedded scRelaxin-H2 agonists exemplified herein are shown in SEQ ID NOs:68-77, respectively. In addition to the specific antibody-embedded scRelaxin polypeptides exemplified herein, the human relaxin-2 agonists of the invention also encompass antibody-embedded relaxin polypeptides that have an amino acid sequence that is substantially identical (e.g., at least 85%, 90%, 95%, 99% or higher) to the sequence of any of the exemplified agonist molecules. The agonists of the invention also include antibody-embedded relaxin molecules having terminal linker sequences that are substantially identical to the linker sequences exemplified herein, as well as antibody-embedded molecules having an inserted, terminal linker-modified scRelaxin sequence that is substantially identical to the sequence of the terminal linker-modified scRelaxin-H2 sequences exemplified herein.

The antibody scaffold embedded effector polypeptides of the invention may additionally include a peptide sequence for purification. Peptide sequences for purification that may be used are also known in the art. Examples of peptide sequences for purification include histidine tag sequences having an amino acid sequence in which at least four, and preferably at least six, continuous histidine residues, and the amino acid sequence of the glutathione-binding domain in glutathione S-transferase.

The functional effector (e.g., leptin, scFSHs and scRelaxin) polypeptides embedded in an antibody scaffold as described herein can be produced with routinely practiced recombinant methods. Such techniques are described, e.g., in Sambrook et al., *Molecular Cloning: A Laboratory Manual*, Cold Spring Harbor Press, N.Y. ($3^{rd}$ ed., 2000); and Brent et al., *Current Protocols in Molecular Biology*, John Wiley & Sons, Inc. (ringbou ed., 2003). As detailed herein, the derivative polypeptides can be produced by inserting a polynucleotide (e.g., DNA) encoding the fusion protein into an appropriate vector and introducing the expression vector into a suitable expression system.

VII. Vectors and Host Cells for Expressing Antibody Embedded Functional Polypeptides The invention provides polynucleotide sequences that encode the functional polypeptides (leptin, FSH and relaxin) embedded in an antibody scaffold as described herein, expression vectors that harbor the polynucleotide sequences, as well as host cells that harbor the polynucleotides or expression constructs. The cell can be, for example, a eukaryotic cell, or a prokaryotic cell, such as an animal cell, a plant cell, a bacterium, or a yeast. A variety of expression vector/host systems are suitable for expressing the fusion polypeptides of the invention. Examples include, e.g., microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vector (e.g., cauliflower mosaic virus, CaMV; tobacco mosaic virus, TMV) or transformed with bacterial expression vectors (e.g., Ti or pBR322 plasmid); or animal cell systems.

The selection of a particular vector depends upon the intended use of the fusion polypeptides. For example, the selected vector must be capable of driving expression of the fusion polypeptide in the desired cell type, whether that cell type be prokaryotic or eukaryotic. Many vectors contain sequences allowing both prokaryotic vector replication and eukaryotic expression of operably linked gene sequences. Vectors useful for the invention may be autonomously replicating, that is, the vector exists extrachromosomally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors and in stably transfected cell lines.

Vectors useful for the invention preferably contain sequences operably linked to the fusion polypeptide coding sequences that permit the transcription and translation of the encoding polynucleotide sequences. Sequences that permit the transcription of the linked fusion polypeptide encoding sequences include a promoter and optionally also include an enhancer element or elements permitting the strong expression of the linked sequences. The term "transcriptional regulatory sequences" refers to the combination of a promoter and any additional sequences conferring desired expression characteristics (e.g., high level expression, inducible expression, tissue- or cell-type-specific expression) on an operably linked nucleic acid sequence. The promoter sequence can be constitutive or inducible. Examples of constitutive viral promoters include the HSV, TK, RSV, SV40 and CMV promoters. Examples of suitable inducible promoters include promoters from genes such as cytochrome P450 genes, heat shock protein genes, metallothionein genes, hormone-inducible genes, such as the estrogen gene promoter, and the like. The promoter can also be tissue specific. Examples of such promoters that may be used with the expression vectors of the invention include promoters from the liver fatty acid binding (FAB) protein gene, specific for colon epithelial cells; the insulin gene, specific for pancreatic cells; the transphyretin, α1-antitrypsin, plasminogen activator inhibitor type 1 (PAI-1), apolipoprotein AI and LDL receptor genes, specific for liver cells; the myelin basic protein (MBP) gene, specific for oligodendrocytes; the glial fibrillary acidic protein (GFAP) gene, specific for glial cells; OPSIN, specific for targeting to the eye; and the neural-specific enolase (NSE) promoter that is specific for nerve cells. The selected promoter may also be linked to other sequences rendering it inducible or tissue-specific. For example, the addition of a tissue-specific enhancer element upstream of a selected promoter may render the promoter more active in a given tissue or cell type.

In addition to promoter/enhancer elements, expression vectors of the invention may further comprise a suitable terminator. Such terminators include, for example, the human growth hormone terminator, or, for yeast or fungal hosts, the TPI1 (Alber & Kawasaki, J Mol Appl Genet. 1:419-34, 1982) or ADH3 terminator (McKnight et al., 1985, EMBO J. 4: 2093-2099). Vectors useful for the invention may also comprise polyadenylation sequences (e.g., the SV40 or Ad5E1b poly(A) sequence), and translational enhancer sequences (e.g., those from Adenovirus VA RNAs). Further, a vector useful for the invention may encode a signal sequence directing the fusion polypeptide to a particular cellular compartment or, alternatively, may encode a signal directing secretion of the fusion polypeptide.

In some preferred embodiments, vectors expressing the fusion polypeptides of the invention are viral vectors, e.g., retroviral vectors or adenoviral vectors. Any viral vector that permits the introduction and expression of sequences encoding the fusion polypeptides or variants thereof in cells is acceptable for use in the methods of the invention. Viral vectors that can be used to deliver foreign nucleic acid into cells include but are not limited to retroviral vectors, adenoviral vectors, adeno-associated viral vectors, herpesviral vectors, and Semiliki forest viral (alphaviral) vectors. Defective retroviruses are well characterized for use in gene transfer (for a review see Miller, A. D. (1990) Blood 76:271). A specific example of retroviral vectors suitable for cloning and expressing the fusion polypeptides of the invention is the lentiviral vector pLV2 as exemplified herein. Protocols for producing recombinant retroviruses and for infecting cells in vitro or in vivo with such viruses can be found in Brent et al., supra, and other standard laboratory manuals.

In addition to retroviral vectors, adenovirus can be manipulated such that it encodes and expresses a gene product of interest but is inactivated in terms of its ability to replicate in a normal lytic viral life cycle (see for example Berkner et al., 1988, BioTechniques 6:616; Rosenfeld et al., 1991, Science 252:431-434; and Rosenfeld et al., 1992, Cell 68:143-155). Suitable adenoviral vectors derived from the adenovirus strain Ad type 5 d1324 or other strains of adenovirus (e.g., Ad2, Ad3, Ad7 etc.) are well known to those skilled in the art. Adeno-associated virus (AAV) is a naturally occurring defective virus that requires another virus, such as an adenovirus or a herpes virus, as a helper virus for efficient replication and a productive life cycle. (For a review see Muzyczka et al., 1992, Curr. Topics in Micro. & Immunol. 158:97-129). An AAV vector such as that described in Traschin et al. (1985, Mol. Cell. Biol. 5:3251-3260) can be used to introduce nucleic acid into cells. A variety of nucleic acids have been introduced into different cell types using AAV vectors (see, for example, Hermonat et al., 1984, Proc. Natl. Acad. Sci. USA 81: 6466-6470; and Traschin et al., 1985, Mol. Cell. Biol. 4: 2072-2081).

Depending on the specific vector used for expressing the fusion polypeptide, various known cells or cell lines can be employed in the practice of the invention. The host cell can be any cell into which recombinant vectors carrying a fusion of the invention may be introduced and wherein the vectors are permitted to drive the expression of the fusion polypeptide is useful for the invention. It may be prokaryotic, such as any of a number of bacterial strains, or may be eukaryotic, such as yeast or other fungal cells, insect or amphibian cells, or mammalian cells including, for example, rodent, simian or human cells. Cells expressing the fusion polypeptides of the invention may be primary cultured cells, for example, primary human fibroblasts or keratinocytes, or may be an established cell line, such as NIH3T3, HEK293, HEK293T HeLa, MDCK, W138, or CHO cells. Further, mammalian cells useful for expression of the fusion polypeptides of the invention may be phenotypically normal or oncogenically transformed. These include, e.g., tumor cells such as non-small cell lung cancer (NSCLC) cell line A549 or Eμ-Myc lymphoma cells as exemplified herein. Any other primary mammalian cells or transformed tumor cells may also be used in the practice of the reporter fusion polypeptides of the invention. The skilled artisans can readily establish and maintain a chosen host cell type in culture that expresses the fusion polypeptide. Many other specific examples of suitable cell lines that can be used in expressing the fusion polypeptides are described in the art. See, e.g., Smith et al., 1983., J. Virol 46:584; Engelhard, et al., 1994, Proc Nat Acad Sci 91:3224; Logan and Shenk, 1984, Proc Natl Acad Sci, 81:3655; Scharf, et al., 1994, Results Probl Cell Differ, 20:125; Bittner et al., 1987, Methods in Enzymol, 153:516; Van Heeke & Schuster, 1989, J Biol Chem 264:5503; Grant et al., 1987, Methods in Enzymology 153:516; Brisson et al., 1984, Nature 310:511; Takamatsu et al., 1987, EMBO J 6:307; Coruzzi et al., 1984, EMBO J 3:1671; Broglie et al., 1984, Science, 224:838; Winter J and Sinibaldi R M, 1991, Results Probl Cell Differ., 17:85; Hobbs S or Murry L E in McGraw Hill Yearbook of Science and Technology (1992) McGraw Hill New York N.Y., pp 191-196 or Weissbach and Weissbach (1988) Methods for Plant Molecular Biology, Academic Press, New York, pp 421-463.

The fusion polypeptide-expressing vectors may be introduced to selected host cells by any of a number of suitable methods known to those skilled in the art. For example, vectors expressing the fusion polypeptide may be introduced into appropriate bacterial cells by infection, in the case of *E. coli* bacteriophage vector particles such as lambda or M13, or by any of a number of transformation methods for compatible plasmid vectors or for bacteriophage DNA. For example, standard calcium-chloride-mediated bacterial transformation is still commonly used to introduce naked DNA to bacteria (Sambrook et al., supra), but electroporation may also be used (Brent et al., supra). For co-transformation of fusion genes into *E. coli*, two different compatible plasmid expression vectors need to be used each containing different antibiotic resistance genes.

For the introduction of constructs expressing the antibody scaffold embedded polypeptides into yeast or other fungal cells, chemical transformation methods are generally used (e.g. as described by Rose et al., 1990, Methods in Yeast Genetics, Cold Spring Harbor Laboratory Press, Cold Spring Harbor, N.Y.). For transformation of *S. cerevisiae*, for example, the cells are treated with lithium acetate to achieve transformation efficiencies of approximately 104 colony-forming units (transformed cells)/μg of DNA. Transformed cells are then isolated on selective media appropriate to the selectable marker used. Alternatively or additionally, plates or filters lifted from plates may be scanned for fluorescence and luciferase-mediated bioluminescence to identify transformed clones with the fusion polypeptide-encoding constructs.

For the introduction of fusion polypeptide-encoding vectors to mammalian cells, the method used will depend upon the form of the vector. For plasmid vectors, DNA encoding the fusion polypeptide sequences may be introduced by any of a number of transfection methods, including, for example, lipid-mediated transfection ("lipofection"), DEAE-dextran-mediated transfection, electroporation or calcium phosphate precipitation. These methods are detailed, for example, in Brent et al., supra. Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

For long-term, high-yield production of recombinant fusion polypeptides, stable expression is preferred. Rather than using expression vectors which contain viral origins of replication, host cells can be transformed with the fusion polypeptide-encoding sequences controlled by appropriate expression control elements (e.g., promoter, enhancer, sequences, transcription terminators, polyadenylation sites, etc.), and selectable markers. The selectable marker in the recombinant vector confers resistance to the selection and allows cells to stably integrate the vector into their chromosomes. Commonly used selectable markers include neo, which confers resistance to the aminoglycoside G-418 (Colberre-Garapin, et al., J. Mol. Biol., 150:1, 1981); and hygro, which confers resistance to hygromycin (Santerre, et al., Gene, 30: 147, 1984). Through appropriate selections, the transfected cells can contain integrated copies of the fusion polypeptide encoding sequence.

A number of other selection systems may also be used, including but not limited to the herpes simplex virus thymidine kinase (Wigler, et al., Cell, 11: 223, 1977), hypoxanthine-guanine phosphoribosyltransferase (Szybalska & Szybalski, Proc. Nati. Acad. Sci. USA, 48:2026, 1962), and adenine phosphoribosyltransferase (Lowy, et al., Cell, 22:

817, 1980) genes. Also, antimetabolite resistance can be used as the basis of selection for dhfr, which confers resistance to methotrexate (Wigler, et al., Proc. Natl. Acad. Sci. USA, 77: 3567, 1980; O'Hare, et al., Proc. Natl. Acad. Sci. USA, 8: 1527, 1981); gpt, which confers resistance to mycophenolic acid (Mulligan & Berg, Proc. Natl. Acad. Sci. USA, 78: 2072, 1981). Further, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

VIII. Therapeutic Applications and Pharmaceutical Compositions

The functional effector polypeptides embedded in another protein scaffold described herein can find many therapeutic or prophylactic applications. For example, the functional leptin derivative polypeptides of the invention can be employed in the treatment and prevention of various conditions or diseases in which leptin deficiency plays a role. These include many disorders associated with or mediated by insufficient or abnormal leptin activities in the regulation of energy balance, body weight, metabolism, and endocrine function, e.g., common obesity, lipodystrophy, hypothalamic amenorrhea, and congenital leptin deficiency. Similarly, the functional scFSH polypeptides embedded in the host protein scaffold as described herein can be used in treating conditions associated with low or diminished FSH levels. Diminished secretion of FSH can result in failure of gonadal function (hypogonadism). This condition is typically manifested in males as failure in production of normal numbers of sperm. In females, cessation of reproductive cycles is commonly observed. Specific examples of conditions associated with low FSH levels include polycystic ovarian syndrome, Kallmann syndrome, hypothalamic suppression, hypopituitarism, hyperprolactinemia, and gonadotropin deficiency. Subjects afflicted with or at risk of developing any of these and other conditions are amenable to treatment with the functional scFSH derivative polypeptides of the invention.

Similarly, the functional scRelaxin polypeptides embedded in another protein scaffold described in the invention can also find many therapeutic or prophylactic applications. For example, the functional human scRelaxin-H2 agonists exemplified herein can be employed in the treatment and prevention of various conditions or diseases for which enhanced relaxin-2 signaling is desired. Such diseases or conditions include, e.g., acute heart failure, chronic heart failure, congestive heart failure, pulmonary hypertension, scleroderma, duchene muscular dystrophy, liver fibrosis, renal fibrosis, pulmonary fibrosis, non-alcoholic steatohepatitis (NASH), non-alcoholic fatty liver disease (NAFLD), skeletal muscle injury, trauma, burn, fibromyalgia, and solid or metastatic tumors. Other disorders that are amenable to treatment with the relaxin agonists of the invention include, e.g., osteodegeneration, joint pain, other pains, Alzheimers disease, Type 2 diabetes, multiple sclerosis, renal vasodilation, and Dupuytren's disease.

In some embodiments, the compositions and methods described herein are employed to treat cancers or tumors. These include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, colon, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

The antibody scaffold embedded functional polypeptides described herein (e.g., leptin, scFSH or scRelaxin) can be used in either prophylactic or therapeutic applications. In prophylactic applications, pharmaceutical compositions or medicaments are administered to a subject susceptible to, or otherwise at risk of, developing a disease or condition (i.e., obesity, scleroderma or heart failure) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or drugs are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. Often, the therapeutic benefit is monitored and repeated dosages are given if the benefit starts to wane.

The antibody scaffold embedded functional polypeptides for use in the methods of the invention should be administered to a subject in an amount that is sufficient to achieve the desired therapeutic effect (e.g., eliminating or ameliorating symptoms associated with a relevant condition). An amount adequate to accomplish therapeutic or prophylactic treatment is defined as a therapeutically- or prophylactically-effective dose. Thus, a therapeutically- or prophylactically-effective dose or efficacious dose of the functional derivative effector polypeptide is employed in the pharmaceutical compositions of the invention. In both prophylactic and therapeutic regimes, agents are usually administered in several dosages until a sufficient benefit has been achieved. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular compositions of the present invention employed, the route of administration, the time of administration, and the rate of excretion of the particular compound being employed. It also depends on the duration of the treatment, other drugs, compounds and/or materials used in combination with the particular compositions employed, the age, gender, weight, condition, general health and prior medical history of the subject being treated, and like factors. Methods for determining optimal dosages are described in the art, e.g., Remington: The Science and Practice of Pharmacy, Mack Publishing Co., 20th ed., 2000. Typically, a pharmaceutically effective dosage would be between about 0.001 and 100 mg/kg body weight of the subject to be treated.

Typically, the antibody scaffold embedded functional polypeptides of the invention are formulated in pharmaceutical compositions for the therapeutic or prophylactic applications disclosed herein. The pharmaceutical compositions can be prepared in various forms, such as granules, tablets, pills, suppositories, capsules, suspensions, salves, lotions and the like. The pharmaceutical compositions typically contain a therapeutically effective amount of the active effector polypeptide (e.g., leptin, scFSH or scRelaxin derivative polypeptide of the invention). The concentration of therapeutically active compound in the formulation may vary from about 0.1-100% by weight. In addition to the active effector polypeptide, the compositions may contain pharmaceutically acceptable carriers and other ingredients known to facilitate administration and/or enhance uptake. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for molecules of the invention include ethylene-vinyl acetate copolymer particles, osmotic pumps, implantable infusion systems, and liposomes. Formulations for inhalation may contain excipients, for example, lactose, or may be aqueous solutions containing, e.g., polyoxyethylene-9-lauryl ether, glycocholate and deoxycholate, or may be oily solutions for administration in the form of nasal drops, or as a gel. Therapeutic formulations are prepared by any methods well known in the art of pharmacy. The therapeutic formulations can be delivered by any effective means which could be used for treatment. See, e.g., *Goodman & Gilman's The Pharmacological Bases of Therapeutics*, Hardman et al., eds., McGraw-Hill Professional (10th ed., 2001); *Remington: The Science and Practice of Pharmacy*, Gennaro (ed.), Lippincott Williams & Wilkins (20th ed., 2003); and *Pharmaceutical Dosage Forms and Drug Delivery Systems*, Ansel et al. (eds.), Lippincott Williams & Wilkins (7th ed., 1999). Pharmaceutical compositions are preferably manufactured under GMP conditions.

The pharmaceutical compositions are usually administered to the subjects on multiple occasions. Intervals between single dosages can be daily, weekly, monthly or yearly. Intervals can also be irregular as indicated by measuring blood levels of the derivative effector polypeptide and the other therapeutic agents used in the subject. In some methods, dosage is adjusted to achieve a plasma concentration of 1-1000 µg/ml, and in some methods 25-300 µg/ml or 10-100 µg/ml. Alternatively, the therapeutic agents can be administered as a sustained release formulation, in which case less frequent administration is required. Dosage and frequency vary depending on the half-life of the effector polypeptide and the other drugs in the subject. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

The invention also provides kits for carrying out the therapeutic applications disclosed herein. For example, the invention provides therapeutic kits for use in the treatment of subjects afflicted with disorders described herein, e.g., conditions associated with a deficiency in leptin, FSH or relaxin. The therapeutic kits of the invention typically comprise as active agent one or more of the described functional polypeptides. The kits can optionally contain suitable pharmaceutically acceptable carriers or excipients for administering the active agents. The pharmaceutically acceptable carrier or excipient suitable for the kits can be coatings, isotonic and absorption delaying agents, binders, adhesives, lubricants, disintergrants, coloring agents, flavoring agents, sweetening agents, absorbants, detergents, and emulsifying agents. Other reagents that can be included in the kits include antioxidants, vitamins, minerals, proteins, fats, and carbohydrates.

The therapeutic kits can further include packaging material for packaging the reagents and a notification in or on the packaging material. The kits can additionally include appropriate instructions for use and labels indicating the intended use of the contents of the kit. The instructions can be present on any written material or recorded material supplied on or with the kit or which otherwise accompanies the kit.

The therapeutic kits of the invention can be used alone in the treatment of one of the noted disorders for each of the exemplified functional polypeptides (e.g., leptin, FSH or relaxin). They can also be used in conjunction with other known therapeutic regiments. For example, subjects suffering from obesity can use the therapeutic kit along with anther obesity drug (e.g., Xenical). The therapeutic composition of the invention and other known treatment regimens can be administered to the subjects sequentially or simultaneously. These therapeutic applications of the invention can all be indicated on the instructions of the kits.

EXAMPLES

The following examples are provided to further illustrate the invention but not to limit its scope.

Example 1. Choice of Guest Molecules

To determine whether the combinatorial process of inserting guests into protein hosts could be general, we studied two very different protein hormones, Leptin and Follicle stimulating hormone (FSH). Hormones were selected as test objects because one can determine easily whether they are functional when incorporated into the host molecules. Each hormone brings special advantages and disadvantages to the problem. Leptin is a 146 amino acid long protein that is folded into a compact 4-helix bundle (Zhang et al., *Nature* 387, 206-209, 1997). The strong binding energy of the helices for each other may make selection of junctions less critical. But, this same rigidity of the guest may interfere with the pathway by which the entire complex folds. FSH has 203 amino acids that fold mostly into β-sheet secondary structures. In terms of these experiments, FSH's special problem is that it is a heterodimer. If the FSH monomeric subunits are treated individually, the process becomes a four linker combinatorial problem whereas if the monomeric subunits of the heterodimer are covalently linked, the process is reduced to a three linker combinatorial problem. Thus, a single chain FSH (scFSH) was constructed by linking the two subunits using a GSGSNATGSGSNATSGSTS (SEQ ID NO:33) peptide linker. Initially, the scFSH covalent dimer was shown to be functional using a reporter cell line (see below).

Example 2. Construction of Combinatorial Junctions

The host scaffold is an antibody with a CDR H3 containing 19 amino acid residues (Kabat numbering). To maintain proper folding of the antibody core, while maximizing the flexibility of junctions, the LGITKTSTCYT loop (SEQ ID NO:3), which is the core of CDR H3, was replaced by members of the combinatorial N- and C-terminal junction library to generate a highly diverse array of sequences that flank the Leptin and scFSH guests. This choice of site of insertion was based on the homology model of the parental scaffold. In this construct, some of the base of the guest is expected to pack against some of the other unaltered CDRs of the host antibody with the remainder extending into the solvent.

The combinatorial junction library was designed to contain junctions of a random 3-residue linker and 1 to 3 copies of a GGGGS (SEQ ID NO:4) linker at both the N- and C-terminus of Leptin and scFSH. The diversity of protein junctional sequence space is $2.88 \times 10^7$ for a combination of the N- and C-terminus libraries. To construct the library, a PCR was conducted using combinations of three forward primers, which contain a random XXX linker followed by a $(GGGGS)_{1-3}$ (SEQ ID NO:34) linker and a sequence complimentary to the guest hormones, and three reverse primers, that contain a sequence complimentary to the guest followed by a $(GGGGS)_{1-3}$ (SEQ ID NO:34) linker and a XXX linker. The amplified PCR products were digested and transferred into the parental scaffold antibody. The quality and diversity of both libraries were confirmed by sequencing of twenty colonies.

Example 3. Construction of Reporter Cell Lines

Autocrine-based flow cytometry sorting of cells in which the expression of β-lactamase reporter gene is induced by various cell signaling responsive elements has been widely used because of its high accuracy and sensitivity. To construct such a reporter cell line for the human Leptin receptor (LepR), the CellSensor SIE-Bla HEK293T cells (Life Technology) that can express the β-lactamase reporter gene under the control of Sis-Inducible Element (SIE), were transduced with lentiviruses expressing the C-terminal HA tagged human LepR gene driven by the elongation factor-1 alpha (EF1α) promoter (FIG. 1A). Single clones after sorting based on response to human Leptin protein were tested and the one with the strongest response was denoted as LepR SIE-Bla cells and used for further studies. The LepR SIE-Bla cells stably express the HA-tagged human Leptin receptor (FIG. 1B) and have a response ratio of 8.5 for human Leptin in a fluorescence resonance energy transfer (FRET) assay (FIG. 1C). The response ratio is the signal generated in the LepR SIE-Bla cells divided by the signal of the cells without the LepR.

To construct the reporter cell line for the human FSHR, HEK 293T cells were co-transduced with lentiviruses stably expressing the C-terminal HA tagged human scFSH gene, and lentiviruses expressing the β-lactamase gene under the control of the cyclic AMP responsive element (CRE) (FIG. 1D). The transduced cells were exposed to recombinant human FSH protein and sorted to select those that respond best. The FSHR CRE-Bla cells have a response ratio of 6.4 to human FSH protein in the FRET assay (FIG. 1E).

Example 4. Autocrine Based Selection of Functional Junctions

To isolate functional antibody clones, FRET-based FACS sorting was carried out using stringent gating. LepR SIE-Bla and FSHR CRE-Bla cells were transduced with the corresponding lentiviral combinatorial junction libraries at multiplicity of infection of about 2. Lentiviruses were removed 5 hours after infection, and methylcellulose media was placed on top of cells to limit diffusion of secreted antibodies to neighboring cells. Twenty hours after lentivirus infection, the methylcellulose media was washed away with media and cells were trypsinized, loaded with LiveBLAzer-FRET B/G Substrate, and sorted.

For LepR SIE-Bla cells, there was significant enrichment after two rounds of sorting, from only 0.06% positive cells in the first round to 3.30% positive cells in the second round. For FSH CRE-Bla cells, one round of sorting yielded 0.18% positive cells. After each round of sorting, antibody gene fragments were recovered by the PCR using cell lysates as templates, and re-inserted into the lentiviral vector for the next round of sorting, if necessary. Twenty clones were picked from the second round for LepR SIE-Bla cells, and after the first round for FSHR CRE-Bla cells. Plasmids were extracted from these clones and transfected into HEK 293T cells to express secreted antibodies. The supernatants from the Leptin and FSH sorting were tested two days after transfection to identify positive clones. From their respective cell sorts, six clones out of 14 were capable of activating LepR SIE-Bla cells, and 3 clones out of 14 were positive for activation of FSHR CRE-Bla cells. These clones were sequenced and the sequences of permissive junctions were analyzed (Tables 1 and 2).

TABLE 1

Active agonist clones for LepR

| Clones | N linker (SEQ ID NO:) | C linker (SEQ ID NO:) |
|---|---|---|
| A | HLTGGGGS (7) | GSGGSGGGGSDPS (8) |
| B | PWAGGGGSGGGGSGGGGS (9) | GGGGSQPP (10) |
| C | LGVGGGGS (5) | GGGGSERT (6) |
| D | KTSGGGGSGGGGS (11) | GGGGSSDE (12) |
| E | LGVGGGGS (5) | GGGGSERT (6) |
| F | KVTGGGGS (13) | GGGGSQLE (14) |

TABLE 2

Active agonist clones for FSHR

| Clones | N linker (SEQ ID NO:) | C linker (SEQ ID NO:) |
|---|---|---|
| A | RSHGGGGS (15) | GGGGSVNP (16) |
| B | QRVGGGGS (17) | GGGGSGGGGSRSA (18) |
| C | RVLGGGGS (19) | GGGGSGGGGSQSS (20) |

Out of the six active antibody clones containing the Leptin guest, the two most active clones (clone C and E in Table 1) had identical N-terminal (LGVGGGGS) (SEQ ID NO:5) and C-terminal sequences (GGGGSERT) (SEQ ID NO:6). The other four active clones had apparently random unrelated sequences. Interestingly, this N-terminal junction sequence (LGVGGGGS) is highly similar to a typical Glycine-rich loop. The consensus GxGxxG (SEQ ID NO:39) motif appears in natural proteins, such as LGVGGGS (SEQ ID NO:40) in NADH-dependent butanol dehydrogenase A (PDB code: 1VLJ) and IGVGGGGS (SEQ ID NO:41) in the prokaryotic cell division protein FtsZ (PDB code: 2R6R), which are preceded by a β-strand and followed by an α-helix. Interestingly, the consensus GxGxxG sequence is a phosphate binding motif where phosphate binding is thought to stabilize the helix.

The expression level and agonistic activity against FSHR of the three active scFSH clones were tested. Clone B was the most active. Interestingly, the N-terminal junction sequence (QRVGGGGS) (SEQ ID NO:17) contains the sequence (RVGGG) (SEQ ID NO:90), which exists in the natural 40S ribosomal protein S5 where it forms β/β junctions (PDB codes: 1S1H, 3JYV).

Example 5. Improved Selection of Junctions

While the first selection yielded functional proteins, their production was not optimal. In an attempt to select clones with improved protein production, another selection was carried out in which a protein yield parameter was incorporated. To accomplish this, a new vector was used where the gene encoding mCherry was fused to the C-terminus of the scFv gene. This allowed us to select for high expressing clones by using an additional gate for high mCherry signal prior to the FRET gate. Three libraries were studied. One was the original library. In the other two libraries, either the N- or the C-terminal linkers were held constant from the previous selection and the other linkers were again random. This selection yielded a new clone (clone 2) with RHMGGGGS (SEQ ID NO:37) at the N-terminus and GGGGSGGGGSTDT (SEQ ID NO:38) at the C-terminus. This protein expressed much better than the previously selected clones while retaining full Leptin activity.

Example 6. In Vitro Activity

Figure 3:
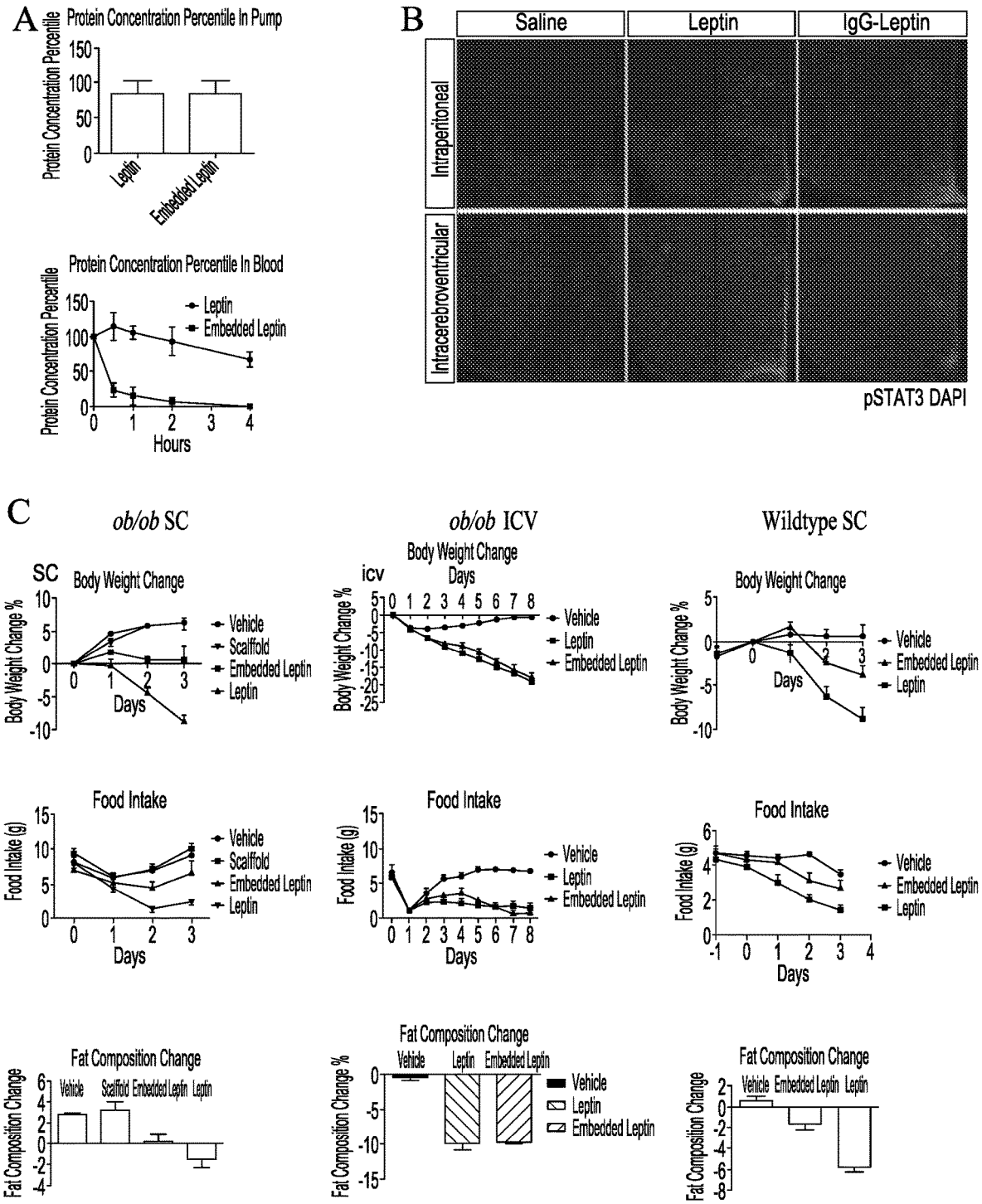
FIGS. 3A-3C show that IgG-Leptin regulates metabolism in vivo. A, IgG-Leptin is stable at body temperature with increased half-life in circulation. Upper panel, Leptin or IgG-Leptin was loaded into osmotic pumps, which were implanted subcutaneously. The concentration of Leptin and IgG-Leptin inside of the pumps was measured by ELISA at 3 days after the implantation. Lower panel, a single dose of Leptin or IgG-Leptin was administrated via the jugular vein, and protein concentration in plasma was determined through orbital bleeding at various time points. B, IgG-Leptin activates STAT3 in the hypothalamus. Leptin or IgG-Leptin was administrated peripherally or centrally, and neuronal activation of STAT3 in the hypothalamus was examined by immunohistochemistry. C, IgG-Leptin exerts a metabolic function in vivo. Leptin or IgG-Leptin was administrated peripherally or centrally into ob/ob mice, or peripherally into wildtype mice. Body weight and food intake were recorded at indicated time points before and after the treatment. Body fat composition was measured at beginning and end points of treatment.

The most active and best producing scFv clone of the antibody containing the Leptin guest was converted into a Fab format (Fab-Leptin) or full IgG format (IgG-Leptin). The unaltered scaffold, Fab-Leptin and IgG-Leptin were cloned in pFUSE-based vectors (InvivoGen) and expressed in FreeStyle 293-F cells (Life Technologies). After a one-step affinity purification, all antibodies were purified to high purity. The activity of purified antibodies was tested in two different assays. In the FRET assay using the β-lactamase-based LepR SIE-Bla cell line, the measured $EC_{50}$ of Fab-Leptin, IgG-Leptin and native Leptin were 118.3 pM, 58.7 pM and 313.4 pM, respectively (FIG. 2A). In the proliferation assay using the Baf3 LepR cell line whose growth is dependent on IL-3 or Leptin, the $EC_{50}$ of Fab-Leptin, IgG-Leptin and native Leptin were 131.9 pM, 37.2 pM and 309.6 pM, respectively (FIG. 2B).

To test the activity of the most active clone of the antibody containing scFSH, it was converted to IgG-scFSH using the same strategy as for IgG-Leptin. The scFSH was also cloned into the pFUSE-based vector and produced as for IgG-scFSH. Both scFSH and IgG-scFSH of high purity were obtained after a one-step affinity purification. Their activity was measured by a FRET assay using the β-lactamase-based FSHR CRE-Bla cell line. The $EC_{50}$ of IgG-scFSH, scFSH and native FSH were 5.5 pM, 5.7 pM and 4.6 pM, respectively (FIG. 2C).

Example 7. Structure and Dynamics of the Leptin Host-Guest Construct

Circular Dichroism (CD) spectroscopy is a very valuable tool in structural biology for rapid determination of the secondary structure and folding properties of protein and peptides. To examine whether IgG-Leptin folds naturally like the antibody scaffold, far-ultraviolet (UV) CD spectroscopy of both antibody scaffold and IgG-Leptin was measured. Both the antibody scaffold and IgG-Leptin have negative peaks near 217 nm and positive peaks near 195 nm, which is consistent with the fact that antibodies are composed of all β-sheet secondary structures. The similar CD spectroscopy pattern indicates that the host component of IgG-Leptin folds naturally. As expected, the antibody containing the Leptin guest had a stronger peak at 195 nm and 217 nm corresponding to the α-helical signals.

Next, we used differential hydrogen-deuterium exchange mass spectrometry (HDX-MS) to investigate the conformational dynamics and stability of Leptin in its free form versus when it is integrated into antibody scaffold (IgG-Leptin). We first compared the intrinsic deuterium uptake dynamics of Leptin to the IgG-Leptin construct. HDX kinetics of 63 peptic peptides covering ~85% of the Leptin sequence (IgG-Leptin or Leptin alone) were measured and the average percent deuterium incorporation for each peptide in the Leptin and IgG-Leptin was calculated based on triplicate analysis of six on-exchange time points (see methods). Analysis of the HDX data reveals that the average deuterium uptake for the two Leptin variants remained very similar for most protein regions with residues 51-66, 81-93, and 124-138 heavily protected against exchange to solvent deuterium in both the Leptin variants. However, amino acid residues 18-52 and 67-80 are more accessible to deuterium exchange (yellow/green/red regions) indicating more conformational flexibility in this region in both the Leptin variants. This suggests that the overall topological conformation of Leptin is highly similar between the free and IgG-Leptin.

To further characterize conformational differences between the free Leptin and IgG-Leptin, we next examined the differences in deuterium uptake dynamics between the two Leptin variants. Differential rates at which amide hydrogen exchanges with solvent deuterium can reveal information about the conformational differences between the two Leptin variants. Analysis of the differential HDX data revealed that the average deuterium uptake for the free and embedded Leptin variants remains very similar for most protein regions. These data further corroborate both the in vitro and in vivo (see below) activity and suggest that the conformation of Leptin is unaltered between the free from and IgG-Leptin. In addition, residues 43-54 show increased protection to deuterium uptake in the free Leptin as compared to IgG-Leptin. While this suggests that this protein region is more conformationally rigid in the free Leptin form compared to IgG-Leptin, HDX behavior for majority of the protein regions remains unaltered indicating that two Leptin forms are essentially the same.

Example 8. In Vivo Activity

With the in vitro results demonstrating that IgG-Leptin fully retains the Leptin signaling activity, we were prompted to characterize the functionality of IgG-Leptin in vivo. We examined the protein stability of IgG-Leptin at the body temperature of mice. Leptin or IgG-Leptin was loaded into osmotic pumps, which were then implanted subcutaneously (SC) into mice. We observed that 3 days after the implantation, the concentration of both Leptin and IgG-Leptin inside of the pumps remained constant as measured by ELISA, showing that, similar to Leptin, IgG-Leptin is stable at this condition thereby allowing long-term in vivo administration. Next, since antibodies generally exhibit a long half-life in circulation, we reasoned that embedding Leptin into the antibody scaffold might increase the half-life of the hormone, which by itself is rapidly cleared by kidney and other peripheral organs. To test this, a single dose of Leptin or IgG-Leptin was administered via the jugular vein, and rate of the protein clearance was determined at various time points. Leptin protein showed a half-life of less than half an hour as expected, but in contrast, IgG-Leptin had a significantly increased half-life in plasma, with over 50% of the protein remaining at 4 hours post administration (FIG. 3A). This decreased clearance could be due to region(s) surrounding the embedded Leptin in IgG-Leptin, which interfere with the binding of Leptin with its clearance receptors such as megallin. Together the data show that compared to Leptin, IgG-Leptin has a similar level of protein stability at body temperature and a prolonged half-life in circulation, which makes it a valid candidate for metabolic modulation in vivo.

While IgG-Leptin is able to potently activate the Leptin signaling in vitro, embedding of Leptin into the antibody scaffold produced a dimeric molecule of 187.2 kDa, which is much larger than the original monomeric 16-kDa hormone. It raised the possibility that IgG-Leptin administrated peripherally may not be able to penetrate the blood-brain-barrier efficiently and to get access to Leptin-responsive neurons in the central nervous system. To address this question, we first compared neuronal activation in the hypothalamus in response to central treatment of IgG-Leptin. Following the intracerebral ventricular (ICV) injection of IgG-Leptin, which directly delivers the protein into the ventricles, there was a robust phosphorylation of STAT3 in multiple regions in the hypothalamus. STAT3 activation in neurons adjacent to the ventricles was comparable to that observed with the ICV injection of equal molar amount of Leptin, consistent with the in vitro data that IgG-Leptin fully retains the signaling function of Leptin (FIG. 3B). The relatively weaker STAT3 activation in neurons farther distant from the ventricle possibly reflects a slower diffusion of IgG-Leptin through the tissue. Of note, consistent with Leptin being actively transported into the central nervous system, peripheral administration of Leptin resulted in the pattern of STAT3 activation similar to that seen after central delivery. In contrast, while peripheral administration of IgG-Leptin could also induce STAT3 phosphorylation, it was confined to the neurons in the arcuate nucleus (ARC) but peculiarly absent from other neuronal populations in the hypothalamus that were activated by the central administration of IgG-Leptin. One potential explanation to this intriguing result is that dendritic protrusions of the pro-opiomelanocortin and neuropeptide Y/agouti-related protein neurons in the ARC are known to project in close proximity to the median eminence and are able to directly sense circulating molecules in plasma, therefore bypassing the need for transportation across the blood-brain-barrier. Peripherally administrated IgG-Leptin could probably use this mechanism to activate the ARC neurons. The results together show that IgG-Leptin can activate Leptin-responsive neurons in the hypothalamus, albeit the antibody scaffold does compromise the ability of IgG-Leptin to penetrate the brain-blood-barrier.

Figure 4:
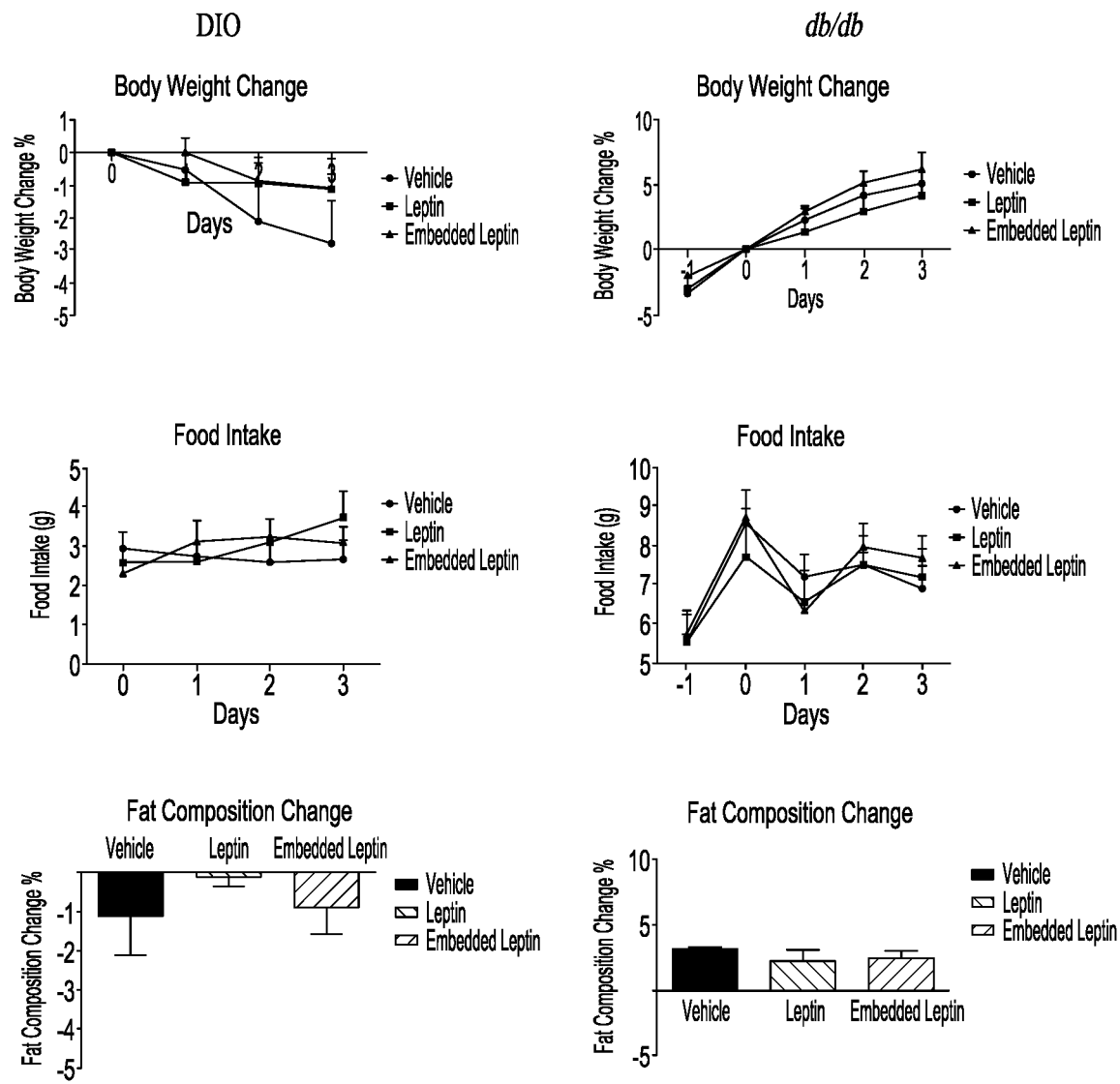
FIG. 4 shows that metabolic effect of IgG-Leptin is abolished in db/db or DIO mice. Leptin or IgG-Leptin was administrated peripherally into db/db or DIO mice. Body weight and food intake were recorded at indicated time points before and after the treatment. Body fat composition was measured at beginning and end points of treatment.
Figure 5:
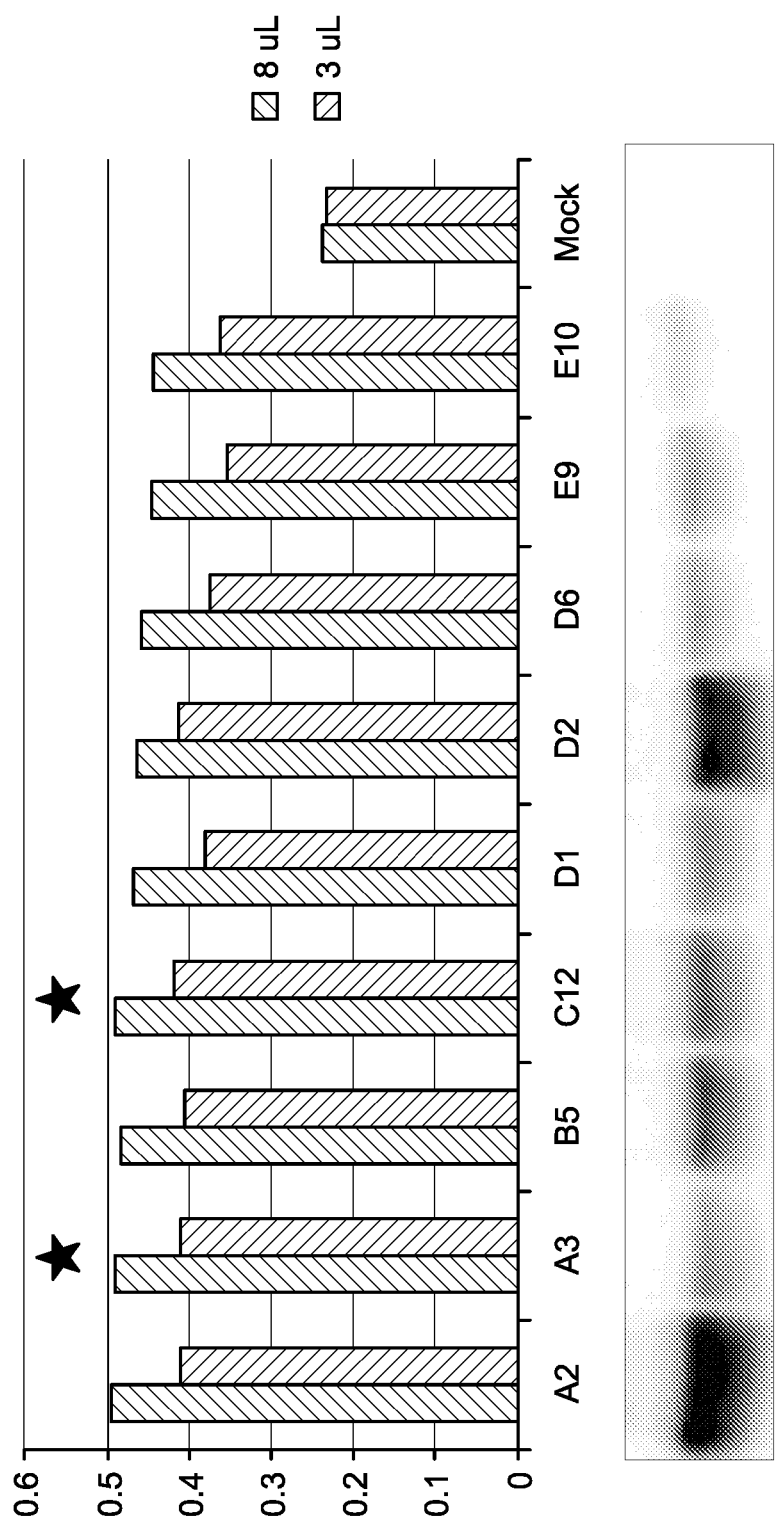
FIG. 5 shows agonist activities of 9 antibody scaffold scRelaxin clones and their expression levels in cell culture supernatant.
Figure 7:
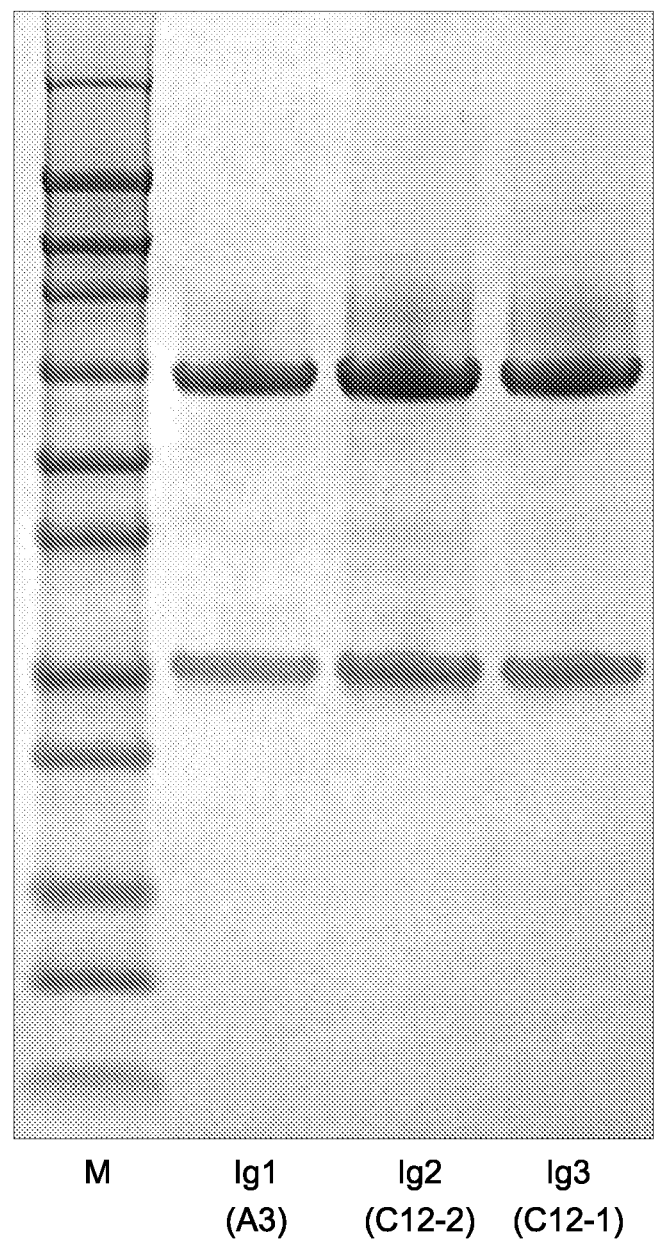
FIG. 7 shows purified antibody-embedded scRelaxin agonist molecules, A3, C12-2 and C12-1, in Coomassie blue stained SDS-PAGE gel.
Figure 8:
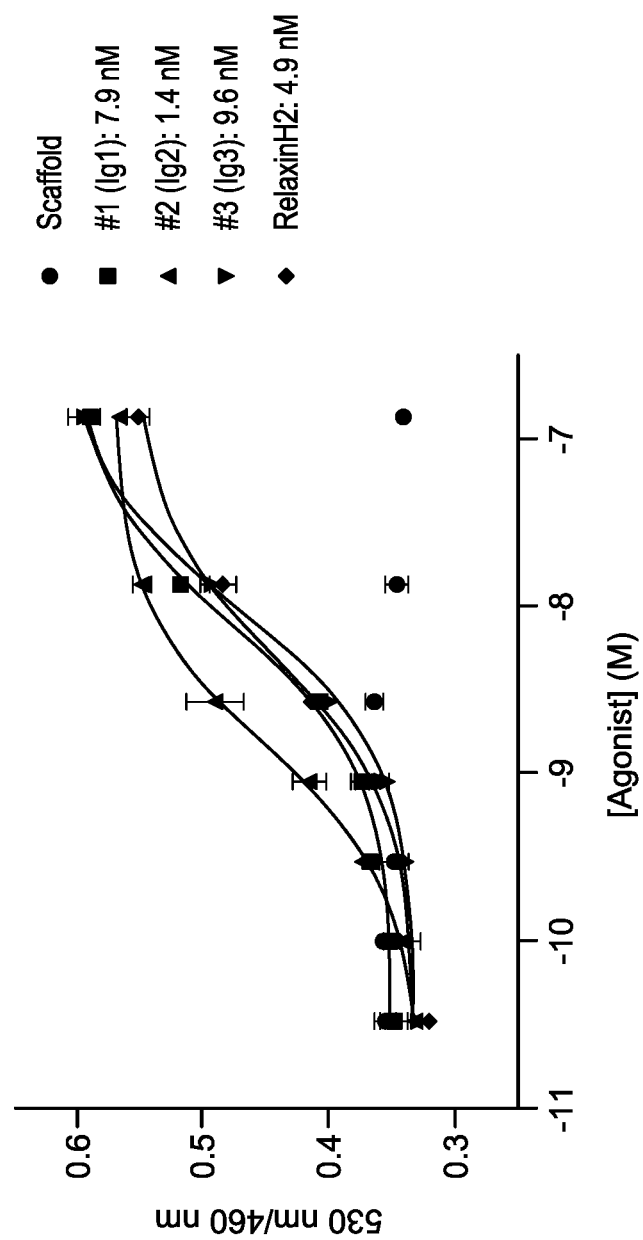
FIG. 8 shows in vitro activities of purified antibody-embedded scRelaxin agonist molecules A3, C12-2 and C12-1.
Figure 9:
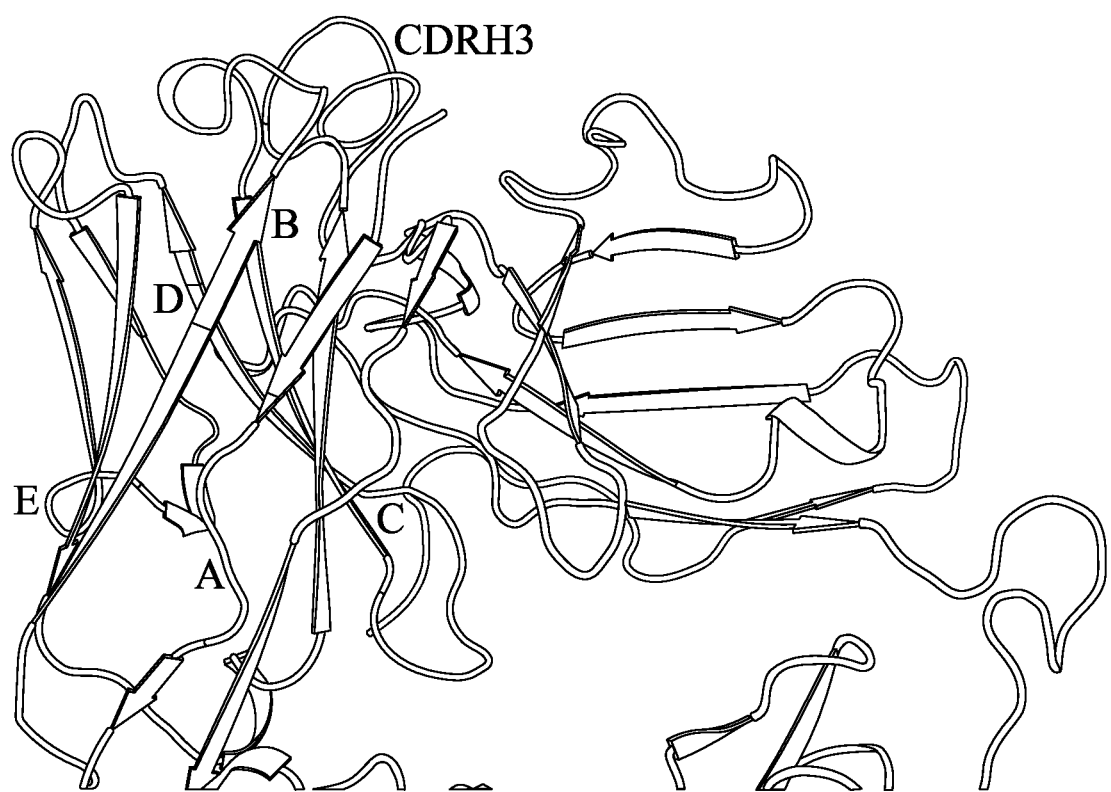
FIG. 9 shows the structure of a scFv antibody scaffold and five sites thereon for substituting a short random peptide to study tolerance of insertion of a guest sequence outside CDR regions of the antibody scaffold.

ARC neurons have critical roles in regulating satiety and energy expenditure. To examine whether activation of the ARC neurons by IgG-Leptin was sufficient to elicit a metabolic effect, the protein was peripherally delivered into obese mice via subcutaneous osmotic pumps. Interestingly, compared to vehicle control, IgG-Leptin could significantly reduce food intake as well as body weight following the administration (FIG. 3C left panel). This observation demonstrates that despite only being able to activate Leptin-responsive neurons in the ARC, peripheral IgG-Leptin can still exert the catabolic function, although we did notice that the potency of IgG-Leptin was modestly weaker compared to the equal molar amount of Leptin. On the other hand, when IgG-Leptin was chronically delivered into intracerebral ventricles of ob/ob mice through brain infusion pump, it reduced food intake and body weight to the comparable extent as Leptin (FIG. 3C middle panel). IgG-Leptin could also lead to the decrease of food intake, body weight and fat composition in wildtype mice (FIG. 3C right panel), but not in diet-induced-obese (DIO) mice (FIG. 4 left panel) or db/db mice (FIG. 4 right panel), excluding the possibility that the catabolic effect of IgG-Leptin might be due to some non-specific toxicity. Together, our in vivo results show that IgG-Leptin retains the signaling function of leptin, and can activate leptin-responsive neurons in the hypothalamus to regulate the metabolism.

Example 9. Tolerance of Guest Insertion Outside CDR Regions of Antibody Scaffold This Example describes insertions of guest peptides into an antibody scaffold outside the CDR regions. Successful construction of host-guest polypeptides fusion molecules is a function of at least two parameters. Firstly, one has to answer which position that allows substitution. And secondly, what linkers are permissive. To explore additional sites in the host scaffold that are permissive for insertion of guest polypeptides, we carried out a comprehensive study by examining tolerance of the functional leptin embedded in a scFv antibody scaffold as described above to insertions of short peptides at other sites. Specifically, the functional scFv embedded leptin fusion molecule was modified by substituting a library of 4-residue randomized peptides at each of 5 different positions in the scFv scaffold. The DNA fragments coding the library of 4-residue randomized peptides were designed using the classic NNK strategy (Barbos et al., Proc. Natl. Acad. Sci. USA 90:10003-10007, 1993). The 5 original peptides in the scFv scaffold that were replaced by the substitutions are segments H6-H9 (A), H23-H26 (B), H36-H39 (C), H47-H50 (D), and H64-H67 (E) in accordance with the Kabat numbering (as shown in FIG. 9). This resulted in 5 libraries of the scFv-leptin fusion molecules that are modified at each of the 5 non-CDR positions with the 4-residue random peptide sequences. Lentiviruses of these five libraries were produced and infected into the LepR SIE-Bla cells.

Autocrine-based flow cytometry analysis was then carried out, with leptin in the antibody scaffold as a functional probe. Cells containing functional population of lentiviruses, as indicated by leptin activity, in each library from the autocrine assay are then quantified. Compared with 0.50% positive population in negative control (no infection) and 32.18% in positive control (infected with lentivirus expressing the scFv-Leptin without insertion of the random 4-aa peptide), there are 4.22%, 18.91%, 1.43%, 1.43%, and 2.22% in libraries A, B, C, D, and E, respectively. The results indicate that peptide insertions at the non-CDR sites are permissive for maintain activity of the guest leptin molecule, although there is significant difference in terms of the level of tolerance of substitution at different antibody regions. Region B showed highest tolerance of substitution, which is consistent with the fact that it is structurally adjacent to CDRH1. Other regions also showed different level of tolerance of substitution, shedding light on potential positions where one can insert functional guests into antibody scaffold.

Example 10. Construction of Library of scRelaxin Molecules in an Antibody Scaffold The human relaxin-2 (relaxin-H2) is a heterodimeric hormone. It is composed of two chains, the 24-residue A chain and the 29-residue B chain. Structurally, relaxin-H2 contains 2 inter-chain (between A and B chains) and 1 intra-chain (inside A chain) disulfide bonds, which are critical to its biological functions. The relaxin-H2 interacts with the relaxin receptor RXFP1 (LGR7) and RXFP2 (LGR8), which belong to the 7-transmembrane G protein-coupled receptor superfamily. RXFP1 has been used in various assays determining activity of the relaxin-H2, more appropriately than RXFP2, RXFP3 or RXFP4. Besides, RXFP1 is one of those rare GPCRs, which have large extracellular domains.

To construct the relaxin-in-Ab library, A chain and B chain of relaxin-H2 were linked together using a flexible linker. This single-chain relaxin-H2 was then inserted into the CDRH3 of scaffold antibody, via engineered N-terminal and C-terminal linkers. The final cassette is [XXX]-[Loop1]-[A chain]-[Loop2]-[B chain]-[Loop3]-[XXX], where XXX stands for three randomized amino acid residues, Loop1 is either GGGGSGGGSGGS (SEQ ID NO:46) or GGSGGS (SEQ ID NO:47), Loop2 is GSGSGSGS (SEQ ID NO:45), and Loop3 is either SGGGGSGGGGSG (SEQ ID NO:48) or SGGGGS (SEQ ID NO:49). The host scFv scaffold (SEQ ID NO:1) is an antibody with a CDR H3 containing 19 amino acid residues (Kabat numbering). To maintain proper folding of the antibody core, while maximizing the flexibility of junctions, the LGITKTSTCYT loop (SEQ ID NO:3), which is the core of CDR H3, was replaced by members of the combinatorial N- and C-terminal junction library. The pool of scaffold scFv containing the relaxin-H2 cassette was transferred into a lentiviral vector. The final library size is $3.67\times10^7$. Lentiviruses expressing the library of scRelaxin-H2 molecules were produced in HEK 293T cells.

Example 11. Selecting Antibody-Embedded Functional Relaxin-H2 Agonists

Flow cytometry sorting of cells in which the expression of β-lactamase reporter gene is induced by various cell signaling responsive elements has been widely used because of its high accuracy and sensitivity. To build up a high throughput platform to discover agonistic antibodies from huge combinatorial libraries, a β-lactamase based reporter cell line was constructed. The HEK 293T cells were co-infected by two lentiviruses, one expresses RXFP1 which was under the control of EF-1α promoter, the other expresses β-lactamase upon stimulation of cAMP response element (CRE). The relaxin-H2 responsive cells (RXFP1 CRE-Bla) were sorted and pooled after stimulation by 10 ng/ml relaxin-H2 protein.

To select functional relaxin agonists, the RXFP1 CRE-Bla cells were transduced with the lentiviral combinatorial junction library at a multiplicity of infection of about 2. Lentiviruses were removed 5 hours after infection, and methylcellulose media was placed on top of cells to limit diffusion of secreted antibodies to neighboring cells. Twenty hours after lentivirus infection, the methylcellulose media was washed away with media and cells were trypsinized, loaded with LiveBLAzer-FRET B/G Substrate, and sorted. To avoid false positive clones, very stringent gating was applied. The sorted cells were lysed and used as template to amplify the scFv fragments using PCR for next round of sorting if necessary.

After four rounds of sorting, 60 clones were screened for the relaxin activity. Plasmids were extracted from each clone and transfected into HEK 293T cells to express the scFv containing relaxin. Forty-eight hours after transfection, supernatant was transferred for FRET assay using RXFP1 CRE-Bla cells. Out of the 60 clones, 9 were identified as agonistic (FIG. 5). Protein level in the supernatant of these 9 clones was measured with western blotting using anti-Flag antibody (FIG. 5). Based on the activity and protein level in the supernatant, clone A3 and C12 showed the highest potency. These two clones were converted into full IgG1 antibody using the pFuse vectors. Sequencing analysis showed that C12 was actually mixture of two clones, C12-2 and C12-1. The sequence information of the 10 embedded scRelaxin molecules, including the XXX terminal linker and the loop sequences is indicated in FIG. 6.

Example 12. Characterization of Identified Antibody-Embedded scRelaxin Agonists A3 (Ig1), C12-2 (Ig2), and C12-1 (Ig3) were expressed in the FreeStyle 293-F cells (Life Technologies). Both heavy chain and light chain plasmids were co-transfected into the FreeStyle 293-F cells following the manufacture's instruction. Three days after transfection, the supernatant was collected and purified to >95% purity using one-step affinity purification. The purity was detected with Coomassie blue stained SDS-PAGE gel (FIG. 7).

To characterize the purified antibodies, in vitro FRET assay was used to measure the EC50 values. The RXFP1 CRE-Bla cells were seeded into 384-well plate and serially diluted antibodies/relaxin-H2 protein (R&D Systems) were added into wells. The final concentration of antibodies/relaxin-H2 protein ranged from 0.033 nM to 135 nM. This is followed by incubating the plate in the cell incubator for five hours, then loading the LiveBLAzer-FRET B/G substrate and incubating at room temperature for another 2 hours. The FRET signals were collected and analyzed. As expected, the scaffold antibody showed no activity (FIG. 8). On the other hand, as shown in the FIG. 8, agonist activities of the identified scRelaxin were demonstrated by the measured EC50 values for Ig1, Ig2, Ig3 at 7.9 nM, 1.4 nM, 9.6 nM, respectively (the EC50 for the native relaxin-H2 molecule being 4.9 nM).

Example 13. Materials and Methods

This Example describes some of the materials and methods employed in generating some of the functional polypeptides embedded in an antibody scaffold as exemplified herein.

Reagents: Rabbit anti-phospho-STAT3 was from Cell Signaling. Human Leptin ELISA kit was from R&D. Mouse recombinant Leptin was from Amgen. Osmotic pumps and brain infusion kits were from Alzet.

Cell Culture: Human HEK 293T cells were maintained in DMEM containing 10% FBS, non-essential amino acids (NEAA), penicillin and streptomycin (P/S). The LepR SIE-Bla and FSHR CRE-Bla cells were grown in DMEM media supplemented with 10% dialyzed FBS (Life Technology), NEAA and P/S. The Baf3 LepR cells were cultured in RPMI-1640 with 10% FBS, P/S, and 10 ng/ml IL-3. The FreeStyle 293-F cells were maintained in FreeStyle F17 expression medium (Life Technology) supplemented with 4 mM GlutaMAX-I (Life Technology).

Construction of Combinatorial Antibody Libraries: BamHI and XmaI restriction sites were introduced into the CDR H3 loop in the scaffold. Leptin was amplified with combination of three forward primers (LF1, LF2, LF3) and three reverse primers (LR1, LR2, LR3) (Table 3) and cloned into the scaffold using BamHI and XmaI. Single chain FSH (scFSH) was constructed by linking the 3' of a gene encoding the β chain and the 5' of gene encoding the α chain with GGATCAGGATCGAACGCGACGGGGTCAGG TTCTAATGCAACTTCAGGATCGACTAGT (SEQ ID NO:2). Then scFSH was amplified using a strategy similar to that used for the Leptin constructs (Table 4).

TABLE 3

Primers used to construct combinatorial junction library of IgG-Leptin.

| LF1 | gcgagagGGATCCNKNNKNNKggcggTggcggGtctggTggagg tggAagcggAggtggAggGAGTGTGCCCATCCAAAAAGTCCAAG ATGACAC (SEQ ID NO: 21) |
|---|---|
| LF2 | gcgagagGGATCCNKNNKNNKggTggaggtggAagcggAggtgg AggGAGTGTGCCCATCCAAAAAGTCCAAGATGACAC (SEQ ID NO: 22) |
| LF3 | gcgagagGGATCCNKNNKNNKggAggtggAggGAGTGTGCCCAT CCAAAAAGTCCAAGATGACAC (SEQ ID NO: 23) |
| LR1 | gtccattaCCCGGGNMNNMNNggaCccAccaccTccActCccac ctccgccACTAccTccgccAccGCACCCAGGGCTGAGGTCCAGC (SEQ ID NO: 24) |
| LR2 | gtccattaCCCGGGNMNNMNNActCccacctccgccACTAccTc cgccAccGCACCCAGGGCTGAGGTCCAGC (SEQ ID NO: 25) |
| LR3 | gtccattaCCCGGGNMNNMNNACTAccTccgccAccGCACCCAG GGCTGAGGTCCAGC (SEQ ID NO: 26) |

TABLE 4

Primers used to construct combinatorial junction library of IgG-scFSH.

| FF1 | gcgagagGGATCCNKNNKNNKggcggTggcggGtctggTggaggt ggAagcggAggtggAggGAGTAATAGCTGTGAGCTGACCAACATC ACCATTG (SEQ ID NO: 27) |
|---|---|
| FF2 | gcgagagGGATCCNKNNKNNKggTggaggtggAagcggAggtggA ggGAGTAATAGCTGTGAGCTGACCAACATCACCATTG (SEQ ID NO: 28) |
| FF3 | gcgagagGGATCCNKNNKNNKggAggtggAggGAGTAATAGCTGT GAGCTGACCAACATCACCATTG (SEQ ID NO: 29) |
| FR1 | gtccattaCCCGGGNMNNMNNggaCccAccaccTccActCccacc tccgccACTAccTccgccAccGCTCTTGTGGTAGTAGCAGGTGCT GCAGTG (SEQ ID NO: 30) |

TABLE 4-continued

Primers used to construct combinatorial junction library of IgG-scFSH.

| FR2 | gtccattaCCCGGGNMNNMNNActCccacctccgccACTAccTcc gccAccGCTCTTGTGGTAGTAGCAGGTGCTGCAGTG (SEQ ID NO: 31) |
|---|---|
| FR3 | gtccattaCCCGGGNMNNMNNACTAccTccgccAccGCTCTTGTG GTAGTAGCAGGTGCTGCAGTG (SEQ ID NO: 32) |

Production of Lentiviruses: Human HEK 293T cells were transfected with the pLV2-based lentiviral plasmid together with pCMV-dR8.91 and pVSV-G packaging plasmids at a ratio of 1:1:1, using Lipofectamine 2000 transfection reagent (Life Technology). Lentiviruses in the supernatant were collected at 48 hours after transfection, and then filtered through a 0.45-μm polyethersulfone membrane filter (Millipore). The titer was measured using Lenti-X p24 Rapid Titer Kit (Clontech).

Construction of Stable Cell Lines: The human Leptin receptor (LepR) gene fused with C-terminal Hemagglutinin epitope (HA) tag was cloned into the pLV2-based vector in which the expression of the gene-of-interest was driven by the elongation factor-1 alpha (EF1α) promoter. The CellSensor SIE-Bla HEK293T cells were transduced and stimulated with 1 ng/ml of recombinant human Leptin protein (R&D Systems). Leptin-responsive cells were sorted using the LiveBLAzer-FRET B/G Loading Kit (Life Technology) with an excitation wavelength of 409 nm and emission wavelengths of 460 nm and 530 nm.

Construction of human FSHR cell line followed the same strategy as for the human LepR, except that cells were co-transduced with lentiviruses expressing β-lactamase controlled by CRE.

To construct Baf3 LepR cell line, the human LepR was cloned into pMSCVpuro vector, which was then transfected into Pheonix cells to generate retrovirus. IL-3-dependent Baf3 cells were infected with the retrovirus and cells were selected with 10 μg/ml puromycin. The puromycin-resistant cells were subsequently cultured in media containing 10 ng/ml Leptin.

Proliferation Assay: Baf3 LepR cells were washed with IL-3-free media three times, diluted to 0.2 million cells/ml, and seeded into a 96-well plate (80 μl/well). Serially diluted proteins (20 μl/well) were added to cells resulting in concentrations 1.25 pM, 12.5 pM, 125 pM, 1.25 nM, 12.5 nM, and 125 nM. Cells were cultured at 37° C. for another 48 hours. +CellTiter 96 AQ$_{ueous}$ One Solution Reagent (Promega) was added into cells (20 μl/well). The absorbance at 490 nm was recorded.

CD Spectroscopy Measurement: Purified proteins were dialyzed against sodium phosphate buffer twice and then diluted to 0.5 mM. The far-UV CD signal was collected on Aviv Circular Dichroism Spectrometer Model 420 using a 1-mm path length cuvette and measurements ranging between 260 to 190 nm were made at room temperature.

Differential HDX-MS: Differential, solution-phase amide HDX experiments were carried out using a fully automated system (CTC HTS PAL, LEAP Technologies, Carrboro, N.C.; housed inside a 4° C. cabinet) interfaced with an Orbitrap mass spectrometer (Exactive™, Thermo Fisher) as described previously with a few variations. For the differential HDX experiments, 5 μl of either the IgG-Leptin (10 μM) or Leptin (10 μM) alone were mixed with 20 μl of D$_2$O-containing HDX buffer (20 mM Tris 7.3, 150 mM NaCl, 5 mM DTT) and incubated at 4° C. for a predetermined time (0 s, 10 s, 30 s, 60 s, 900 s or 3,600 s). Following on exchange, unwanted forward or back exchange was minimized and the protein was denatured by the addition of 25 µl of a quench solution (1% v/v TFA in 3 M urea and 50 mM TCEP). Protein was then digested by passing through an immobilized 2 mm×2 cm pepsin column (prepared in house) at 200 µl min$^{-1}$ (0.1% v/v TFA, 15° C.) and the resulting peptic peptides were trapped on a 2 mm×1 cm $C_{18}$ trap column (Thermo Scientific). The bound peptides were then eluted with a linear gradient (5-50% $CH_3CN$ w/v and 0.3% w/v formic acid) across a 2 mm×50 mm $C_{18}$ HPLC column (Hypersil Gold, Thermo Fisher) for 8 min at 4° C.). Mass spectrometric data were acquired using an Exactive™ Plus Orbitrap mass spectrometer (Exactive™, Thermo Fisher). Each HDX experiment was carried out in triplicate and the differential HDX data was overlaid onto the crystal structure of human Leptin (PDB code: 1AX8) using PyMOL (Delano Scientific).

Peptide Identification and HDX data processing: MS/MS experiments were performed with an LTQ linear ion trap mass spectrometer (LTQ Orbitrap XL, Thermo Fisher) over a 70 min gradient. Product ion spectra were acquired in a data-dependent mode and the five most abundant ions were selected for the product ion analysis. The MS/MS *.raw data files were converted to *.mgf files and then submitted to Mascot (Matrix Science, London, UK) for peptide identification and scoring. Only the peptides that had a MASCOT score of 20 or greater were included in the peptide set used for HDX detection. The MS/MS MASCOT search was also performed against a decoy (reverse) sequence and false positives were ruled out. The MS/MS spectra of all the peptide ions from the MASCOT search were further checked manually and only the unique charged ions with the highest MASCOT score were used in estimating the sequence coverage. The intensity weighted average m/z value (centroid) of each peptide isotopic envelope and the deuterium uptake level for each peptide was calculated with the latest version of our in-house developed software, HDX Workbench. The corrections for back-exchange were made based on an estimated 70% deuterium recovery and accounting for the known 80% deuterium content of the on-exchange buffer.

Animal procedures: All surgical procedures in mice were performed in compliance with the protocols approved by the IACUC of The Rockefeller University. Wildtype C57Bl6/J, ob/ob, db/db and DIO (diet-induced obesity) mice were from The Jackson Laboratory.

To characterize their in vivo function by peripheral administration, proteins were delivered via osmotic pumps implanted subcutaneously, at 600 ng/h for Leptin, 3600 ng/h for IgG-Leptin, or 2920 ng/h for Scaffold control. For central administration, proteins were delivered to lateral ventricle via osmotic brain infusion pumps, at 50 ng/h for Leptin, and 300 ng/h for IgG-Leptin. Food intake and body weight for each mouse was measured daily during indicated experimental periods. Fat composition was measured using EchoMRI Body Composition Analyzer.

To determine the rate of protein clearance, a single dose of Leptin (4.5 µg) or IgG-Leptin (27 µg) was delivered into mice via the jugular vein, and blood was then collected at indicated time points. The plasma concentration of human Leptin was measured by ELISA.

To examine neuronal activation in vivo, ob/ob mice were treated with Leptin (2.5 µg/gram body weight) or IgG-Leptin (15 µg/gram body weight) via intraperitoneal injection, or with Leptin (100 ng) or IgG-Leptin (600 ng) via intracerebral ventricular injection. 1 hr after the treatment, mice were transcardially perfused with PBS followed by 4% paraformaldehyde. Brain samples were then dissected, post-fixed with 4% in the hypothalamus was determined by free-floating immunostaining as previously described in Knight et al., PloS one 5, e11376, 2010.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

```
Host scFv scaffold sequence (SEQ ID NO: 1):
QVQLVQSGAE VKKPGSSVKV SCKASGGTFS SYAISWVRQA

PGQGLEWMGG IIPIFGTANY AQKFQGRVTI TADESTSTAY

MELSSLRSED TAVYYCASQG

ILGITKTSTCYTRVMDVWGQGTTVVVSSRASLGGGGSGGGGSGGGGSTQA

GLTQPPSVSKGLRQTATLTCTGNSNNVGNQGAAWLQQHQGHPPKLLSYRN

NNRPSGISERLSASRSGNTASLTITGLQPEDEADYYCAAWDDSLNGQVVF

GGGTKLTVL

Clone A3 scRelaxin-H2 sequence plus terminal
linkers
                                    (SEQ ID NO: 69)
RTRGGSGGS-QLYSALANKCCHVGCTKRSLARFC-GSGSGSGS-
DSWMEEVIKLCGRELVRAQIAICGMSTWS-SGGGGSLMS Clone C12-2 scRelaxin-H2 sequence plus terminal
linkers
                                    (SEQ ID NO: 71)
RTRGGSGGS-QLYSALANKCCHVGCTKRSLARF'C-GSGSGSGS-
DSWMEEVIKLCGRELVRAQIAICGMSTWS-SGGGGSKPP Clone C12-1 scRelaxin-H2 sequence plus terminal
linkers
                                    (SEQ ID NO: 72)
PLNGGSGGS-QLYSALANKCCHVGCTKRSLARFC-GSGSGSGS-
DSWMEEVIKLCGRELVRAQIAICGMSTWS-SGGGGSKPP
```

What is claimed is:

1. A modified effector polypeptide that is embedded in an antibody scaffold, comprising a single chain variable region fragment (scFv) scaffold with its heavy chain complementary determining region 3 (HCDR3) substituted with an effector polypeptide; wherein the effector polypeptide is linked to the antibody sequence by an N-terminal linker and a C-terminal linker; and wherein the N-terminal linker comprises an amino acid sequence $X_3(G_{2-4}S)_{1-3}$, and the C-terminal linker comprises an amino acid sequence $(SG_{0-4})_{1-3}X_3$, wherein X is any amino acid residue, G is Glycine, S is Serine, wherein the number of G residue in each GS repeat can be different from that in the other GS repeats, wherein the scFv scaffold comprises SEQ ID NO:1, and wherein HCDR3 (LGITKTSTCYT; SEQ ID NO:3) in the scFv scaffold is replaced with the effector polypeptide.

2. The modified effector polypeptide of claim 1, wherein the effector polypeptide is a single chain human relaxin-2 (scRelaxin).

3. The modified effector polypeptide of claim 2, wherein the single chain relaxin polypeptide comprises A chain and B chain connected by a connector sequence (GS)n (SEQ ID NO:44), wherein n=3-5.

4. The modified effector polypeptide of claim 2, wherein the N-terminal linker comprises XXXGGGGSGGGSGGS (SEQ ID NO:78) or XXXGGSGGS (SEQ ID NO:79), and the C-terminal linker comprises SGGGGSGGGGSGXXX (SEQ ID NO:80) or SGGGGSXXX (SEQ ID NO:81), wherein X is any randomized amino acid residue.

5. The modified effector polypeptide of claim 2, wherein the N-terminal linker and the C-terminal linker are respectively substantially identical to sequences shown in (1) RTRGGSGGS (SEQ ID NO:50) and SGGGGSLMS (SEQ ID NO:51) (Clone A3); (2) RTRGGSGGS (SEQ ID NO:50) and SGGGGSKPP (SEQ ID NO:52) (Clone A12-2); (3) PLNGGSGGS (SEQ ID NO:53) and SGGGGSKPP (SEQ ID NO:52) (Clone C12-1); (4) LPRGGGGSGGGSGGS (SEQ ID NO:54) and SGGGGSLDS (SEQ ID NO:55); (5) QTTGGSGGS (SEQ ID NO:56) and SGGGGSKGT (SEQ ID NO:57); (6) HMFGGSGGS (SEQ ID NO:58) and SGGGGSKAP (SEQ ID NO:59); (7) QRGGGSGGS (SEQ ID NO:60) and SGGGGSWSP (SEQ ID NO:61); or (8) RQRGGGGSGGGSGGS (SEQ ID NO:62) and SGGGGSVRA (SEQ ID NO:63).

6. The modified effector polypeptide of claim 2, wherein the N-terminal linker and the C-terminal linker are respectively identical to the sequences shown in (1) RTRGGSGGS (SEQ ID NO:50) and SGGGGSLMS (SEQ ID NO:51) (Clone A3); (2) RTRGGSGGS (SEQ ID NO:50) and SGGGGSKPP (SEQ ID NO:52) (Clone A12-2); or (3) PLNGGSGGS (SEQ ID NO:53) and SGGGGSKPP (SEQ ID NO:52) (Clone C12-1).

7. The modified effector polypeptide of claim 2, wherein the LGITKTSTCYT (SEQ ID NO:3) loop is replaced with a linker-modified single chain human relaxin-2 sequence shown in SEQ ID NO:69, SEQ ID NO:71, or SEQ ID NO:72.

8. The modified effector polypeptide of claim 2, comprising an amino acid sequence that is substantially identical to a sequence selected from the group consisting of SEQ ID NOs:68-77.

9. An isolated or recombinant polynucleotide encoding the modified effector polypeptide of claim 1.

10. A method of treating or preventing the development of a disease or disorder that is associated with or mediated by relaxin-2 deficiency or impaired relaxin-2 signaling in a subject, comprising administering to the subject a pharmaceutical composition comprising a therapeutically effective amount of the modified or derivative relaxin molecule of claim 1.

11. The method of claim 10, wherein the disease or disorder is heart failure, fibrosis, hypertension, scleroderma, or cancer.

* * * * *